(12) United States Patent
Hariton et al.

(10) Patent No.: US 11,801,135 B2
(45) Date of Patent: Oct. 31, 2023

(54) TECHNIQUES FOR DEPLOYMENT OF A PROSTHETIC VALVE

(71) Applicant: CARDIOVALVE LTD., Or Yehuda (IL)

(72) Inventors: Ilia Hariton, Zichron Yaackov (IL); Boaz Harari, Ganey Tikva (IL); Maxim Karalnik, Karmiel (IL); Meni Iamberger, Kfar Saba (IL)

(73) Assignee: CARDIOVALVE LTD., Or Yehuda (IL)

( * ) Notice: Subject to any disclaimer, the term of this patent is extended or adjusted under 35 U.S.C. 154(b) by 156 days.

(21) Appl. No.: 17/141,853

(22) Filed: Jan. 5, 2021

(65) Prior Publication Data
US 2021/0145578 A1 May 20, 2021

Related U.S. Application Data

(63) Continuation of application No. 15/668,659, filed on Aug. 3, 2017, now Pat. No. 10,918,481, which is a
(Continued)

(51) Int. Cl.
*A61F 2/24* (2006.01)
*A61F 2/95* (2013.01)
*A61F 2/915* (2013.01)

(52) U.S. Cl.
CPC ........... *A61F 2/2436* (2013.01); *A61F 2/243* (2013.01); *A61F 2/2409* (2013.01);
(Continued)

(58) Field of Classification Search
CPC .... A61F 2/2403; A61F 2/2418; A61F 2/2409; A61F 2/243; A61F 2/2436
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CA 2822801 8/2006
CA 2671966 6/2008
(Continued)

OTHER PUBLICATIONS

An Office Action dated Nov. 25, 2021, which issued during the prosecution of European Patent Application No. 18826823.9.
(Continued)

*Primary Examiner* — Tuan V Nguyen
(74) *Attorney, Agent, or Firm* — Sughrue Mion, PLLC

(57) ABSTRACT

A method includes percutaneously advancing an implant to a native heart valve of a subject, the implant being housed in a compressed state within a delivery tool. Next, the method includes unhousing a longitudinally-intermediate portion of the implant, the longitudinally-intermediate portion being longitudinally between a longitudinally-proximal portion of the implant and a longitudinally distal portion of the implant. Subsequently, the longitudinally-proximal portion of the implant is unhoused. Subsequently, the longitudinally-distal portion of the implant is unhoused. By unhousing flanges of the implant, the flanges automatically expand. Upon the flanges expanding, a proximal end of each flange extends radially outward from a central longitudinal axis of the implant and longitudinally in a proximal direction. Other applications are also described.

17 Claims, 17 Drawing Sheets

Related U.S. Application Data continuation-in-part of application No. 15/541,783, filed as application No. PCT/IL2016/050125 on Feb. 3, 2016, now Pat. No. 9,974,651, said application No. 15/668,659 is a continuation-in-part of application No. PCT/IL2016/050125, filed on Feb. 3, 2016.

(60) Provisional application No. 62/112,343, filed on Feb. 5, 2015.

(52) U.S. Cl.
CPC .......... *A61F 2/2418* (2013.01); *A61F 2/9517* (2020.05); *A61F 2002/91575* (2013.01); *A61F 2220/0016* (2013.01); *A61F 2220/0025* (2013.01)

(56) References Cited

U.S. PATENT DOCUMENTS

| | | |
|---|---|---|
| 3,840,018 A | 10/1974 | Heifetz |
| 3,874,388 A | 4/1975 | King et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,222,126 A | 9/1980 | Boretos et al. |
| 4,261,342 A | 4/1981 | Aranguren |
| 4,275,469 A | 6/1981 | Gabbay |
| 4,340,091 A | 7/1982 | Skelton et al. |
| 4,423,525 A | 1/1984 | Vallana et al. |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,853,986 A | 8/1989 | Allen |
| 4,892,541 A | 1/1990 | Alonso |
| 4,917,698 A | 4/1990 | Carpenter et al. |
| 4,961,738 A | 10/1990 | Mackin |
| 4,972,494 A | 11/1990 | White et al. |
| 4,994,077 A | 2/1991 | Dobben |
| 5,061,277 A | 10/1991 | Carpentier et al. |
| 5,078,739 A | 1/1992 | Martin |
| 5,104,407 A | 4/1992 | Lam et al. |
| 5,108,420 A | 4/1992 | Marks |
| 5,201,757 A | 4/1993 | Heyn et al. |
| 5,201,880 A | 4/1993 | Wright |
| 5,258,008 A | 11/1993 | Wilk |
| 5,300,034 A | 4/1994 | Behnke |
| 5,306,296 A | 4/1994 | Wright et al. |
| 5,314,473 A | 5/1994 | Godin |
| 5,325,845 A | 7/1994 | Adair |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,450,860 A | 9/1995 | O'Connor |
| 5,473,812 A | 12/1995 | Morris et al. |
| 5,477,856 A | 12/1995 | Lundquist |
| 5,601,572 A | 2/1997 | Middleman et al. |
| 5,607,444 A | 3/1997 | Lam |
| 5,607,470 A | 3/1997 | Milo |
| 5,626,609 A | 5/1997 | Zvenyatsky et al. |
| 5,647,857 A | 7/1997 | Anderson et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,713,948 A | 2/1998 | Uflacker |
| 5,716,370 A | 2/1998 | Williamson et al. |
| 5,716,397 A | 2/1998 | Myers |
| 5,716,417 A | 2/1998 | Girard et al. |
| 5,728,116 A | 3/1998 | Rosenman |
| 5,730,150 A | 3/1998 | Peppel et al. |
| 5,741,297 A | 4/1998 | Simon |
| 5,749,371 A | 5/1998 | Zadini et al. |
| 5,765,682 A | 6/1998 | Bley et al. |
| 5,776,140 A | 7/1998 | Cottone |
| 5,810,882 A | 9/1998 | Bolduc |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,868,777 A | 2/1999 | Lam |
| 5,873,906 A | 2/1999 | Lau et al. |
| 5,876,373 A | 3/1999 | Giba et al. |
| 5,935,098 A | 8/1999 | Blaisdell et al. |
| 5,954,766 A | 9/1999 | Zadno-Azizi et al. |
| 5,957,949 A | 9/1999 | Leonhardt et al. |
| 5,957,953 A | 9/1999 | DiPoto et al. |
| 5,961,440 A | 10/1999 | Schweich et al. |
| 5,961,539 A | 10/1999 | Northrup, III et al. |
| 5,980,565 A | 11/1999 | Jayaraman |
| 5,984,959 A | 11/1999 | Robertson |
| 6,010,530 A | 1/2000 | Goicoechea |
| 6,019,787 A | 2/2000 | Richard et al. |
| 6,042,554 A | 3/2000 | Rosenman |
| 6,042,607 A | 3/2000 | Williamson, IV |
| 6,045,497 A | 4/2000 | Schweich et al. |
| 6,050,936 A | 4/2000 | Schweich et al. |
| 6,059,715 A | 5/2000 | Schweich et al. |
| 6,059,827 A | 5/2000 | Fenton |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern |
| 6,110,200 A | 8/2000 | Hinnenkamp |
| 6,113,612 A | 9/2000 | Swanson et al. |
| 6,120,534 A | 9/2000 | Ruiz |
| 6,126,686 A | 10/2000 | Badylak et al. |
| 6,143,024 A | 11/2000 | Campbell et al. |
| 6,152,937 A | 11/2000 | Peterson et al. |
| 6,159,240 A | 12/2000 | Sparer |
| 6,165,119 A | 12/2000 | Schweich et al. |
| 6,165,183 A | 12/2000 | Kuehn et al. |
| 6,165,210 A | 12/2000 | Lau et al. |
| 6,174,332 B1 | 1/2001 | Loch |
| 6,183,411 B1 | 2/2001 | Mortier et al. |
| 6,187,020 B1 | 2/2001 | Zegdi et al. |
| 6,187,040 B1 | 2/2001 | Wright |
| 6,193,686 B1 | 2/2001 | Estrada et al. |
| 6,193,745 B1 | 2/2001 | Fogarty et al. |
| 6,315,784 B1 | 2/2001 | Djurovic |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,254,609 B1 | 7/2001 | Vrba et al. |
| 6,264,700 B1 | 7/2001 | Kilcoyne et al. |
| 6,287,339 B1 | 9/2001 | Vasquez et al. |
| 6,296,656 B1 | 10/2001 | Bolduc et al. |
| 6,312,465 B1 | 11/2001 | Griffin et al. |
| 6,319,281 B1 | 11/2001 | Patel |
| 6,332,893 B1 | 12/2001 | Mortier et al. |
| 6,334,873 B1 | 1/2002 | Lane et al. |
| 6,346,074 B1 | 2/2002 | Roth |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV |
| 6,406,420 B1 | 6/2002 | McCarthy et al. |
| 6,406,493 B1 | 6/2002 | Tu et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,451,054 B1 | 9/2002 | Stevens |
| 6,454,799 B1 | 9/2002 | Schreck |
| 6,458,153 B1 | 10/2002 | Bailey et al. |
| 6,461,366 B1 | 10/2002 | Seguin |
| 6,470,892 B1 | 10/2002 | Forsell |

(56) References Cited

U.S. PATENT DOCUMENTS

| | | |
|---|---|---|
| 6,478,807 B1 | 11/2002 | Foreman et al. |
| 6,482,228 B1 | 11/2002 | Norred |
| 6,491,711 B1 | 12/2002 | Durcan |
| 6,503,274 B1 | 1/2003 | Howanec et al. |
| 6,511,491 B2 | 1/2003 | Grudem et al. |
| 6,524,338 B1 | 2/2003 | Gundry |
| 6,530,952 B2 | 3/2003 | Vesely |
| 6,533,772 B1 | 3/2003 | Sherts et al. |
| 6,537,314 B2 | 3/2003 | Langberg et al. |
| 6,540,782 B1 | 4/2003 | Snyders |
| 6,547,801 B1 | 4/2003 | Dargent et al. |
| 6,551,350 B1 | 4/2003 | Thornton et al. |
| 6,554,845 B1 | 4/2003 | Fleenor et al. |
| 6,558,396 B1 | 5/2003 | Inoue |
| 6,558,418 B2 | 5/2003 | Carpentier et al. |
| 6,564,805 B2 | 5/2003 | Garrison et al. |
| 6,565,603 B2 | 5/2003 | Cox |
| 6,569,196 B1 | 5/2003 | Vesely |
| 6,569,198 B1 | 5/2003 | Wilson et al. |
| 6,579,297 B2 | 6/2003 | Bicek et al. |
| 6,582,464 B2 | 6/2003 | Gabbay |
| 6,589,160 B2 | 7/2003 | Schweich et al. |
| 6,602,263 B1 | 8/2003 | Swanson et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,616,675 B1 | 9/2003 | Evard et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,699,256 B1 | 3/2004 | Logan et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,456 B2 | 3/2004 | Langberg et al. |
| 6,711,444 B2 | 3/2004 | Koblish |
| 6,716,244 B2 | 4/2004 | Klaco |
| 6,718,985 B2 | 4/2004 | Hlavka et al. |
| 6,719,781 B1 | 4/2004 | Kim |
| 6,719,786 B2 | 4/2004 | Ryan et al. |
| 6,719,788 B2 | 4/2004 | Cox |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,514 B1 | 7/2004 | Li et al. |
| 6,764,518 B2 | 7/2004 | Godin |
| 6,767,362 B2 | 7/2004 | Schreck |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,821,297 B2 | 11/2004 | Snyders |
| 6,830,585 B1 | 12/2004 | Artof et al. |
| 6,830,638 B2 | 12/2004 | Boylan et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,884,257 B1 | 4/2005 | Cox |
| 6,893,459 B1 | 5/2005 | Macoviak |
| 6,893,460 B2 | 5/2005 | Spenser et al. |
| 6,908,482 B2 | 6/2005 | McCarthy et al. |
| 6,918,917 B1 | 7/2005 | Nguyen et al. |
| 6,926,715 B1 | 8/2005 | Hauck et al. |
| 6,926,730 B1 | 8/2005 | Nguyen et al. |
| 6,951,571 B1 | 10/2005 | Srivastava |
| 6,960,217 B2 | 11/2005 | Bolduc |
| 6,964,684 B2 | 11/2005 | Ortiz et al. |
| 6,964,686 B2 | 11/2005 | Gordon |
| 6,974,476 B2 | 12/2005 | McGuckin et al. |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,041,132 B2 | 5/2006 | Quijano et al. |
| 7,074,236 B2 | 7/2006 | Rabkin et al. |
| 7,077,850 B2 | 7/2006 | Kortenbach |
| 7,077,861 B2 | 7/2006 | Spence |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,137,184 B2 | 11/2006 | Schreck |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,656 B2 | 2/2007 | Khairkhahan |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,261,686 B2 | 8/2007 | Couvillon, Jr. |
| 7,288,097 B2 | 10/2007 | Seguin |
| 7,288,111 B1 | 10/2007 | Holloway et al. |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,316,716 B2 | 1/2008 | Egan |
| 7,329,279 B2 | 2/2008 | Haug et al. |
| 7,329,280 B2 | 2/2008 | Bolling et al. |
| 7,335,213 B1 | 2/2008 | Hyde et al. |
| 7,351,256 B2 | 4/2008 | Hojeibane et al. |
| 7,361,190 B2 | 4/2008 | Shoulian et al. |
| 7,364,588 B2 | 4/2008 | Mathis et al. |
| 7,374,571 B2 | 5/2008 | Pease et al. |
| 7,374,573 B2 | 5/2008 | Gabbay |
| 7,377,938 B2 | 5/2008 | Sarac et al. |
| 7,377,941 B2 | 5/2008 | Rhee et al. |
| 7,381,218 B2 | 6/2008 | Schreck |

(56) References Cited

U.S. PATENT DOCUMENTS

| | | |
|---|---|---|
| 7,381,219 B2 | 6/2008 | Salahieh et al. |
| 7,390,329 B2 | 6/2008 | Westra et al. |
| 7,404,824 B1 | 7/2008 | Webler et al. |
| 7,422,603 B2 | 9/2008 | Lane |
| 7,429,269 B2 | 9/2008 | Schwammenthal |
| 7,431,692 B2 | 10/2008 | Zollinger et al. |
| 7,442,204 B2 | 10/2008 | Schwammenthal |
| 7,442,207 B2 | 10/2008 | Rafiee |
| 7,445,630 B2 | 11/2008 | Lashinski et al. |
| 7,452,376 B2 | 11/2008 | Lim et al. |
| 7,455,677 B2 | 11/2008 | Vargas et al. |
| 7,455,688 B2 | 11/2008 | Furst et al. |
| 7,455,690 B2 | 11/2008 | Cartledge et al. |
| 7,462,162 B2 | 12/2008 | Phan et al. |
| 7,481,838 B2 | 1/2009 | Carpentier et al. |
| 7,485,142 B2 | 2/2009 | Milo |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,527,647 B2 | 5/2009 | Spence |
| 7,530,995 B2 | 5/2009 | Quijano et al. |
| 7,549,983 B2 | 6/2009 | Roue et al. |
| 7,556,632 B2 | 7/2009 | Zadno |
| 7,556,646 B2 | 7/2009 | Yang et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,582,111 B2 | 9/2009 | Krolik et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,597,711 B2 | 10/2009 | Drews et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,611,534 B2 | 11/2009 | Kapadia et al. |
| 7,618,449 B2 | 11/2009 | Tremulis et al. |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,648,528 B2 | 1/2010 | Styrc |
| 7,655,015 B2 | 2/2010 | Goldfarb et al. |
| 7,666,204 B2 | 2/2010 | Thornton et al. |
| 7,682,319 B2 | 3/2010 | Martin |
| 7,682,369 B2 | 3/2010 | Seguin |
| 7,682,380 B2 | 3/2010 | Thornton et al. |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,722,666 B2 | 5/2010 | Lafontaine |
| 7,731,741 B2 | 6/2010 | Eidenschink |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,753,922 B2 | 7/2010 | Starksen |
| 7,753,924 B2 | 7/2010 | Starksen et al. |
| 7,753,949 B2 | 7/2010 | Lamphere et al. |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,080 B2 | 8/2010 | Bei et al. |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,368 B2 | 1/2011 | Zollinger et al. |
| 7,871,432 B2 | 1/2011 | Bergin |
| 7,871,433 B2 | 1/2011 | Lattouf |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,393 B2 | 8/2011 | Carpentier et al. |
| 7,993,397 B2 | 8/2011 | Lashinski |
| 8,002,825 B2 | 8/2011 | Letac et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,103 B2 | 10/2011 | Burriesci |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,592 B2 | 11/2011 | Goldfarb et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,070,805 B2 | 12/2011 | Vidlund |
| 8,075,611 B2 | 12/2011 | Milwee et al. |
| 8,075,616 B2 | 12/2011 | Solem |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |

(56) References Cited

U.S. PATENT DOCUMENTS

| | | |
|---|---|---|
| 8,092,518 B2 | 1/2012 | Schreck |
| 8,092,520 B2 | 1/2012 | Quadri |
| 8,092,521 B2 | 1/2012 | Figulla et al. |
| 8,100,964 B2 | 1/2012 | Spence |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,123,800 B2 | 2/2012 | McCarthy |
| 8,123,801 B2 | 2/2012 | Milo |
| 8,323,334 B2 | 2/2012 | Deem et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,493 B2 | 3/2012 | Spence et al. |
| 8,142,494 B2 | 3/2012 | Rahdert et al. |
| 8,142,495 B2 | 3/2012 | Hasenkam et al. |
| 8,142,496 B2 | 3/2012 | Berreklouw |
| 8,142,497 B2 | 3/2012 | Friedman |
| 8,147,504 B2 | 4/2012 | Ino et al. |
| 8,147,542 B2 | 4/2012 | Maisano et al. |
| 8,152,844 B2 | 4/2012 | Rao |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,013 B2 | 4/2012 | Machold et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez-Duran |
| 8,211,169 B2 | 7/2012 | Lane et al. |
| 8,216,256 B2 | 7/2012 | Raschdorf, Jr. et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,226,711 B2 | 7/2012 | Mortier et al. |
| 8,231,670 B2 | 7/2012 | Salahieh et al. |
| 8,231,671 B2 | 7/2012 | Kim |
| 8,236,045 B2 | 8/2012 | Benichou et al. |
| 8,236,049 B2 | 8/2012 | Rowe et al. |
| 8,241,351 B2 | 8/2012 | Cabiri |
| 8,252,042 B2 | 8/2012 | McNamara et al. |
| 8,252,050 B2 | 8/2012 | Maisano et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,262,725 B2 | 9/2012 | Subramanian |
| 8,267,988 B2 | 9/2012 | Hamer et al. |
| 8,277,501 B2 | 10/2012 | Chalekian et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,298,280 B2 | 10/2012 | Yadin et al. |
| 8,303,608 B2 | 11/2012 | Goldfarb et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,333,777 B2 | 12/2012 | Schaller et al. |
| 8,337,541 B2 | 12/2012 | Quadri et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,349,002 B2 | 1/2013 | Milo |
| 8,353,956 B2 | 1/2013 | Miller et al. |
| 8,357,195 B2 | 1/2013 | Kuehn |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,382,829 B1 | 2/2013 | Call et al. |
| 8,388,680 B2 | 3/2013 | Starksen et al. |
| 8,393,517 B2 | 3/2013 | Milo |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,926 B2 | 4/2013 | Kirson |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,460,370 B2 | 6/2013 | Zakay et al. |
| 8,460,371 B2 | 6/2013 | Hlavka et al. |
| 8,474,460 B2 | 7/2013 | Barrett et al. |
| 8,475,491 B2 | 7/2013 | Milo |
| 8,480,732 B2 | 7/2013 | Subramanian |
| 8,500,800 B2 | 8/2013 | Maisano et al. |
| 8,500,821 B2 | 8/2013 | Sobrino-Serrano et al. |
| 8,512,400 B2 | 8/2013 | Tran et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,529,431 B2 | 9/2013 | Baker et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,545,553 B2 | 10/2013 | Zipory et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,591,576 B2 | 11/2013 | Hasenkam et al. |
| 8,608,797 B2 | 12/2013 | Gross et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,696,742 B2 | 4/2014 | Pintor et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,507 B2 | 5/2014 | Keranen |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,778,021 B2 | 7/2014 | Cartledge |

(56) References Cited

U.S. PATENT DOCUMENTS

| | | |
|---|---|---|
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,840,663 B2 | 9/2014 | Salahieh et al. |
| 8,840,664 B2 | 9/2014 | Karapetian et al. |
| 8,845,717 B2 | 9/2014 | Khairkhahan et al. |
| 8,845,722 B2 | 9/2014 | Gabbay |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,888,843 B2 | 11/2014 | Khairkhahan et al. |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,461 B2 | 12/2014 | Traynor et al. |
| 8,911,489 B2 | 12/2014 | Ben-Muvhar |
| 8,911,493 B2 | 12/2014 | Rowe et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,468 B2 | 4/2015 | Ketai et al. |
| 9,011,520 B2 | 4/2015 | Miller et al. |
| 9,011,527 B2 | 4/2015 | Li et al. |
| 9,011,530 B2 | 4/2015 | Reich et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,119,719 B2 | 9/2015 | Zipory et al. |
| 9,125,632 B2 | 9/2015 | Loulmet et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,646 B2 | 11/2015 | Fabro |
| 9,173,659 B2 | 11/2015 | Bodewadt et al. |
| 9,173,738 B2 | 11/2015 | Murray et al. |
| 9,180,005 B1 | 11/2015 | Lashinski et al. |
| 9,192,472 B2 | 11/2015 | Gross et al. |
| 9,220,594 B2 | 12/2015 | Braido et al. |
| 9,226,820 B2 | 1/2016 | Braido et al. |
| 9,226,825 B2 | 1/2016 | Starksen et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,265,608 B2 | 2/2016 | Miller et al. |
| 9,277,994 B2 | 3/2016 | Miller et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,551 B2 | 3/2016 | Straubinger et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,320,591 B2 | 4/2016 | Bolduc |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,351,830 B2 | 5/2016 | Gross et al. |
| 9,387,078 B2 | 7/2016 | Gross et al. |
| 9,393,110 B2 | 7/2016 | Levi et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,510,947 B2 | 12/2016 | Straubinger et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 9,987,132 B1 | 6/2018 | Hariton et al. |
| 9,993,360 B2 | 6/2018 | Shalev et al. |
| 10,010,414 B2 | 7/2018 | Cooper et al. |
| 10,045,845 B2 | 8/2018 | Hacohen et al. |
| 10,076,415 B1 | 9/2018 | Metchik et al. |
| 10,098,732 B1 | 10/2018 | Hariton et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |

(56) References Cited

U.S. PATENT DOCUMENTS

| | | |
|---|---|---|
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,206,668 B2 | 2/2019 | Mcgoldrick et al. |
| 10,226,341 B2 | 3/2019 | Gross et al. |
| 10,231,831 B2 | 3/2019 | Hacohen |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |
| 10,292,816 B2 | 5/2019 | Raanani et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,376,361 B2 | 8/2019 | Gross et al. |
| 10,390,952 B2 | 8/2019 | Hariton et al. |
| 10,426,614 B2 | 10/2019 | Hariton et al. |
| 10,449,047 B2 | 10/2019 | Hariton et al. |
| 10,456,256 B2 | 10/2019 | Braido et al. |
| 10,492,908 B2 | 12/2019 | Hammer et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,537,426 B2 | 1/2020 | Iamberger et al. |
| 10,548,726 B2 | 2/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,610,359 B2 | 4/2020 | Hacohen |
| 10,631,871 B2 | 4/2020 | Goldfarb et al. |
| 10,631,982 B2 | 4/2020 | Hammer et al. |
| 10,646,342 B1 | 5/2020 | Marr et al. |
| 10,660,751 B2 | 5/2020 | Hacohen |
| 10,667,908 B2 | 6/2020 | Hariton et al. |
| 10,667,912 B2 | 6/2020 | Dixon et al. |
| 10,682,227 B2 | 6/2020 | Hariton et al. |
| 10,695,177 B2 | 6/2020 | Hariton et al. |
| 10,702,385 B2 | 7/2020 | Hacohen et al. |
| 10,736,742 B2 | 8/2020 | Hariton et al. |
| 10,758,342 B2 | 9/2020 | Chau et al. |
| 10,779,939 B2 | 9/2020 | Hariton et al. |
| 10,813,760 B2 | 10/2020 | Metchik et al. |
| 10,820,998 B2 | 11/2020 | Marr et al. |
| 10,842,627 B2 | 11/2020 | Delgado et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,874,514 B2 | 12/2020 | Dixon et al. |
| 10,888,422 B2 | 1/2021 | Hariton et al. |
| 10,888,425 B2 | 1/2021 | Delgado et al. |
| 10,888,644 B2 | 1/2021 | Ratz et al. |
| 10,905,552 B2 | 2/2021 | Dixon et al. |
| 10,905,554 B2 | 2/2021 | Cao |
| 10,918,481 B2 | 2/2021 | Hariton et al. |
| 10,918,483 B2 | 2/2021 | Metchik et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,993,809 B2 | 5/2021 | McCann et al. |
| 11,065,114 B2 | 7/2021 | Raanani et al. |
| 11,083,582 B2 | 8/2021 | McCann et al. |
| 11,147,672 B2 | 10/2021 | McCann et al. |
| 11,179,240 B2 | 11/2021 | Delgado et al. |
| 11,291,545 B2 | 4/2022 | Hacohen |
| 11,291,546 B2 | 4/2022 | Gross et al. |
| 11,291,547 B2 | 4/2022 | Gross et al. |
| 11,304,806 B2 | 4/2022 | Hariton et al. |
| 11,389,297 B2 | 7/2022 | Franklin et al. |
| 2001/0002445 A1 | 5/2001 | Vesely |
| 2001/0005787 A1 | 6/2001 | Oz et al. |
| 2001/0021872 A1 | 9/2001 | Bailey et al. |
| 2001/0021874 A1 | 9/2001 | Carpentier et al. |
| 2001/0044656 A1 | 11/2001 | Williamson et al. |
| 2001/0056295 A1 | 12/2001 | Solem |
| 2002/0013571 A1 | 1/2002 | Goldfarb et al. |
| 2002/0022862 A1 | 2/2002 | Grafton et al. |
| 2002/0029080 A1 | 3/2002 | Mortier et al. |
| 2002/0032481 A1 | 3/2002 | Gabbay |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0099436 A1 | 7/2002 | Thornton et al. |
| 2002/0103532 A1 | 8/2002 | Langberg et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177894 A1 | 11/2002 | Acosta et al. |
| 2002/0177904 A1 | 11/2002 | Huxel et al. |
| 2002/0198586 A1 | 12/2002 | Inoue |
| 2003/0009236 A1 | 1/2003 | Godin |
| 2003/0018358 A1 | 1/2003 | Saadat |
| 2003/0036791 A1 | 2/2003 | Philipp et al. |
| 2003/0050693 A1 | 3/2003 | Quijano et al. |
| 2003/0050694 A1 | 3/2003 | Yang et al. |
| 2003/0060846 A1 | 3/2003 | Egnelov et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0130731 A1 | 7/2003 | Vidlund et al. |
| 2003/0158578 A1 | 8/2003 | Pantages et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010272 A1 | 1/2004 | Manetakis et al. |
| 2004/0019377 A1 | 1/2004 | Taylor et al. |
| 2004/0024451 A1 | 2/2004 | Johnson et al. |
| 2004/0030382 A1 | 2/2004 | St. Goar et al. |
| 2004/0039414 A1 | 2/2004 | Carley et al. |
| 2004/0039436 A1 | 2/2004 | Spenser et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0093060 A1 | 5/2004 | Seguin et al. |
| 2004/0122448 A1 | 6/2004 | Levine |
| 2004/0122503 A1 | 6/2004 | Campbell et al. |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133267 A1 | 7/2004 | Lane |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |

(56) References Cited

U.S. PATENT DOCUMENTS

| | | |
|---|---|---|
| 2004/0143315 A1 | 7/2004 | Bruun et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0176839 A1 | 9/2004 | Huynh et al. |
| 2004/0181287 A1 | 9/2004 | Gellman |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0236419 A1 | 11/2004 | Milo |
| 2004/0249433 A1 | 12/2004 | Freitag |
| 2004/0249453 A1 | 12/2004 | Cartledge et al. |
| 2004/0260317 A1 | 12/2004 | Bloom et al. |
| 2004/0260389 A1 | 12/2004 | Case et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055038 A1 | 3/2005 | Kelleher et al. |
| 2005/0055086 A1 | 3/2005 | Stobie |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075726 A1 | 4/2005 | Svanidze et al. |
| 2005/0075727 A1 | 4/2005 | Wheatley |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0182483 A1 | 8/2005 | Osborne et al. |
| 2005/0182486 A1 | 8/2005 | Gabbay |
| 2005/0187613 A1 | 8/2005 | Bolduc et al. |
| 2005/0192596 A1 | 9/2005 | Jugenheimer et al. |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0203618 A1 | 9/2005 | Sharkawy et al. |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256532 A1 | 11/2005 | Nayak et al. |
| 2005/0256566 A1 | 11/2005 | Gabbay |
| 2005/0267478 A1 | 12/2005 | Corradi et al. |
| 2005/0267573 A9 | 12/2005 | Macoviak et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004439 A1 | 1/2006 | Spenser et al. |
| 2006/0004442 A1 | 1/2006 | Spenser et al. |
| 2006/0004443 A1 | 1/2006 | Liddicoat et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041189 A1 | 2/2006 | Vancaillie |
| 2006/0041319 A1 | 2/2006 | Taylor et al. |
| 2006/0052867 A1 | 3/2006 | Revuelta et al. |
| 2006/0052868 A1 | 3/2006 | Mortier |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0089627 A1 | 4/2006 | Burnett et al. |
| 2006/0095009 A1 | 5/2006 | Lampropoulos et al. |
| 2006/0106423 A1 | 5/2006 | Weisel et al. |
| 2006/0111773 A1 | 5/2006 | Rittgers et al. |
| 2006/0116750 A1 | 6/2006 | Herbert et al. |
| 2006/0116757 A1 | 6/2006 | Lashinski et al. |
| 2006/0122692 A1 | 6/2006 | Gilad et al. |
| 2006/0129166 A1 | 6/2006 | Lavelle |
| 2006/0135964 A1 | 6/2006 | Vesley |
| 2006/0149280 A1 | 7/2006 | Harvine et al. |
| 2006/0149368 A1 | 7/2006 | Spence |
| 2006/0155357 A1 | 7/2006 | Melsheimer |
| 2006/0161250 A1 | 7/2006 | Shaw |
| 2006/0161265 A1 | 7/2006 | Levine et al. |
| 2006/0047297 A1 | 8/2006 | Case |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0184240 A1 | 8/2006 | Jimenez et al. |
| 2006/0184242 A1 | 8/2006 | Lichtenstein |
| 2006/0190036 A1 | 8/2006 | Wendel et al. |
| 2006/0190038 A1 | 8/2006 | Carley et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0216404 A1 | 9/2006 | Seyler et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0247763 A1 | 11/2006 | Slater |
| 2006/0253191 A1 | 11/2006 | Salahieh et al. |
| 2006/0259135 A1 | 11/2006 | Navia et al. |
| 2006/0259136 A1 | 11/2006 | Nguyen et al. |

(56) References Cited

U.S. PATENT DOCUMENTS

| | | |
|---|---|---|
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0271175 A1 | 11/2006 | Woolfson |
| 2006/0282150 A1 | 12/2006 | Olson et al. |
| 2006/0282161 A1 | 12/2006 | Huyn et al. |
| 2006/0287661 A1 | 12/2006 | Bolduc et al. |
| 2006/0287716 A1 | 12/2006 | Banbury et al. |
| 2006/0287719 A1 | 12/2006 | Rowe et al. |
| 2007/0001627 A1 | 1/2007 | Lin et al. |
| 2007/0008018 A1 | 1/2007 | Nagashima et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027528 A1 | 2/2007 | Agnew |
| 2007/0027533 A1 | 2/2007 | Douk |
| 2007/0027536 A1 | 2/2007 | Mihaljevic et al. |
| 2007/0027549 A1 | 2/2007 | Godin |
| 2007/0038221 A1 | 2/2007 | Fine et al. |
| 2007/0038293 A1 | 2/2007 | St. Goar et al. |
| 2007/0038295 A1 | 2/2007 | Case et al. |
| 2007/0043435 A1 | 2/2007 | Seguin et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0055340 A1 | 3/2007 | Pryor |
| 2007/0056346 A1 | 3/2007 | Spenser et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0078510 A1 | 4/2007 | Ryan |
| 2007/0080188 A1 | 4/2007 | Spence et al. |
| 2007/0083168 A1 | 4/2007 | Whiting et al. |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198082 A1 | 8/2007 | Kapadia et al. |
| 2007/0198097 A1 | 8/2007 | Zegdi |
| 2007/0208550 A1 | 9/2007 | Cao et al. |
| 2007/0213582 A1 | 9/2007 | Zollinger et al. |
| 2007/0213810 A1 | 9/2007 | Newhauser et al. |
| 2007/0213813 A1 | 9/2007 | Von Segesser et al. |
| 2007/0219558 A1 | 9/2007 | Deutsch |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0233239 A1 | 10/2007 | Navia et al. |
| 2007/0239208 A1 | 10/2007 | Crawford |
| 2007/0239272 A1 | 10/2007 | Navia et al. |
| 2007/0239273 A1 | 10/2007 | Allen |
| 2007/0244546 A1 | 10/2007 | Francis |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004688 A1 | 1/2008 | Spenser et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Mackoviak et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086138 A1 | 4/2008 | Stone et al. |
| 2008/0086164 A1 | 4/2008 | Rowe et al. |
| 2008/0086203 A1 | 4/2008 | Roberts |
| 2008/0086204 A1 | 4/2008 | Rankin |
| 2008/0091257 A1 | 4/2008 | Andreas et al. |
| 2008/0091261 A1 | 4/2008 | Long et al. |
| 2008/0097523 A1 | 4/2008 | Bolduc et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0140116 A1 | 6/2008 | Bonutti |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195126 A1 | 8/2008 | Solem |
| 2008/0195200 A1 | 8/2008 | Vidlund et al. |
| 2008/0200980 A1 | 8/2008 | Robin et al. |
| 2008/0208265 A1 | 8/2008 | Frazier et al. |
| 2008/0208328 A1 | 8/2008 | Antocci et al. |
| 2008/0208330 A1 | 8/2008 | Keranen |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0294234 A1 | 11/2008 | Hartley et al. |
| 2008/0300629 A1 | 12/2008 | Surti |
| 2009/0005863 A1 | 1/2009 | Goetz et al. |
| 2009/0036966 A1 | 2/2009 | O'Connor et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082844 A1 | 3/2009 | Zacharias et al. |
| 2009/0088836 A1 | 4/2009 | Bishop et al. |
| 2009/0088837 A1 | 4/2009 | Gillinov et al. |
| 2009/0099554 A1 | 4/2009 | Forster et al. |
| 2009/0099650 A1 | 4/2009 | Bolduc et al. |
| 2009/0105794 A1* | 4/2009 | Ziarno ............... A61F 2/2436 600/481 |
| 2009/0105816 A1 | 4/2009 | Olsen et al. |
| 2009/0112159 A1 | 4/2009 | Slattery et al. |
| 2009/0125098 A1 | 5/2009 | Chuter |
| 2009/0125102 A1 | 5/2009 | Cartledge |

(56) References Cited

U.S. PATENT DOCUMENTS

| | | |
|---|---|---|
| 2009/0149872 A1 | 6/2009 | Gross et al. |
| 2009/0157175 A1 | 6/2009 | Benichou |
| 2009/0163934 A1 | 6/2009 | Raschdorf, Jr. et al. |
| 2009/0177274 A1 | 6/2009 | Scorsin et al. |
| 2009/0171363 A1 | 7/2009 | Chocron |
| 2009/0171439 A1 | 7/2009 | Nissl |
| 2009/0177266 A1 | 7/2009 | Powell et al. |
| 2009/0177277 A1 | 7/2009 | Milo |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0248148 A1 | 10/2009 | Shaolian et al. |
| 2009/0254103 A1 | 10/2009 | Deustch |
| 2009/0259306 A1 | 10/2009 | Rowe |
| 2009/0259307 A1 | 10/2009 | Gross et al. |
| 2009/0264859 A1 | 10/2009 | Mas |
| 2009/0264994 A1 | 10/2009 | Saadat |
| 2009/0264995 A1 | 10/2009 | Subramanian |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0287304 A1 | 11/2009 | Dahlgren et al. |
| 2009/0299409 A1 | 12/2009 | Coe et al. |
| 2009/0299449 A1 | 12/2009 | Styrc |
| 2009/0306768 A1 | 12/2009 | Quardi |
| 2009/0319037 A1 | 12/2009 | Rowe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0022823 A1 | 1/2010 | Goldfarb et al. |
| 2010/0023117 A1 | 1/2010 | Yoganathan et al. |
| 2010/0023118 A1 | 1/2010 | Medlock et al. |
| 2010/0023120 A1 | 1/2010 | Holecek et al. |
| 2010/0030014 A1 | 2/2010 | Ferrazzi |
| 2010/0036479 A1 | 2/2010 | Hill et al. |
| 2010/0036484 A1 | 2/2010 | Hariton et al. |
| 2010/0042147 A1 | 2/2010 | Janovsky et al. |
| 2010/0049313 A1 | 2/2010 | Alon et al. |
| 2010/0063542 A1 | 3/2010 | Van der Burg et al. |
| 2010/0063550 A1 | 3/2010 | Felix et al. |
| 2010/0063586 A1 | 3/2010 | Hasenkam et al. |
| 2010/0069852 A1 | 3/2010 | Kelley |
| 2010/0076499 A1 | 3/2010 | McNamara et al. |
| 2010/0076548 A1 | 3/2010 | Konno |
| 2010/0082094 A1 | 4/2010 | Quadri et al. |
| 2010/0094248 A1 | 4/2010 | Nguyen et al. |
| 2010/0100167 A1 | 4/2010 | Bortlein et al. |
| 2010/0114180 A1 | 5/2010 | Rock |
| 2010/0114299 A1 | 5/2010 | Ben-Muvhar et al. |
| 2010/0121349 A1 | 5/2010 | Meier |
| 2010/0130992 A1 | 5/2010 | Machold et al. |
| 2010/0131054 A1 | 5/2010 | Tuval et al. |
| 2010/0137979 A1 | 6/2010 | Tuval et al. |
| 2010/0152845 A1 | 6/2010 | Bloom et al. |
| 2010/0160958 A1 | 6/2010 | Clark |
| 2010/0161036 A1 | 6/2010 | Pintor et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0174363 A1 | 7/2010 | Castro |
| 2010/0179574 A1 | 7/2010 | Longoria et al. |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1 | 7/2010 | Braido et al. |
| 2010/0198347 A1 | 8/2010 | Zakay et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234935 A1 | 9/2010 | Bashiri et al. |
| 2010/0234940 A1 | 9/2010 | Dolan |
| 2010/0249908 A1 | 9/2010 | Chau et al. |
| 2010/0249915 A1 | 9/2010 | Zhang |
| 2010/0249917 A1 | 9/2010 | Zhang |
| 2010/0249920 A1 | 9/2010 | Bolling et al. |
| 2010/0256737 A1 | 10/2010 | Pollock et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0280606 A1 | 11/2010 | Naor |
| 2010/0286628 A1 | 11/2010 | Gross |
| 2010/0286767 A1 | 11/2010 | Zipory et al. |
| 2010/0305475 A1 | 12/2010 | Hinchliffe et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004210 A1 | 1/2011 | Johnson et al. |
| 2011/0004227 A1 | 1/2011 | Goldfarb et al. |
| 2011/0004296 A1 | 1/2011 | Lutter et al. |
| 2011/0004298 A1 | 1/2011 | Lee et al. |
| 2011/0004299 A1 | 1/2011 | Navia et al. |
| 2011/0011917 A1 | 1/2011 | Loulmet |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0026208 A1 | 2/2011 | Otsuro et al. |
| 2011/0029066 A1 | 2/2011 | Gilad et al. |
| 2011/0029067 A1 | 2/2011 | Mcguckin, Jr. et al. |
| 2011/0029072 A1 | 2/2011 | Gabbay |
| 2011/0035000 A1 | 2/2011 | Nieminen et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066231 A1 | 3/2011 | Cartledge et al. |
| 2011/0066233 A1 | 3/2011 | Thornton et al. |
| 2011/0067770 A1 | 3/2011 | Pederson et al. |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087146 A1 | 4/2011 | Ryan et al. |
| 2011/0087322 A1 | 4/2011 | Letac et al. |
| 2011/0093002 A1 | 4/2011 | Rucker et al. |
| 2011/0093063 A1 | 4/2011 | Schreck |
| 2011/0098525 A1 | 4/2011 | Kermode et al. |
| 2011/0106245 A1 | 5/2011 | Miller et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0113768 A1 | 5/2011 | Bauer et al. |
| 2011/0118830 A1 | 5/2011 | Liddicoat et al. |
| 2011/0118832 A1 | 5/2011 | Punjabi |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144703 A1 | 6/2011 | Krause et al. |
| 2011/0144742 A1 | 6/2011 | Madrid et al. |
| 2011/0166636 A1 | 7/2011 | Rowe |
| 2011/0166649 A1 | 7/2011 | Gross et al. |
| 2011/0172784 A1 | 7/2011 | Richter |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0202130 A1 | 8/2011 | Cartledge et al. |
| 2011/0208283 A1 | 8/2011 | Rust |
| 2011/0208293 A1 | 8/2011 | Tabor |
| 2011/0208298 A1 | 8/2011 | Tuval et al. |

(56) References Cited

U.S. PATENT DOCUMENTS

| | | |
|---|---|---|
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bodluc et al. |
| 2011/0238094 A1 | 9/2011 | Thomas et al. |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257433 A1 | 10/2011 | Walker |
| 2011/0257633 A1 | 10/2011 | Cartledge et al. |
| 2011/0257721 A1 | 10/2011 | Tabor |
| 2011/0257728 A1 | 10/2011 | Kuehn |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0276062 A1 | 11/2011 | Bolduc |
| 2011/0282361 A1 | 11/2011 | Miller et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288435 A1 | 11/2011 | Christy et al. |
| 2011/0288632 A1 | 11/2011 | White |
| 2011/0288634 A1 | 11/2011 | Tuval et al. |
| 2011/0288635 A1 | 11/2011 | Miller et al. |
| 2011/0295354 A1 | 12/2011 | Bueche et al. |
| 2011/0295363 A1 | 12/2011 | Girard et al. |
| 2011/0301498 A1 | 12/2011 | Maenhout et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022557 A1 | 1/2012 | Cabiri et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035703 A1 | 2/2012 | Lutter et al. |
| 2012/0035712 A1 | 2/2012 | Maisano et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053680 A1 | 3/2012 | Bolling et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078355 A1 | 3/2012 | Zipory et al. |
| 2012/0078357 A1 | 3/2012 | Conklin |
| 2012/0078359 A1 | 3/2012 | Li et al. |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089022 A1 | 4/2012 | House et al. |
| 2012/0089223 A1 | 4/2012 | Nguyen et al. |
| 2012/0095552 A1 | 4/2012 | Spence et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0109155 A1 | 5/2012 | Robinson et al. |
| 2012/0123511 A1 | 5/2012 | Brown |
| 2012/0123529 A1 | 5/2012 | Levi et al. |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0136436 A1 | 5/2012 | Cabiri et al. |
| 2012/0143323 A1 | 6/2012 | Hasenkam et al. |
| 2012/0150218 A1 | 6/2012 | Sandgren et al. |
| 2012/0150290 A1 | 6/2012 | Gabbay |
| 2012/0158021 A1 | 6/2012 | Morrill |
| 2012/0165915 A1 | 6/2012 | Melsheimer et al. |
| 2012/0165930 A1 | 6/2012 | Gifford, III et al. |
| 2012/0179086 A1 | 7/2012 | Shank et al. |
| 2012/0179244 A1 | 7/2012 | Schankereli et al. |
| 2012/0191182 A1 | 7/2012 | Hauser et al. |
| 2012/0197292 A1 | 8/2012 | Chin-Chen et al. |
| 2012/0197388 A1 | 8/2012 | Khairkhahan et al. |
| 2012/0215303 A1 | 8/2012 | Quadri et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0277845 A1 | 11/2012 | Bowe |
| 2012/0283757 A1 | 11/2012 | Miller et al. |
| 2012/0283824 A1 | 11/2012 | Lutter et al. |
| 2012/0290062 A1 | 11/2012 | McNamara et al. |
| 2012/0296349 A1 | 11/2012 | Smith et al. |
| 2012/0296360 A1 | 11/2012 | Norris et al. |
| 2012/0296417 A1 | 11/2012 | Hill et al. |
| 2012/0296418 A1 | 11/2012 | Bonyuet et al. |
| 2012/0296419 A1 | 11/2012 | Richardson |
| 2012/0300063 A1 | 11/2012 | Majkrzak et al. |
| 2012/0123531 A1 | 12/2012 | Tsukashima et al. |
| 2012/0310328 A1 | 12/2012 | Olson et al. |
| 2012/0310330 A1 | 12/2012 | Buchbinder et al. |
| 2012/0323313 A1 | 12/2012 | Seguin |
| 2012/0323316 A1 | 12/2012 | Chau et al. |
| 2012/0330408 A1 | 12/2012 | Hillukka et al. |
| 2012/0330410 A1 | 12/2012 | Hammer et al. |
| 2012/0330411 A1 | 12/2012 | Gross et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0023758 A1 | 1/2013 | Fabro |
| 2013/0030519 A1 | 1/2013 | Tran et al. |
| 2013/0030522 A1 | 1/2013 | Rowe et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai et al. |
| 2013/0066342 A1 | 3/2013 | Dell et al. |

(56) References Cited

U.S. PATENT DOCUMENTS

| | | |
|---|---|---|
| 2013/0079872 A1 | 3/2013 | Gallagher |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0116779 A1 | 5/2013 | Weber |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190857 A1 | 7/2013 | Mitra et al. |
| 2013/0190861 A1 | 7/2013 | Chau et al. |
| 2013/0190863 A1 | 7/2013 | Call et al. |
| 2013/0190866 A1 | 7/2013 | Zipory et al. |
| 2013/0197632 A1 | 8/2013 | Kovach et al. |
| 2013/0204361 A1 | 8/2013 | Adams et al. |
| 2013/0211501 A1 | 8/2013 | Buckley et al. |
| 2013/0211508 A1 | 8/2013 | Lane et al. |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0245742 A1 | 9/2013 | Norris |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0289718 A1 | 10/2013 | Tsukashima et al. |
| 2013/0289740 A1 | 10/2013 | Liddy et al. |
| 2013/0297013 A1 | 11/2013 | Klima et al. |
| 2013/0304093 A1 | 11/2013 | Serina et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0325118 A1 | 12/2013 | Cartledge |
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018911 A1 | 1/2014 | Zhou et al. |
| 2014/0018914 A1 | 1/2014 | Zipory et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0099726 A1 | 4/2014 | Heller |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135799 A1 | 5/2014 | Henderson |
| 2014/0135894 A1 | 5/2014 | Norris et al. |
| 2014/0135895 A1 | 5/2014 | Andress et al. |
| 2014/0142619 A1 | 5/2014 | Serina et al. |
| 2014/0142681 A1 | 5/2014 | Norris |
| 2014/0142688 A1 | 5/2014 | Duffy et al. |
| 2014/0142695 A1 | 5/2014 | Gross et al. |
| 2014/0148849 A1 | 5/2014 | Serina et al. |
| 2014/0148891 A1 | 5/2014 | Johnson |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188108 A1 | 7/2014 | Goodine et al. |
| 2014/0188140 A1 | 7/2014 | Meier et al. |
| 2014/0188210 A1 | 7/2014 | Beard et al. |
| 2014/0188215 A1 | 7/2014 | Hlavka et al. |
| 2014/0188221 A1 | 7/2014 | Chung et al. |
| 2014/0194970 A1 | 7/2014 | Chobotov |
| 2014/0194976 A1 | 7/2014 | Starksen et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214157 A1 | 7/2014 | Börtlein et al. |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0275757 A1 | 9/2014 | Goodwin et al. |
| 2014/0276648 A1 | 9/2014 | Hammer et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0329225 A1 | 11/2014 | Morin |
| 2014/0331475 A1 | 11/2014 | Duffy et al. |
| 2014/0336744 A1 | 11/2014 | Tani et al. |
| 2014/0343668 A1 | 11/2014 | Zipory et al. |
| 2014/0343670 A1 | 11/2014 | Bakis et al. |
| 2014/0350662 A1 | 11/2014 | Vaturi |
| 2014/0350670 A1 | 11/2014 | Keränen |
| 2014/0358222 A1 | 12/2014 | Gorman, III et al. |
| 2014/0358224 A1 | 12/2014 | Tegels et al. |
| 2014/0378331 A1 | 12/2014 | Morin |
| 2014/0379006 A1 | 12/2014 | Sutherland et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0012087 A1 | 1/2015 | Miller et al. |
| 2015/0018940 A1 | 1/2015 | Quill et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0051697 A1 | 2/2015 | Spence et al. |
| 2015/0081014 A1 | 3/2015 | Gross et al. |
| 2015/0094802 A1 | 4/2015 | Buchbinder et al. |
| 2015/0105855 A1 | 4/2015 | Cabiri et al. |
| 2015/0119970 A1 | 4/2015 | Nakayama et al. |
| 2015/0127097 A1 | 5/2015 | Neumann et al. |

(56) References Cited

U.S. PATENT DOCUMENTS

| | | |
|---|---|---|
| 2015/0142100 A1 | 5/2015 | Morriss et al. |
| 2015/0142103 A1 | 5/2015 | Vidlund |
| 2015/0148894 A1 | 5/2015 | Damm et al. |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0182336 A1 | 7/2015 | Zipory et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0230924 A1 | 8/2015 | Miller et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1 | 10/2015 | Racchini et al. |
| 2015/0272734 A1 | 10/2015 | Sheps et al. |
| 2015/0282964 A1 | 10/2015 | Beard et al. |
| 2015/0305903 A1 | 10/2015 | Kitaoka |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0175095 A1 | 6/2016 | Dienno et al. |
| 2016/0200773 A1 | 7/2016 | Morin |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0245802 A1 | 8/2016 | Morin et al. |
| 2016/0258939 A1 | 9/2016 | Morin et al. |
| 2016/0266089 A1 | 9/2016 | Morin et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0074855 A1 | 3/2017 | Morin et al. |
| 2017/0100236 A1 | 4/2017 | Robertson et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0234850 A1 | 8/2017 | Morin |
| 2017/0239048 A1 | 8/2017 | Goldfarb et al. |
| 2017/0252159 A1 | 9/2017 | Hacohen et al. |
| 2017/0266003 A1 | 9/2017 | Hammer et al. |
| 2017/0333183 A1 | 11/2017 | Backus |
| 2017/0333187 A1 | 11/2017 | Hariton et al. |
| 2017/0349940 A1 | 12/2017 | Morin et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0023114 A1 | 1/2018 | Morin et al. |
| 2018/0023115 A1 | 1/2018 | Morin et al. |
| 2018/0028215 A1 | 2/2018 | Cohen |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153696 A1 | 6/2018 | Albitov et al. |
| 2018/0161159 A1 | 6/2018 | Lee et al. |
| 2018/0177593 A1 | 6/2018 | Hariton et al. |
| 2018/0177594 A1 | 6/2018 | Patel et al. |
| 2018/0185148 A1 | 7/2018 | Hariton et al. |
| 2018/0206983 A1 | 7/2018 | Noe et al. |
| 2018/0214263 A1 | 8/2018 | Rolando et al. |
| 2018/0243086 A1 | 8/2018 | Barbarino et al. |
| 2018/0250126 A1 | 9/2018 | O'connor et al. |
| 2018/0250147 A1 | 9/2018 | Syed |
| 2018/0271654 A1 | 9/2018 | Hariton et al. |
| 2018/0280136 A1 | 10/2018 | Hariton et al. |
| 2018/0296333 A1 | 10/2018 | Dixon et al. |
| 2018/0296336 A1 | 10/2018 | Cooper et al. |
| 2018/0296341 A1 | 10/2018 | Noe et al. |
| 2018/0325671 A1 | 11/2018 | Abunassar et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2018/0360457 A1 | 12/2018 | Ellis et al. |
| 2019/0000613 A1 | 1/2019 | Delgado et al. |
| 2019/0015200 A1 | 1/2019 | Delgado et al. |
| 2019/0021852 A1 | 1/2019 | Delgado et al. |
| 2019/0021857 A1 | 1/2019 | Hacohen et al. |
| 2019/0038404 A1 | 2/2019 | Iamberger et al. |
| 2019/0038405 A1 | 2/2019 | Iamberger et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0069998 A1 | 3/2019 | Hacohen |
| 2019/0083248 A1 | 3/2019 | Hariton et al. |
| 2019/0083249 A1 | 3/2019 | Hariton et al. |
| 2019/0083261 A1 | 3/2019 | Perszyk et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0192295 A1 | 6/2019 | Spence et al. |

(56) References Cited

U.S. PATENT DOCUMENTS

| | | |
|---|---|---|
| 2019/0216602 A1 | 7/2019 | Lozonschi |
| 2019/0231525 A1 | 8/2019 | Hariton et al. |
| 2019/0240010 A1 | 8/2019 | Hacohen |
| 2019/0336280 A1 | 11/2019 | Naor |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000449 A1 | 1/2020 | Goldfarb et al. |
| 2020/0000579 A1 | 1/2020 | Manash et al. |
| 2020/0000580 A1 | 1/2020 | Hacohen |
| 2020/0015964 A1 | 1/2020 | Noe et al. |
| 2020/0030098 A1 | 1/2020 | Delgado et al. |
| 2020/0038181 A1 | 2/2020 | Hariton et al. |
| 2020/0046496 A1 | 2/2020 | Hammer et al. |
| 2020/0054335 A1 | 2/2020 | Hernandez et al. |
| 2020/0060818 A1 | 2/2020 | Geist et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0138567 A1 | 5/2020 | Marr et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0205969 A1 | 7/2020 | Hacohen |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0306037 A1 | 10/2020 | Siegel et al. |
| 2020/0315786 A1 | 10/2020 | Metchik et al. |
| 2020/0337842 A1 | 10/2020 | Metchik et al. |
| 2020/0360139 A1 | 11/2020 | Hammer et al. |
| 2020/0390548 A1 | 12/2020 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0259835 A1 | 8/2021 | Tyler, II et al. |
| 2022/0000612 A1 | 1/2022 | Hacohen |

FOREIGN PATENT DOCUMENTS

| | | |
|---|---|---|
| CN | 101653365 | 2/2010 |
| CN | 103974674 | 8/2014 |
| CN | 103997990 | 8/2014 |
| CN | 105324091 | 2/2016 |
| EP | 0170262 | 2/1986 |
| EP | 06/14342 | 9/1994 |
| EP | 10/06905 | 6/2000 |
| EP | 0954257 | 8/2000 |
| EP | 1258437 | 11/2002 |
| EP | 1264582 | 12/2002 |
| EP | 0871417 | 10/2003 |
| EP | 1266641 | 10/2004 |
| EP | 1034753 | 2/2005 |
| EP | 1258232 | 1/2006 |
| EP | 1637092 | 3/2006 |
| EP | 1990014 | 11/2008 |
| EP | 1562522 | 12/2008 |
| EP | 1420723 | 1/2009 |
| EP | 1903991 | 9/2009 |
| EP | 1418865 | 10/2009 |
| EP | 2119399 | 11/2009 |
| EP | 1531762 | 4/2010 |
| EP | 1450733 | 2/2011 |
| EP | 2446915 A1 | 5/2012 |
| EP | 2088965 | 11/2012 |
| EP | 1768630 | 1/2015 |
| EP | 1861045 | 3/2015 |
| EP | 1465555 | 5/2015 |
| EP | 2349124 | 10/2018 |
| EP | 2739214 | 10/2018 |
| EP | 3417813 | 12/2018 |
| EP | 3583922 | 12/2019 |
| EP | 3270825 | 4/2020 |
| EP | 2485795 | 9/2020 |
| IL | 223448 | 12/2012 |
| JP | S53152790 | 12/1978 |
| KR | 20010046894 | 6/2001 |
| OA | 2011/144351 | 11/2011 |
| WO | 92/05093 | 4/1992 |
| WO | 93/10714 | 6/1993 |
| WO | 96/39963 | 12/1996 |
| WO | 96/40344 | 12/1996 |
| WO | 97/01369 | 1/1997 |
| WO | 98/46149 | 10/1998 |
| WO | 1998/043557 | 10/1998 |
| WO | 1999/030647 | 6/1999 |
| WO | 00/22981 | 4/2000 |
| WO | 2000-047139 | 8/2000 |
| WO | 01/26586 | 4/2001 |
| WO | 01/56457 | 8/2001 |
| WO | 2001-062189 | 8/2001 |
| WO | 01/82832 | 11/2001 |
| WO | 02/085250 | 10/2002 |
| WO | 02/085251 | 10/2002 |
| WO | 02/085252 | 10/2002 |
| WO | 2003/020179 | 3/2003 |
| WO | 2003/028558 | 4/2003 |
| WO | 03/047467 | 6/2003 |
| WO | 2003/049647 | 6/2003 |
| WO | 2003/105667 | 12/2003 |
| WO | 2004/028399 | 4/2004 |
| WO | 04/103434 | 12/2004 |
| WO | 2004/108191 | 12/2004 |
| WO | 05/021063 | 3/2005 |
| WO | 05/046488 | 5/2005 |
| WO | 2005/062931 | 7/2005 |
| WO | 2005/107650 | 11/2005 |
| WO | 2006/007389 | 1/2006 |
| WO | 2006/007401 | 1/2006 |
| WO | 06/012013 | 2/2006 |
| WO | 06/012038 | 2/2006 |
| WO | 06/054930 | 5/2006 |
| WO | 2006/065212 | 6/2006 |
| WO | 2006/070372 | 7/2006 |
| WO | 06/086434 | 8/2006 |
| WO | 2006/089236 | 8/2006 |
| WO | 2006/091163 | 8/2006 |
| WO | 06/097931 | 9/2006 |
| WO | 06/105084 | 10/2006 |
| WO | 06/116558 | 11/2006 |
| WO | 2006/128193 | 11/2006 |
| WO | 07/011799 | 1/2007 |
| WO | 2007/030063 | 3/2007 |
| WO | 2007/047488 | 4/2007 |
| WO | 2007/059252 | 5/2007 |
| WO | 07/121314 | 10/2007 |
| WO | 07/136783 | 11/2007 |
| WO | 07/136981 | 11/2007 |
| WO | 08/013915 | 1/2008 |
| WO | 2008/014144 | 1/2008 |
| WO | 2008/029296 | 3/2008 |
| WO | 2008/031103 | 3/2008 |
| WO | 2008/058940 | 5/2008 |
| WO | 08/068756 | 6/2008 |
| WO | 2008/070797 | 6/2008 |
| WO | 2008/103722 | 8/2008 |
| WO | 2009/026563 | 2/2009 |
| WO | 09/033469 | 3/2009 |
| WO | 09/053497 | 4/2009 |
| WO | 2009/080801 | 7/2009 |
| WO | 2009/091509 | 7/2009 |
| WO | 2009/160631 | 10/2009 |
| WO | 10/004546 | 1/2010 |
| WO | 2010/000454 | 1/2010 |
| WO | 2010/006627 | 1/2010 |
| WO | 2010/006905 | 1/2010 |
| WO | 2010/027485 | 3/2010 |
| WO | 2010/037141 | 4/2010 |
| WO | 2010/044851 | 4/2010 |

(56) References Cited

FOREIGN PATENT DOCUMENTS

| | | |
|---|---|---|
| WO | 2010/045297 | 4/2010 |
| WO | 2010/057262 | 5/2010 |
| WO | 2010/073246 | 7/2010 |
| WO | 2010/081033 | 7/2010 |
| WO | 2010/085649 | 7/2010 |
| WO | 2010/121076 | 10/2010 |
| WO | 2010/128502 | 11/2010 |
| WO | 2010/128503 | 11/2010 |
| WO | 2010/150178 | 12/2010 |
| WO | 2011/025972 | 3/2011 |
| WO | 2011/051942 | 5/2011 |
| WO | 2011/067770 | 6/2011 |
| WO | 2011/069048 | 6/2011 |
| WO | 2011/089401 | 7/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/148374 | 12/2011 |
| WO | 2011/154942 | 12/2011 |
| WO | 2012/011108 | 1/2012 |
| WO | 2012/014201 | 2/2012 |
| WO | 2012/024428 | 2/2012 |
| WO | 2012/036740 | 3/2012 |
| WO | 2012/048035 | 4/2012 |
| WO | 2012/068541 | 5/2012 |
| WO | 2012/127309 | 9/2012 |
| WO | 2012/176195 | 12/2012 |
| WO | 2012/177942 | 12/2012 |
| WO | 2013/021374 | 2/2013 |
| WO | 2013/021375 | 2/2013 |
| WO | 2013/021384 | 2/2013 |
| WO | 2013/059747 | 4/2013 |
| WO | 2013/069019 | 5/2013 |
| WO | 2013/072496 | 5/2013 |
| WO | 2013/078497 | 6/2013 |
| WO | 2013/088327 | 6/2013 |
| WO | 2013/114214 | 8/2013 |
| WO | 2013/128436 | 9/2013 |
| WO | 2013/175468 | 11/2013 |
| WO | 2014/022124 | 2/2014 |
| WO | 2014/064694 | 5/2014 |
| WO | 2014/064695 | 5/2014 |
| WO | 2014/076696 | 5/2014 |
| WO | 2014/087402 | 6/2014 |
| WO | 2014/115149 | 7/2014 |
| WO | 2014/121280 A2 | 8/2014 |
| WO | 2014/144937 | 9/2014 |
| WO | 2014/145338 | 9/2014 |
| WO | 2014/164364 | 10/2014 |
| WO | 2014/194178 | 12/2014 |
| WO | 2014/195786 | 12/2014 |
| WO | 2015/059699 | 4/2015 |
| WO | 2015/173794 | 11/2015 |
| WO | 2016/016899 | 2/2016 |
| WO | 2016/093877 | 6/2016 |
| WO | 2016/125160 | 8/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |
| WO | 2019/027507 | 2/2019 |
| WO | 2019/030753 | 2/2019 |
| WO | 2019/077595 | 4/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/167677 | 8/2020 |
| WO | 2021/156866 A1 | 8/2021 |
| WO | 2021/186424 A1 | 9/2021 |

OTHER PUBLICATIONS

IPR2021-01051 Institution decision dated Dec. 10, 2021.
Notice of Allowance dated Dec. 7, 2021, which issued during the prosecution of U.S. Appl. No. 17/394,807.
Notice of Allowance dated Dec. 6, 2021, which issued during the prosecution of U.S. Appl. No. 16/738,516.
Notice of Allowance dated Dec. 29, 2021, which issued during the prosecution of U.S. Appl. No. 17/210,183.
IPR2021-00383 Petitioners' Reply to Patent Owner's Response dated Jan. 5, 2022.
IPR2021-00383 Petitioners' Opposition to Patent Owner's Contingent Motion to Amend dated Jan. 5, 2022.
An Office Action dated Sep. 22, 2021, which issued during the prosecution of European Patent Application No. 20714289.4.
Summary of Examination Notice dated Jan. 6, 2022, which issued during the prosecution of Chinese Patent Application No. 201880064313.X.
An Office Action dated Jan. 12, 2022, which issued during the prosecution of U.S. Appl. No. 17/101,787.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.
Notice of Allowance dated May 17, 2021, which issued during the prosecution of U.S. Appl. No. 16/138,129.
Notice of Allowance dated Jun. 4, 2021, which issued during the prosecution of U.S. Appl. No. 16/802,353.
An Office Action dated May 12, 2021, which issued during the prosecution of Canadian Patent Application No. 2,973,940.
Petition for Inter Partes Review of U.S. Pat. No. 10,702,385—dated Jun. 4, 2021.
Declaration of Ivan Vesely, Ph.D. In Support of Petition for Inter Partes Review of U.S. Pat. No. 10,702,385—dated Jun. 4, 2021.
An Office Action dated Sep. 9, 2021, which issued during the prosecution of U.S. Appl. No. 16/768,909.
An Office Action dated Sep. 15, 2021, which issued during the prosecution of U.S. Appl. No. 16/135,599.
An Office Action dated Oct. 14, 2021, which issued during the prosecution of U.S. Appl. No. 16/680,739.
An Office Action dated Oct. 21, 2021, which issued during the prosecution of U.S. Appl. No. 17/335,845.
European Search Report dated Oct. 11, 2021 which issued during the prosecution of Applicant's European App No. 21176010.3.

(56) References Cited

OTHER PUBLICATIONS

Fann, James I., et al. "Beating heart catheter-based edge-to-edge mitral valve procedure in a porcine model: efficacy and healing response." Circulation 110.8 (2004): 988-993.
Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.
IPR2021-00383 Patent Owner's Contingent Motion To Amend Under 37 C.F.R. §42.121 dated Oct. 13, 2021.
IPR2021-00383 Patent Owner's Response Pursuant To 37 C.F.R. § 42.120 dated Oct. 13, 2021.
IPR2021-00383 Second Declaration of Dr. Michael Sacks dated Oct. 13, 2021.
An Office Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
IPR2021-00383 Deposition of DR. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
IPR2021-00383 Decision Final Written Decision dated Jul. 18, 2022.
IPR2021-01051 Preliminary Guidance Patent Owner's Motion To Amend dated Jun. 24, 2022.
Ex Parte Quayle dated May 2, 2022, which issued during the prosecution of U.S. Appl. No. 16/879,952.
An International Search Report and a Written Opinion both dated May 3, 2022, which issued during the prosecution of Applicant's PCT/IL2021/051433.
An Office Action together with an English Summary dated May 7, 2022 which issued during the prosecution of Chinese Patent Application No. 201880058940.2.
Notice of Allowance dated May 4, 2022, which issued during the prosecution of U.S. Appl. No. 16/680,739.
An Office Action dated Jun. 28, 2022, which issued during the prosecution of U.S. Appl. No. 16/135,969.
An Office Action dated Jul. 8, 2022, which issued during the prosecution of U.S. Appl. No. 16/144,054.
An Office Action dated Jan. 26, 2022, which issued during the prosecution of U.S. Appl. No. 16/888,210.
Notice of Allowance dated Jan. 31, 2022, which issued during the prosecution of U.S. Appl. No. 17/479,418.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
An Office Action dated Apr. 11, 2022, which issued during the prosecution of U.S. Appl. No. 17/473,472.
IPR2021-00383 Preliminary Guidance dated Jan. 31, 2022.
European Search Report dated Jun 10, 2021 which issued during the prosecution of Applicant's European App No. 21157988.3.
An Invitation to pay additional fees dated May 19, 2021, which issued during the prosecution of Applicant's PCT/IL2021/050132.
An International Search Report and a Written Opinion both dated Jul. 12, 2021, which issued during the prosecution of Applicant's PCT/IL2021/050132.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*)
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021(*Edwards Lifesciences* vs. *Cardiovalve*).
An Office Action dated Aug. 18, 2021, which issued during the prosecution of U.S. Appl. No 17/210,183.
Institution decision dated Jul. 20, 2021(*Edwards Lifesciences* vs. *Cardiovalve*)
An Office Action dated Jul. 27, 2022, which issued during the prosecution of U.S. Appl. No. 16/881,350.
An Office Action dated Sep. 21, 2022, which issued during the prosecution of U.S. Appl. No. 16/776,581.
An Office Action dated Jul. 20, 2022, which issued during the prosecution of U.S. Appl. No. 17/101,787.
An Office Action dated Sep. 16, 2022, which issued during the prosecution of U.S. Appl. No. 16/135,466.
An Office Action dated Aug. 1, 2022, which issued during the prosecution of European Patent Application No. 18826823.9.
European Search Report dated Sep. 6, 2022 which issued during the prosecution of Applicant's European App No. 22161862.2.
IPR2021-01051 Petitioners' Reply To Preliminary Guidance dated Aug. 2, 2022.
IPR2021-01051 Patent Owner's Sur-Reply To Petitioners' Reply To Preliminary Guidance dated Aug. 23, 2022.
An Office Action dated Aug. 5, 2022, which issued during the prosecution of U.S. Appl. No. 16/760,147.
An Office Action dated Sep. 8, 2022, which issued during the prosecution of U.S. Appl. No. 16/896,858.
An Office Action dated Nov. 23, 2012, which issued during the prosecution of U.S. Appl. No. 13/033,852.
An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "RING plus STRING: Papillary muscle repositioning as an adjunctive repair technique for ischemic mitral regurgitation," J Thorac Cardiovasc Surg 133:247-9, Jan. 2007.
Langer F et al., "RING+STRING: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.

(56) References Cited

OTHER PUBLICATIONS

U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/031,852.
An Office Action dated Sep. 19, 2014, which issued during the prosecution of U.S. Appl. No. 13/044,694.
An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/411,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/411,814.
An Office Action dated Aug. 2, 2013, which issued during the prosecution of U.S. Appl. No. 13/031,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/ 044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/411,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/761,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015: which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of US Design U.S. Appl. No. 29/635,658.
An Office Action dated Jun. 28, 2018, which issued during the prosecution of US Design U.S. Appl. No. 29/635,661.

(56) References Cited

OTHER PUBLICATIONS

Georg Lutter, MD, et al; "Percutaneous Valve Replacement: Current State and Future Prospects", The Annals of Thoracic Surgery ; vol. 78, pp. 2199-2206; Dec. 2004.
An Office Action dated Jun. 6, 2018, which issued during the prosecution of UK Patent Application No. 1720803.4.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Appl. No. 1800399.6.
An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/211,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13, 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul. 1, 2016, which issued during the prosecution of U.S. Appl. No. 14/442,541.
An Office Action dated Mar. 25, 2019, which issued during the prosecution of European Patent Application No. 14710060.6.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25, 2019, which issued during the prosecution of Applicant's PCT/IL2019/050142.
An International Preliminary Report on Patentability dated Feb. 12, 2019, which issued during the prosecution of Applicant's PCT/IL2017/050873.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An International Preliminary Report on Patentability dated Feb. 4, 2020, which issued during the prosecution of Applicant's PCT/IL2018/050725.
An International Search Report and a Written Opinion both dated Jan. 25, 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Aug. 1, 2019, which issued during the prosecution of U.S. Appl. No. 15/668,559.
An Office Action dated Jun. 19, 2019, which issued during the prosecution of U.S. Appl. No. 15/682,789.

(56) References Cited

OTHER PUBLICATIONS

Notice of Allowance dated Jan. 13, 2020, which issued during the prosecution of U.S. Appl. No. 15/956,956.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
U.S. Appl. No. 62/560,384, filed Sep. 19, 2017.
U.S. Appl. No. 62/112,343, filed Feb. 5, 2015.
An International Preliminary Report on Patentability dated Feb. 11, 2020, which issued during the prosecution of Applicant's PCT/IL2018/050869.
An International Preliminary Report on Patentability dated Oct. 20, 2020, which issued during the prosecution of Applicant's PCT/IL2019/050142.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
Notice of Allowance dated Apr. 24, 2019, which issued during the prosecution of U.S. Appl. No. 16/045,059.
An Office Action dated Jan. 14, 2020, which issued during the prosecution of U.S. Appl. No. 16/284,331.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Nov. 26, 2019, which issued during the prosecution of U.S. Appl. No. 16/532,945.
Notice of Allowance dated Aug. 19, 2020, which issued during the prosecution of U.S. Appl. No. 16/637,166.
Notice of Allowance dated Jul. 27, 2020, which issued during the prosecution of U.S. Appl. No. 16/637,166.
Notice of Allowance dated Jun. 23, 2020, which issued during the prosecution of U.S. Appl. No. 16/637,166.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dq=%20%22Edwards%20SAPIEN%22&lr&pg=PA20#y=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100.
An Office Action dated Aug. 23, 2019, which issued during the prosecution of U.S. Appl. No. 15/600,190.
Symetis S.A.: "ACURATE neo™ Aortic Bioprosthesis for Implantation using the ACURATE neo™ TA Transapical Delivery System in Patients with Severe Aortic Stenosis," Clinical Investigation Plan, Protocol No. 2015-01, Vs. No. 2, 2015:1-76, Thomas Walther.
Notice of Allowance dated Sep. 10, 2020, which issued during the prosecution of U.S. Appl. No. 15/600,190.
Notice of Allowance dated Sep. 10, 2020, which issued during the prosecution of U.S. Appl. No. 16/324,339.
Notice of Allowance dated Oct. 19, 2020, which issued during the prosecution of U.S. Appl. No. 16/324,339.
Notice of Allowance dated Sep. 21, 2020, which issued during the prosecution of U.S. Appl. No. 16/269,328.
Notice of Allowance dated Oct. 28, 2020, which issued during the prosecution of U.S. Appl. No. 16/269,328.
Notice of Allowance dated Jan. 16, 2020, which issued during the prosecution of U.S. Appl. No. 15/872,501.
An Office Action dated May 11, 2020, which issued during the prosecution of U.S. Appl. No. 16/811,732.
An Office Action dated Sep. 24, 2020, which issued during the prosecution of U.S. Appl. No. 16/811,732.
Notice of Allowance dated Mar. 29, 2017, which issued during the prosecution of U.S. Appl. No. 14/161,921.
Agarwal et al. International Cardiology Perspective Functional Tricuspid Regurgitation, Circ Cardiovasc Interv 2009;2;2;565-573 (2009).
Alfieri et al., "An effective technique to correct anterior mitral leafet prolapse," J Card 14(6):468-470. (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Alfieri et al. "Novel Suture Device for Beating-Heart Mitral Leaflet Approximation", Ann Thorac Surg. 2002, 74:1488-1493.
Alfieri et al., "The edge to edge technique," The European Association for Cardio-Thoracic Surgery $14^{th}$ Annual Meeting Oct. 7-11, Book of Procees. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Brennan, Jennifer, 510(k) Summary of safety and effectiveness, Jan. 2008.
Dictionary.com definition of "lock", Jul. 29, 2013.
Dang NC et al. "Simplified Placement of Multiple Artificial Mitral Valve Chords," The Heart Surgery Forum #2005-1005. 8 (3) (2005).
Maisano, The double-orifice technique as a standardized approach to treat mitral . . . , European Journal of Cardio-thoracic Surgery 17 (2000) 201-205.
"Two dimensional real-time ultrasonic imaging of the heart and great vessels", Mayo Clin Proc. vol. 53:271-303, 1978.
Odell JA et al., "Early Results o4yf a Simplified Method of Mitral Valve Annuloplasty," Circulation 92: 150-154 (1995).
O'Reilly S et al., "Heart valve surgery pushes the envelope," Medtech Insight 8(3): 73, 99-108 (2006).
Swain CP et al., "An endoscopically deliverable tissue-transfixing device for securing biosensors in the gastrointestinal tract," Gastrointestinal Endoscopy 40(6): 730-734 (1994).

(56) References Cited

OTHER PUBLICATIONS

An Invitation to pay additional fees dated Jan. 31, 2014, which issued during the prosecution of Applicant's PCT/IL2013/050860.
U.S. Appl. No. 62/030,715, filed Jul. 30, 2014.
U.S. Appl. No. 62/139,854, filed Mar. 30, 2015.
U.S. Appl. No. 61/312,412, filed Mar. 10, 2010.
An Invitation to pay additional fees dated Jan. 31, 2014, which issued during the prosecution of Applicant's PCT/IL2013/050861.
An International Preliminary Report on Patentability dated Dec. 23, 2013, which issued during the prosecution of Applicant's PCT/IL2012/000250.
An International Preliminary Report on Patentability dated Sep. 18, 2007, which issued during the prosecution of Applicant's PCT/IL2006/000342.
An International Preliminary Report on Patentability dated Jun. 5, 2012, which issued during the prosecution of Applicant's PCT/IL2010/001024.
An International Preliminary Report on Patentability dated Apr. 28, 2015, which issued during the prosecution of Applicant's PCT/IL2013/050861.
An International Preliminary Report on Patentability dated Apr. 26, 2016, which issued during the prosecution of Applicant's PCT/IL2014/050914.
An International Preliminary Report on Patentability dated Jun. 10, 2009, which issued during the prosecution of Applicant's PCT/IL07/01503.
An International Preliminary Report on Patentability dated Dec. 18, 2010, which issued during the prosecution of Applicant's PCT/IL09/00593.
An International Preliminary Report on Patentability dated Jun. 29, 2011, which issued during the prosecution of Applicant's PCT/IL2009/001209.
Notice of Allowance dated Aug. 18, 2017, which issued during the prosecution of U.S. Appl. No. 14/689,608.
Notice of Allowance dated Jul. 6, 2017, which issued during the prosecution of U.S. Appl. No. 14/682,608.
Notice of Allowance dated May 22, 2017, which issued during the prosecution of U.S. Appl. No. 14/689,608.
An Office Action dated Apr. 21, 2017, which issued during the prosecution of U.S. Appl. No. 15/213,791.
An Office Action dated Sep. 29, 2017, which issued during the prosecution of U.S. Appl. No. 15/191,069.
An International Preliminary Report on Patentability dated Nov. 9, 2011, which issued during the prosecution of Applicant's PCT/IL2010/000357.
An International Preliminary Report on Patentability dated Nov. 9, 2011 which issued during the prosecution of Applicant's PCT/IL2010/000358.
An International Preliminary Report on Patentability dated Nov. 27, 2012, which issued during the prosecution of Applicant's PCT/IL2011/000404.
An International Preliminary Report on Patentability dated Feb. 4, 2014, which issued during the prosecution of Applicant's PCT/IL2011/000446.
An International Preliminary Report on Patentability dated Jan. 29, 2013, which issued during the prosecution of Applicant's PCT/IL2011/000600.
An International Preliminary Report on Patentability dated Dec. 23, 2014, which issued during the prosecution of Applicant's PCT/IL2012/050451.
A Notice of Allowance dated Jul. 30, 2015, which issued during the prosecution of U.S. Appl. No. 13/319,007.
An Office Action dated Sep. 29, 2014, which issued during the prosecution of U.S. Appl. No. 13/504,370.
An Office Action dated Jan. 13, 2015, which issued during the prosecution of U.S. Appl. No. 13/707,013.
An Office Action dated Mar. 23, 2015, which issued during the prosecution of U.S. Appl. No. 13/707,013.
Notice of Allowance dated Mar. 25, 2015, which issued during the prosecution of U.S. Appl. No. 13/749,153.
An Office Action dated Oct. 3, 2014, which issued during the prosecution of U.S. Appl. No. 13/749,153.
Notice of Allowance dated May 22, 2015, which issued during the prosecution of U.S. Appl. No. 13/749,153.
Notice of Allowance dated Aug. 3, 2015, which issued during the prosecution of U.S. Appl. No. 13/749,153.
An Office Action dated Dec. 19, 2013, which issued during the prosecution of U.S. Appl. No. 14/027,934.
An Office Action dated Jun. 11, 2014, which issued during the prosecution of U.S. Appl. No. 14/027,934.
An Office Action dated Aug. 22, 2014, which issued during the prosecution of U.S. Appl. No. 14/027,934.
An Office Action dated Apr. 2, 2015, which issued during the prosecution of U.S. Appl. No. 14/027,934.
An Office Action dated Jan. 5, 2016, which issued during the prosecution of U.S. Appl. No. 14/027,934.
An Office Action dated Jan. 5, 2016, which issued during the prosecution of U.S. Appl. No. 14/084,426.
An Office Action dated Mar. 16, 2015, which issued during the prosecution of U.S. Appl. No. 14/084,426.
An Office Action dated Jan. 6, 2016, which issued during the prosecution of U.S. Appl. No. 14/128,756.
An Office Action dated May 11, 2016, which issued during the prosecution of U.S. Appl. No. 14/128,756.
Notice of Allowance dated Oct. 20, 2015, which issued during the prosecution of U.S. Appl. No. 12/996,954.
Notice of Allowance dated Feb. 19, 2014, which issued during the prosecution of U.S. Appl. No. 12/795,192.
An Office Action dated Jul. 20, 2012, which issued during the prosecution of U.S. Appl. No. 12/843,412.
An Office Action dated Mar. 27, 2013, which issued during the prosecution of U.S. Appl. No. 12/841,412.
A Restriction Requirement dated May 1, 2012, which issued during the prosecution of U.S. Appl. No. 12/843,412.
A Notice of Allowance dated May 2, 2013, which issued during the prosecution U.S. Appl. No. 17/824,412.
A Restriction Requirement dated Nov. 19, 2012, which issued during the prosecution of U.S. Appl. No. 12/926,673.
An Office Action dated Feb. 12, 2013, which issued during the prosecution of U.S. Appl. No. 12/926,673.
An Office Action dated Oct. 22, 2013, which issued during the prosecution of U.S. Appl. No. 12/926,673.
A Notice of Allowance dated Jan. 7, 2014, which issued during the prosecution of U.S. Appl. No. 12/926,673.
An Office Action dated Oct. 9, 2013, which issued during the prosecution of U.S. Appl. No. 12/996,954.
An Office Action dated Mar. 24, 2015, which issued during the prosecution of U.S. Appl. No. 12/996,954.
An Office Action dated Oct. 5, 2012, which issued during the prosecution of U.S. Appl. No. 12/996,954.
Notice of Allowance dated Jul. 7, 2015, which issued during the prosecution of U.S. Appl. No. 12/996,954.
An Office Action dated Nov. 16, 2018, which issued during the prosecution of U.S. Appl. No. 16/042,028.
An International Search Report with Written Opinion both dated Feb. 2, 2012, which issued during the prosecution of Applicant's PCT/IL2011/000600.
An International Search Report together with Written Opinion both dated Mar. 30, 2011, which issued during the prosecution of Applicant's PCT/IL2010/001024.
An International Search Report and A Written Opinion both dated Feb. 10, 2011, which issued during the prosecution of Applicant's PCT/IL10/00890.
An Office Action dated May 28, 2015, which issued during the prosecution of U.S. Appl. No. 14/128,756.
An Office Action dated Sep. 6, 2018, which issued during the prosecution of U.S. Appl. No. 15/994,022.
An Office Action dated Sep. 7, 2018, which issued during the prosecution of U.S. Appl. No. 15/995,725.
An Office Action dated Nov. 26, 2018, which issued during the prosecution of U.S. Appl. No. 16/040,831.
An Office Action dated Jul. 11, 2018, which issued during the prosecution of U.S. Appl. No. 15/978,494.

(56) References Cited

OTHER PUBLICATIONS

An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated Oct. 12, 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An International Preliminary Report on Patentability dated Apr. 28, 2015, which issued during the prosecution of Applicant's PCT/IL2013/050860.
An Office Action dated Apr. 22, 2019, which issued during the prosecution of U.S. Appl. No. 15/668,559.
Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
An Advisory Action dated Dec. 13, 2013, which issued during the prosecution of U.S. Appl. No. 12/961,721.
An Office Action dated August 7, 2015, which issued during the prosecution of U.S. Appl. No. 14/128,756.
An Office Action dated May 19, 2011, which issued during the prosecution of U.S. Appl. No. 12/706,868.
An Office Action dated Sep. 1, 2011, which issued during the prosecution of U.S. Appl. No. 12/706,868.
An Office Action dated May 30, 2012, which issued during the prosecution of U.S. Appl. No. 12/706,868.
A Notice of Allowance dated Sep. 18, 2012, which issued during the prosecution of U.S. Appl. No. 12/706,868.
Restriction Requirement dated May 5, 2011, which issued during the prosecution of U.S. Appl. No. 12/706,868.
A Restriction Requirement dated Mar. 30, 2012, which issued during the prosecution of U.S. Appl. No. 12/785,717.
An Office Action dated Oct. 5, 2020, which issued during the prosecution of Canadian Patent Application No. 2,973,940.
An Office Action dated Nov. 30, 2020, which issued during the prosecution of U.S. Appl. No. 16/138,129.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An Office Action dated Aug. 2, 2011, which issued during the prosecution of U.S. Appl. No. 12/435,291.
Notice of Allowance dated Dec. 7, 2011, which issued during the prosecution of U.S. Appl. No. 12/435,291.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
Notice of Allowance dated Apr. 20, 2011, which issued during the prosecution of U.S. Appl. No. 12/484,512.
Notice of Allowance dated Mar. 23, 2011, which issued during the prosecution of U.S. Appl. No. 12/484,512.
An Office Action dated Jan. 27, 2012, which issued during the prosecution of U.S. Appl. No. 12/548,991.
An Office Action dated Aug. 6, 2012, which issued during the prosecution of U.S. Appl. No. 12/548,991.
An Advisory Action dated Sep. 6, 2012 which issued during the prosecution of U.S. Appl. No. 12/548,991.
Notice of Allowance dated Jun. 23, 2014, which issued during the prosecution of U.S. Appl. No. 12/548,991.
A Restriction Requirement dated Nov. 14, 2011 which issued during the prosecution of U.S. Appl. No. 12/548,991.
Amendment, Terminal Disclaimer and Extension dated Jun. 27, 2012, which issued during the prosecution of U.S. Appl. No. 12/548,991.
A Restriction Requirement dated Jul. 5, 2012, which issued during the prosecution of U.S. Appl. No. 12/563,930.
An Office Action dated Apr. 2, 2013, which issued during the prosecution of U.S. Appl. No. 12/785,717.
An Office Action dated Dec. 27, 2013, which issued during the prosecution of U.S. Appl. No. 12/785,717.
An Office Action dated Nov. 5, 2012, which issued during the prosecution of U.S. Appl. No. 12/795,026.
An Office Action dated May 10, 2012, which issued during the prosecution of U.S. Appl. No. 12/795,026.
Notice of Allowance dated Nov. 13, 2014, which issued during the prosecution of U.S. Appl. No. 12/795,026.
Notice of Allowance dated Dec. 24, 2014, which issued during the prosecution of U.S. Appl. No. 12/795,026.
A Restriction Requirement dated Jan. 6, 2012, which issued during the prosecution of U.S. Appl. No. 12/795,026.
A Restriction Requirement dated Sep. 14, 2012, which issued during the prosecution of U.S. Appl. No. 12/795,192.
An Office Action dated Aug. 15, 2013, which issued during the prosecution of U.S. Appl. No. 12/795,192.
An Office Action dated Jan. 17, 2013, which issued during the prosecution of U.S. Appl. No. 12/795,192.
Notice of Allowance dated Nov. 19, 2013, which issued during the prosecution of U.S. Appl. No. 12/795,192.
A Notice of Allowance dated Jun. 26, 2012, which issued during the prosecution of U.S. Appl. No. 12/608,316.
An Office Action dated Nov. 14, 2011, which issued during the prosecution of U.S. Appl. No. 12/608,316.
A Restriction Requirement dated Apr. 1, 2011, which issued during the prosecution of U.S. Appl. No. 12/608,316.
An Office Action dated Jul. 6, 2012, which issued during the prosecution of U.S. Appl. No. 12/692,061.
An Office Action dated Jan. 23, 2012, which issued during the prosecution of U.S. Appl. No. 12/692,061.
An Office Action dated Mar. 9, 2012, which issued during the prosecution of U.S. Appl. No. 12/689,635.
An Office Action dated Nov. 30, 2012, which issued during the prosecution of U.S. Appl. No. 12/689,635.
A Notice of Allowance dated May 22, 2013, which issued during the prosecution of U.S. Appl. No. 12/689,635.
Restriction Requirement dated Nov. 14, 2011, which issued during the prosecution of U.S. Appl. No. 12/689,635.
An Office Action dated May 6, 2013, which issued during the prosecution of U.S. Appl. No. 12/689,693.
An Office Action dated Feb. 3, 2014, which issued during the prosecution of U.S. Appl. No. 12/689,693.
Notice of Allowance dated Jun. 11, 2014, which issued during the prosecution of U.S. Appl. No. 12/689,693.
A Restriction Requirement dated Sep. 17, 2012, which issued during the prosecution of U.S. Appl. No. 12/689,693.
A Notice of Allowance dated Sep. 3, 2014, which issued during the prosecution of U.S. Appl. No. 12/689,693.
European Search Report dated Jul. 8, 2016, which issued during the prosecution of Applicant's European App No. 13849843.1.
A Supplementary European Search Report dated Dec. 4, 2012, which issued during the prosecution of European Patent Application No. EP 09834225.6.
A Supplementary European Search Report dated Mar. 28, 2013, which issued during the prosecution of European Patent Application No. EP 1077 2091.4.
Search Report in European Patent Application 10772090.6 dated Jan. 17, 2014.
Supplementary European Search Report dated Oct. 23, 2014 which issued during the prosecution of Applicant's European App No. 10826224.7.
Notice of Allowance dated May 6, 2016, which issued during the prosecution of U.S. Appl. No. 14/667,090.

(56) References Cited

OTHER PUBLICATIONS

Notice of Allowance dated Apr. 12, 2016, which issued during the prosecution of U.S. Appl. No. 14/667,090.
An Office Action dated Jun. 7, 2013 which issued during the prosecution of U.S. Appl. No. 13/141,606.
An Office Action dated Jun. 13, 2014, which issued during the prosecution of U.S. Appl. No. 13/141,606.
Notice of Allowance dated Sep. 29, 2014, which issued during the prosecution of U.S. Appl. No. 13/141,606.
An Office Action dated Feb. 4, 2013 which issued during the prosecution of U.S. Appl. No. 13/141,606.
An English translation of an Office Action dated Apr. 23, 2014 which issued during the prosecution of Chinese Patent Application No. 201080059948.4.
Communication dated Jul. 25, 2014, issued by the State Intellectual Property Office of the P.R. of China in counterpart Application No. 200980157331.3.
An International Search Report and a Written Opinion both dated Jan. 25, 2016, which issued during the prosecution of Applicant's PCT/IL2015/051027.
An International Search Report dated May 19, 2011, which issued during the prosecution of Applicant's PCT/IL2011/00064.
An International Search Report and a Written Opinion both dated Feb. 22, 2013, which issued during the prosecution of Applicant's PCT/IL201/050451.
An International Search Report & Written Opinion both dated Mar. 21, 2014, which issued during the prosecution of Applicant's PCT/IL13/50992.
An International Search Report and Written Opinion both dated Apr. 9, 2014, which issued during the prosecution of Applicant's PCT/IL13/50860.
An International Search Report and a Written Opinion both dated Apr. 15, 2014, which issued during the prosecution of Applicant's PCT/IL2013/050861.
An International Search Report & Written Opinion both dated May 12, 2015, which issued during the prosecution of Applicant's PCT/IL2014/050914.
An International Search Report and a Written Opinion both dated May 30, 2007, which issued during the prosecution of Applicant's PCT/IL2006/000342.
An International Search Report and a Written Opinion both dated Jun. 10, 2010, which issued during the prosecution of Applicant's PCT/IL09/01209.
An International Search Report and a Written Opinion both dated Aug. 17, 2010, which issued during the prosecution of Applicant's PCT/IL10/00357.
An International Search Report & Written Opinion both dated Sep. 8, 2009, which issued during the prosecution of Applicant's PCT/IL09/00593.
An International Search Report and a Written Opinion both dated Sep. 12, 2008, which issued during the prosecution of Applicant's PCT/IL07/01503.
An International Search Report and Written Opinion dated Nov. 8, 2010, which issued during the prosecution of Applicant's PCT/IL2010/000358.
An International Search Report and a Written Opinion both dated Nov. 23, 2011, which issued during the prosecution of Applicant's PCT/IL2011/000446.
Supplementary European Search Report dated Sep. 25, 2015, which issued during the prosecution of Applicant's European App No. 09794095.1.
A Supplementary European Search Report dated Feb. 1, 2011, which issued during the prosecution of European Patent Application No. EP 07849540.
An English translation of an Office Action dated Dec. 12, 2013 which issued during the prosecution of Chinese Patent Application No. 200980157331.3.
Communication regarding amended claims filed dated Dec. 27, 2012, regarding European App No. 11792047.0.
An Office Action dated Mar. 23, 2015, which issued during the prosecution of European Patent Application No. EP 09834225.6.
An English translation of an Office Action dated Jul. 17, 2015 which issued during the prosecution of Chinese Patent Application No. 201080059948.4
An English translation of an Office Action dated Dec. 16, 2015 which issued during the prosecution of Chinese Patent Application No. 201080059948.4.
Communication from the European Patent Office dated Jun. 11, 2015, which issued during the prosecution of European Patent Application No. 11811934.
A communication from the European Patent Office dated Sep. 28, 2011 which issued during the prosecution of European Application No. 09834225.6.
A communication from the European Patent Office dated Oct. 19, 2012 which issued during the prosecution of European Application No. 11792047.0.
An Office Action dated Oct. 23, 2012: which issued during the prosecution of Japanese Patent Application No. 2009-539871.
An English Translation of an Office Action dated Nov. 24, 2015, which issued during the prosecution of Israel Patent Application No. 223448. (the relevant part only).
Notice of Allowance dated Nov. 17, 2015, which issued during the prosecution of U.S. Appl. No. 14/486,226.
Notice of Allowance dated Jan. 29, 2016, which issued during the prosecution of U.S. Appl. No. 14/551,951.
An Office Action dated Jun. 18, 2015, which issued during the prosecution of U.S. Appl. No. 14/551,951.
An Office Action dated Jan. 4, 2016, which issued during the prosecution of U.S. Appl. No. 14/589,100.
An Office Action dated May 4, 2016, which issued during the prosecution of U.S. Appl. No. 14/589,100.
An International Search Report and a Written Opinion both dated Nov. 14, 2011, which issued during the prosecution of Applicant's PCT/IL2011/000404.
An International Search Report and a Written Opinion both dated Dec. 6, 2012 which issued during the prosecution of Applicant's PCT/IL2012/000250.
A Notice of Allowance dated Apr. 3, 2013, which issued during the prosecution of U.S. Appl. No. 12/563,930.
An Office Action dated Aug. 24, 2012, which issued during the prosecution of U.S. Appl. No. 12/563,930.
An Office Action dated Dec. 29, 2011, which issued during the prosecution of U.S. Appl. No. 12/563,952.
A Restriction Requirement dated Oct. 27, 2011, which issued during the prosecution of U.S. Appl. No. 12/563,952.
A Notice of Allowance dated May 24, 2012, which issued during the prosecution of U.S. Appl. No. 12/563,952.
An Office Action dated Apr. 1, 2013 which issued during the prosecution of U.S. Appl. No. 13/167,2476.
An Office Action dated Nov. 21, 2013, which issued during the prosecution of U.S. Appl. No. 13/161,476.
An Advisory Action dated Feb. 4, 2014, which issued during the prosecution of U.S. Appl. No. 13/161,476.
A Restriction Requirement dated Oct. 25, 2012 which issued during the prosecution of U.S. Appl. No. 13/167,444.
An Office Action dated Jan. 17, 2013, which issued during the prosecution of U.S. Appl. No. 13/167,444.
An Office Action dated Aug. 26, 2014 which issued during the prosecution of U.S. Appl. No. 13/167,444.
An Office Action dated Aug. 23, 2013 which issued during the prosecution of U.S. Appl. No. 13/167,444.
Notice of Allowance dated Nov. 12, 2015, which issued during the prosecution of U.S. Appl No. 13/319,007.
Notice of Allowance dated Jan. 7, 2016, which issued during the prosecution of U.S. Appl. No. 13/319,007.
An Office Action dated Oct. 2, 2013, which issued during the prosecution of U.S. Appl. No. 13/167,492.
A Restriction Requirement dated Nov. 2, 2012, which issued during the prosecution of U.S. Appl. No. 13/161,492.
An Office Action dated Feb. 14, 2013 which issued during the prosecution of U.S. Appl. No. 13/167,492.

(56) References Cited

OTHER PUBLICATIONS

Notice of Allowance dated Nov. 7, 2014, which issued during the prosecution of U.S. Appl. No. 13/161,492.
An Office Action dated Jun. 10, 2014, which issued during the prosecution of U.S. Appl. No. 13/161,492.
Notice of Allowance dated Dec. 9, 2014, which issued during the prosecution of U.S. Appl. No. 13/161,476.
Notice of Allowance dated Jan. 22, 2015, which issued during the prosecution of U.S. Appl. No. 13/167,444.
An International Preliminary Report on Patentability dated May 1, 2012, which issued during the prosecution of Applicant's PCT/IL2010/000890.
An International Preliminary Report on Patentability dated Jun 9, 2015, which issued during the prosecution of Applicant's PCT/IL2013/050992.
U.S. Appl. No. 60/873,075, filed Dec. 5, 2006.
U.S. Appl. No. 60/902,146, filed Feb. 16, 2007.
An Office Action dated Mar. 29, 2018, which issued during the prosecution of U.S. Appl. No. 15/188,507.
Notice of Allowance dated Sep. 17, 2014, which issued during the prosecution of U.S. Appl. No. 12/961,721.
An Office Action dated Oct. 1, 2015, which issued during the prosecution of U.S. Appl. No. 14/141,228.
A Restriction Requirement dated Jun. 2, 2014, which issued during the prosecution of U.S. Appl. No. 13/319,030.
An Office Action dated Oct. 14, 2014, which issued during the prosecution of U.S. Appl. No. 13/319,030.
An Office Action dated Jun. 18, 2015, which issued during the prosecution of U.S. Appl. No. 13/319,030.
An Office Action dated May 3, 2016, which issued during the prosecution of U.S. Appl. No. 13/319,030.
Notice of Allowance dated Dec. 30, 2016, which issued during the prosecution of U.S. Appl. No. 13/319,030.
An Office Action dated Apr. 7, 2015, which issued during the prosecution of U.S. Appl. No. 13/319,007.
An Office Action dated April 8, 2016, which issued during the prosecution of U.S. Appl. No. 14/141,228.
An Office Action dated Oct. 5, 2015, which issued during the prosecution of U.S. Appl. No. 14/246,417.
An Office Action dated April 7, 2016, which issued during the prosecution of U.S. Appl. No. 14/242,151.
An Office Action dated May 23, 2016, which issued during the prosecution of U.S. Appl. No. 14/209,171.
An Office Action dated Jul. 20, 2016, which issued during the prosecution of U.S. Appl. No. 14/246,417.
An Office Action dated Jun, 14, 2016, which issued during the prosecution of U.S. Appl. No. 14/273,155.
An Office Action dated Jun. 17, 2016, which issued during the prosecution of U.S. Appl. No. 14/357,040.
An Office Action dated Mar. 24, 2015, which issued during the prosecution of U.S. Appl. No. 14/486,226.
U.S. Appl. No. 61/001,013, filed Oct. 29, 2007.
U.S. Appl. No. 61/132,295, filed Jun. 16, 2008.
U.S. Appl. No. 61/265,936, filed Dec. 2, 2009.
U.S. Appl. No. 61/283,445, filed Dec. 2, 2009.
U.S. Appl. No. 61/207,908, filed Feb. 17, 2009.
U.S. Appl. No. 61/733,979, filed Dec. 6, 2012.
U.S. Appl. No. 61/717,303, filed Oct. 23, 2012.
U.S. Appl. No. 61/820,979, filed May 8, 2013.
U.S. Appl. No. 61/745,848, filed Dec. 6, 2012.
U.S. Appl. No. 61/555,570, filed Nov. 4, 2011.
U.S. Appl. No. 61/557,082, filed Nov. 8, 2011.
U.S. Appl. No. 60/662,616, filed Mar. 17, 2005.
U.S. Appl. No. 60/700,542, filed Jul. 18, 2005.
U.S. Appl. No. 61/782,121, filed Mar. 14, 2013.
European Search Report dated Jul. 15, 2016, which issued during the prosecution of Applicant's European App No. 13849947.0.
European Search Report dated Nov. 4, 2015, which issued during the prosecution of European Patent Application No. EP 1077 2091.4.
Search Report in European Patent Application 10826224.7 dated Nov. 16, 2015.
Supplementary European Search Report dated Dec. 23, 2014 which issued during the prosecution of Applicant's European App No. 10834311.
Supplementary European Search Report dated Jan. 21, 2014 which issued during the prosecution of Applicant's European App No. 11 78 6226.
A Supplementary European Search Report dated Jan. 20, 2015, which issued during the prosecution of European Patent Application No. 12803037.6.
Supplementary European Search Report dated Aug. 4, 2014 which issued during the prosecution of Applicant's European App No. 11 81 1934.6.
European Search Report dated Jun. 24, 2016, which issued during the prosecution of European Patent Application No. EP 12847363.
Supplementary European Search Report dated Apr. 29, 2015, which issued during the prosecution of Applicant's European App No. 14200202.
An Office Action dated Dec. 16, 2013, which issued during the prosecution of U.S. Appl. No. 13/666,262.
An Office Action dated Dec. 18, 2013, which issued during the prosecution of U.S. Appl. No. 13/666,141.
Notice of Allowance dated Jun. 25, 2014, which issued during the prosecution of U.S. Appl. No. 13/666,262.
A Notice of Allowance dated Feb. 2, 2015, which issued during the prosecution of U.S. Appl. No. 13/504,870.
Notice of Allowance dated Aug. 19, 2013, which issued during the prosecution of U.S. Appl. No. 11/908,906.
An Office Action dated Jun. 8, 2012, which issued during the prosecution of U.S. Appl. No. 11/908,906.
An Office Action dated Dec. 21, 2012, which issued during the prosecution of U.S. Appl. No. 11/908,906.
A Restriction Requirement dated Aug. 5, 2011, which issued during the prosecution of U.S. Appl. No. 11/908,906.
An Office Action dated Sep. 16, 2009 which issued during the prosecution of U.S. Appl. No. 11/950,930.
Notice of Allowance dated Sep. 12, 2014, which issued during the prosecution of U.S. Appl. No. 11/950,930.
An Office Action dated Aug. 5, 2010 which issued during the prosecution of U.S. Appl. No. 11/950,930.
An Office Action dated Feb. 17, 2010 which issued during the prosecution of U.S. Appl. No. 11/950,930.
A Restriction Requirement dated Apr. 19, 2010 which issued during the prosecution of U.S. Appl. No. 12/341,960.
An Office Action dated Sep. 28, 2011, which issued during the prosecution of U.S. Appl. No. 12/437,103.
An Office Action dated Jun. 13, 2012, which issued during the prosecution of U.S. Appl. No. 12/437,103.
A Restriction Requirement dated Jul. 12, 2011, which issued during the prosecution of U.S. Appl. No. 12/437,103.
Notice of Allowance dated Mar. 6, 2014, which issued during the prosecution of U.S. Appl. No. 12/437,103.
Notice of Allowance dated Dec. 20, 2013, which issued during the prosecution of U.S. Appl. No. 12/437,103.
Notice of Allowance dated Apr. 27, 2012, which issued during the prosecution of U.S. Appl. No. 12/341,960.
An Office Action dated Mar. 29, 2011, which issued during the prosecution of U.S. Appl. No. 12/341,960.
An Office Action dated Aug. 4, 2010, which issued during the prosecution of U.S. Appl. No. 12/341,960.
An Interview Summary dated Jul. 27, 2011, which issued during the prosecution of U.S. Appl. No. 12/341,960.
Notice of Allowance dated Aug. 21, 2019, which issued during the prosecution of U.S. Appl. No. 15/703,385.
Notice of Allowance dated Oct. 16, 2019, which issued during the prosecution of U.S. Appl. No. 15/703,385.
Notice of Allowance dated Dec. 24, 2020, which issued during the prosecution of U.S. Appl. No. 15/668,659.
Notice of Allowance dated Oct. 21, 2020, which issued during the prosecution of U.S. Appl. No. 15/668,659.
Declaration of Ivan Vesely, Ph.D., in Support of Petition for Inter Partesreview of U.S. Pat. No. 7,563,267—dated May 29, 2019.

(56) References Cited

OTHER PUBLICATIONS

U.S. Appl. No. 60/128,690, filed Apr. 9, 1999.
U.S. Appl. No. 60/613,867, filed Sep. 27, 2004.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action dated Jan. 13, 2021, which issued during the prosecution of European Patent Application No. 15751089.2.
An Office Action together with an English summary dated Mar. 3, 2021, which issued during the prosecution of Chinese Patent Application No. 201780047391.4.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Kalbacher, D., et al. "1000 MitraClip™ procedures: Lessons learnt from the largest single-centre experience worldwide." (2019): 3137-3139.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
Notice of Allowance dated Nov. 19, 2019, which issued during the prosecution of U.S. Appl. No. 15/668,559.
Mitral Valve Academic Research Consortium. "Clinical Trial Design Principles and Endpoint Definitions for Transcatheter Mitral Valve Repair and Replacement: Part 1: Clinical Trial Design Principles A Consensus Document from the Mitral Valve Academic Research Consortium." Journal of the American College of Cardiology 66.3 (2015): 278-307.
An Office Action dated Aug. 29, 2018, which issued during the prosecution of U.S. Appl. No. 15/329,920.
An Office Action dated May 8, 2018, which issued during the prosecution of U.S. Appl. No. 15/902,403.
An Office Action dated May 11, 2018, which issued during the prosecution of U.S. Appl. No. 15/899,858.
Notice of Allowance dated Oct. 5, 2018, which issued during the prosecution of U.S. Appl. No. 15/886,517.
Notice of Allowance dated Jul. 19, 2019, which issued during the prosecution of U.S. Appl. No. 15/899,858.
Notice of Allowance dated Nov. 16, 2020, which issued during the prosecution of U.S. Appl. No. 16/324,339.
Notice of Allowance dated Apr. 27, 2020, which issued during the prosecution of U.S. Appl. No. 16/591,330.
An Advisory Action dated Jan. 2, 2020, which issued during the prosecution of U.S. Appl. No. 15/668,659.
Notice of Allowance dated Oct. 17, 2019, which issued during the prosecution of U.S. Appl. No. 15/329,920.
An Office Action dated Dec. 31, 2019, which issued during the prosecution of U.S. Appl. No. 16/591,330.
Notice of Allowance dated Feb. 9, 2021, which issued during the prosecution of U.S. Appl. No. 16/937,216.
An Office Action dated Sep. 29, 2022, which issued during the prosecution of U.S. Appl. No. 17/010,886.
An Office Action dated Sep. 29, 2022, which issued during the prosecution of U.S. Appl. No. 16/656,790.
An Office Action dated Nov. 2, 2022, which issued during the prosecution of U.S. Appl. No. 17/004,693.
An Office Action dated Oct. 19, 2022, which issued during the prosecution of U.S. Appl. No. 17/875,589.
An Office Action dated Oct. 26, 2022, which issued during the prosecution of U.S. Appl. No. 16/746,489.
An Office Action dated Mar. 3, 2023, which issued during the prosecution of European Patent Application No. 17751143.3.
An Office Action dated Mar. 20, 2023, which issued during the prosecution of U.S. Appl. No. 17/181,722.
European Search Report dated Mar. 20, 2023 which issued during the prosecution of Applicant's European App No. 22204764.9.
Notice of Allowance dated Apr. 6, 2023, which issued during the prosecution of U.S. Appl. No. 16/746,489.
An Office Action dated Apr. 14, 2023, which issued during the prosecution of U.S. Appl. No. 16/144,054.
An Office Action dated May 15, 2023, which issued during the prosecution of U.S. Appl. No. 16/656,790.
An Office Action dated May 16, 2023, which issued during the prosecution of U.S. Appl. No. 17/114,771.
An Office Action dated May 17, 2023, which issued during the prosecution of U.S. Appl. No. 17/466,785.
An Office Action dated May 25, 2023, which issued during the prosecution of U.S. Appl. No. 17/397,235.

* cited by examiner

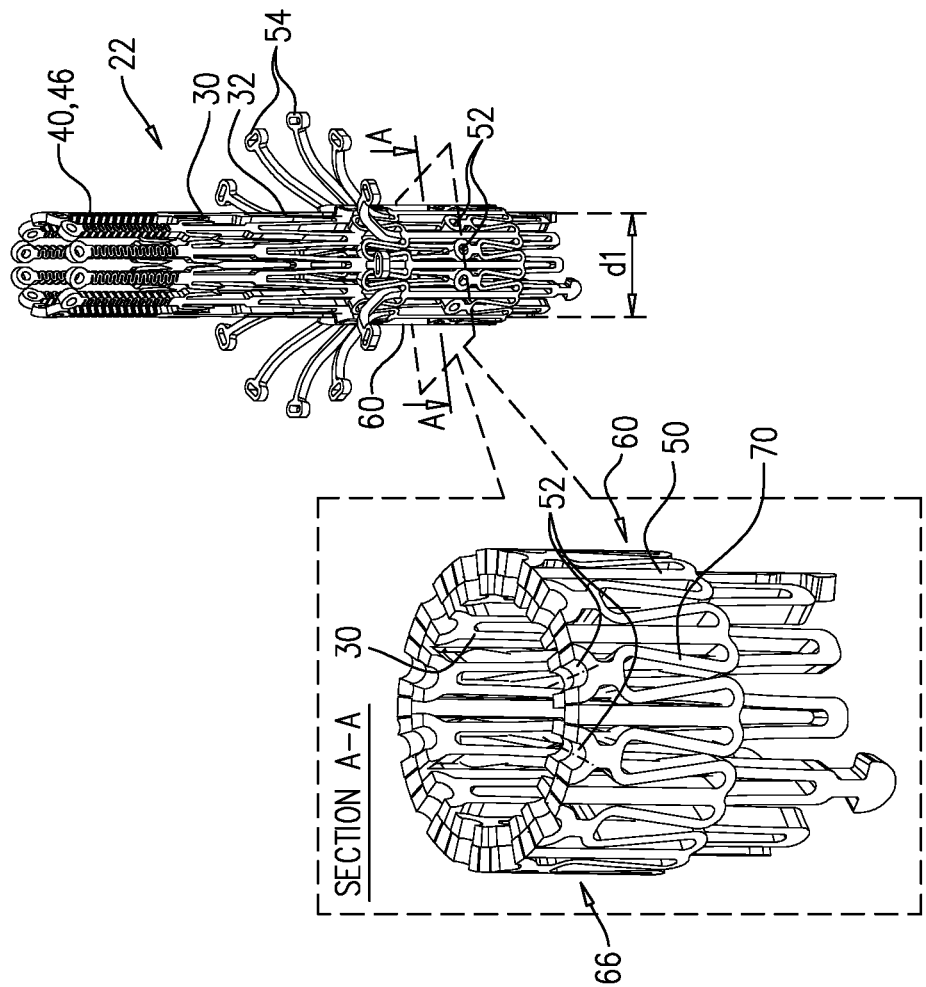
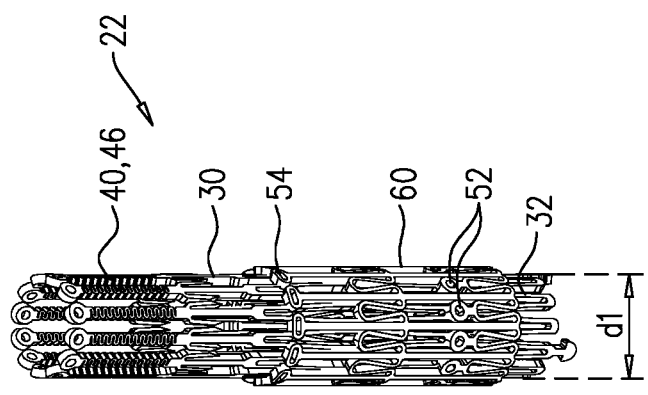

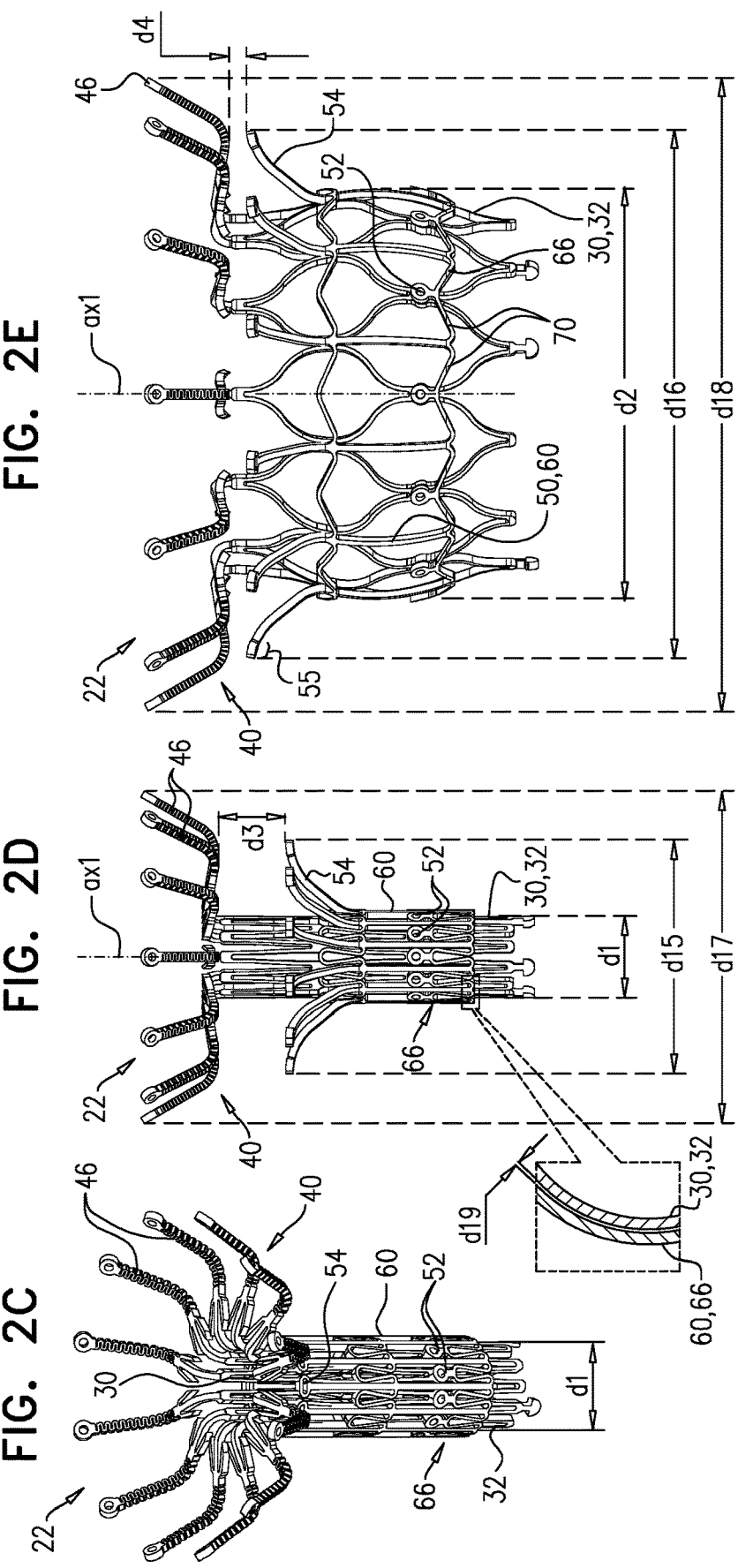

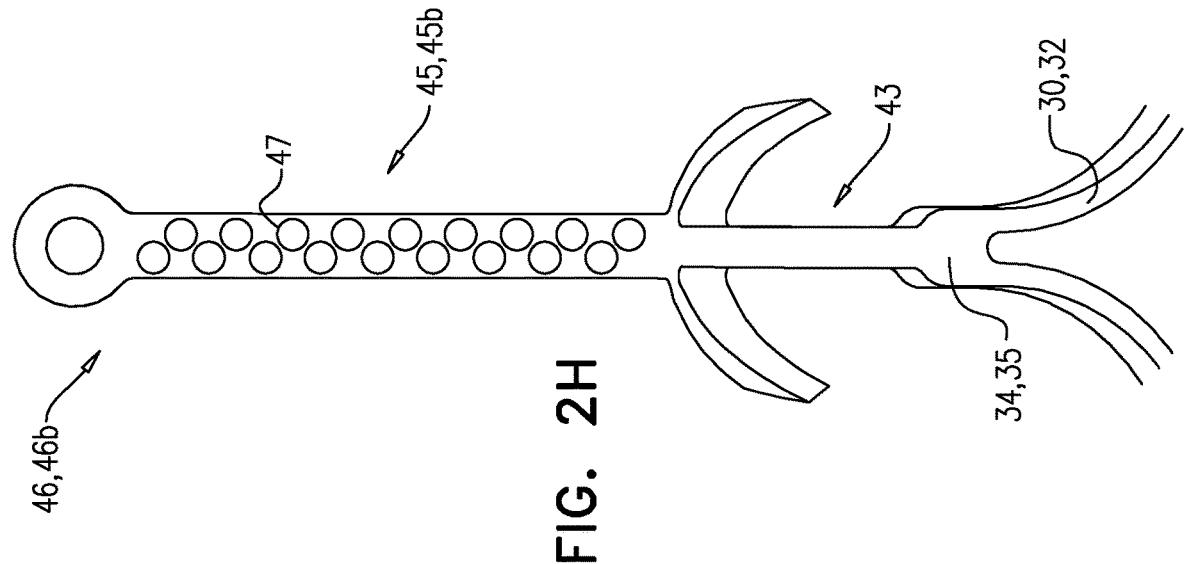
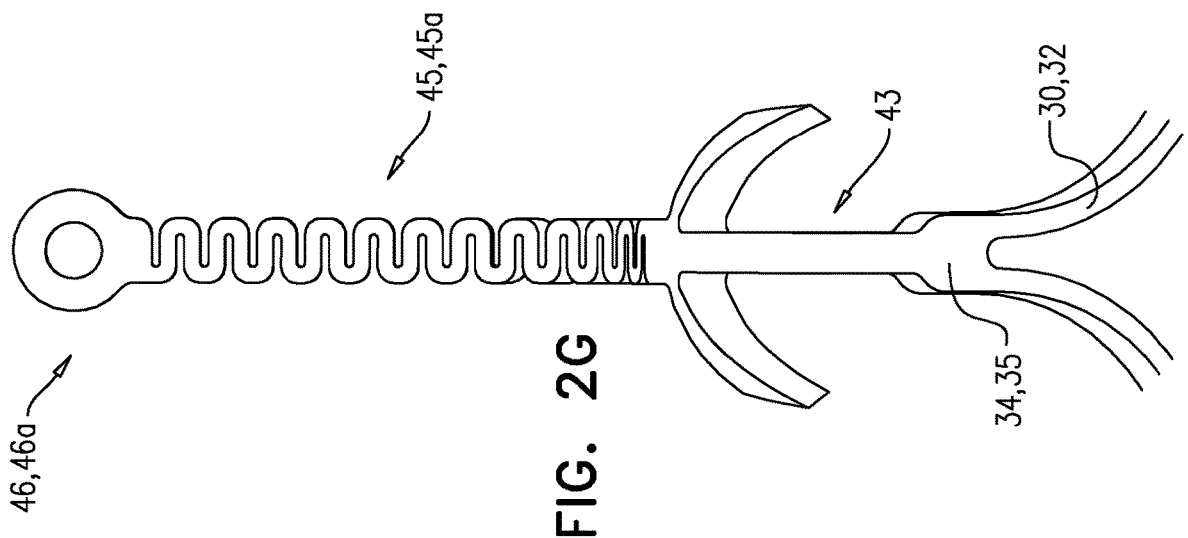

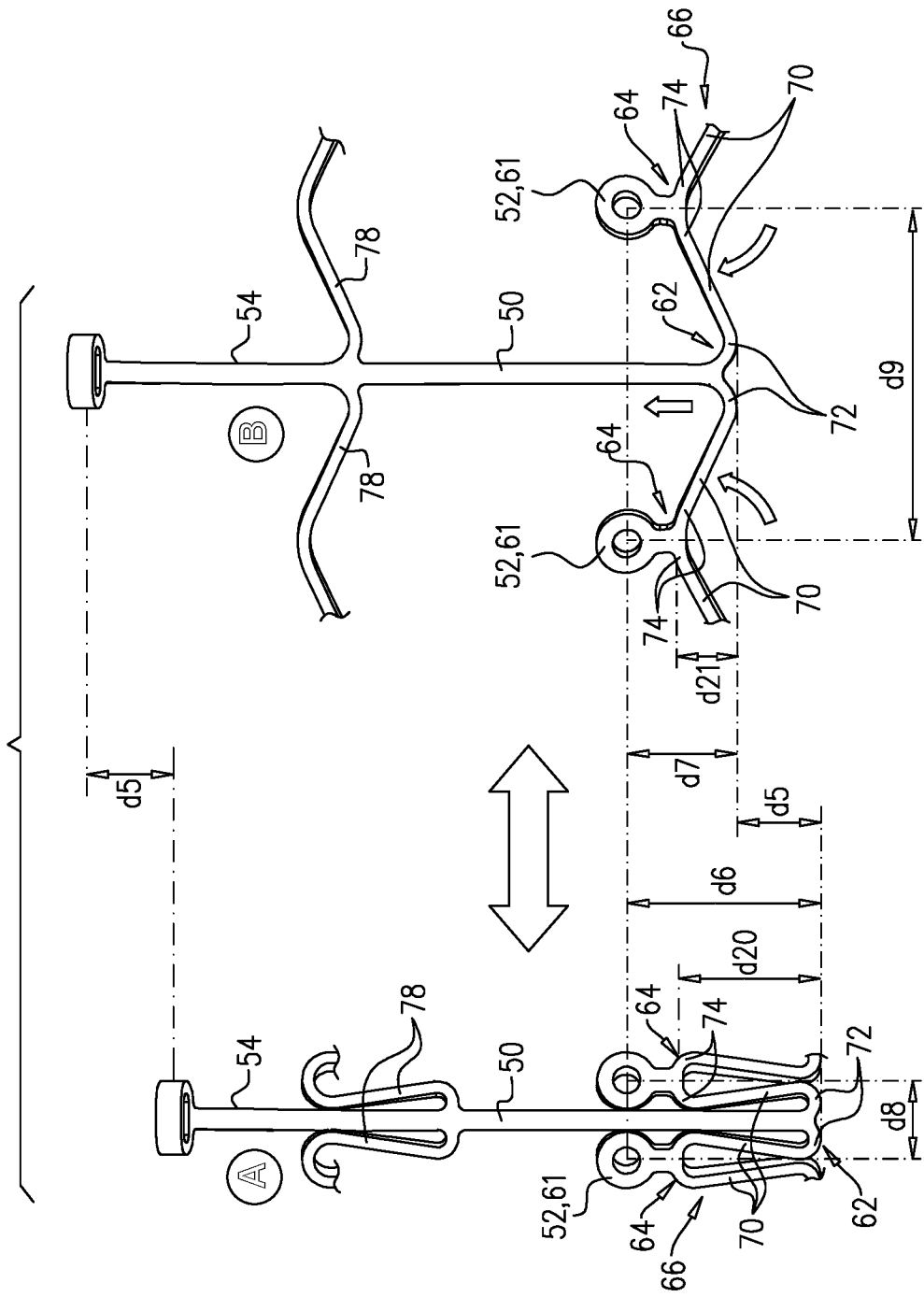

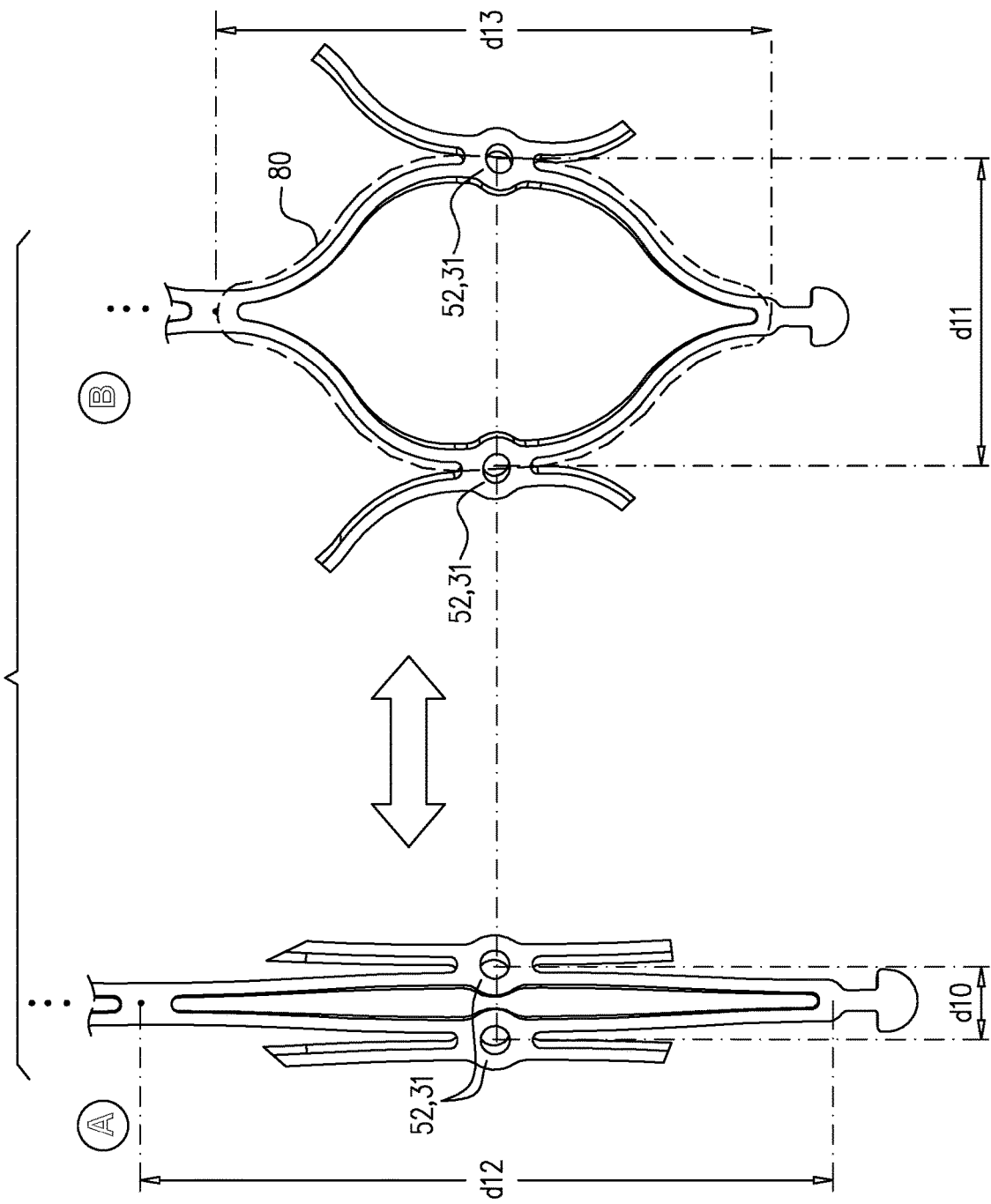

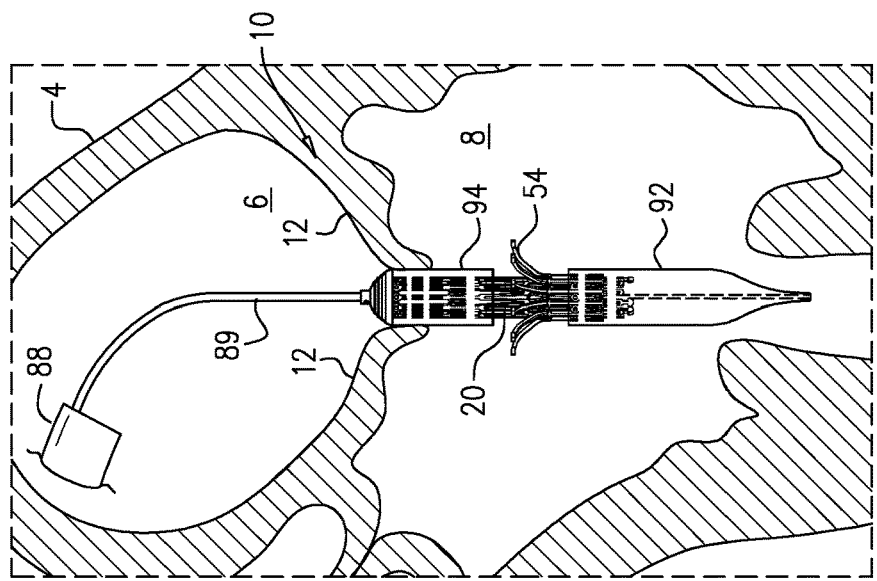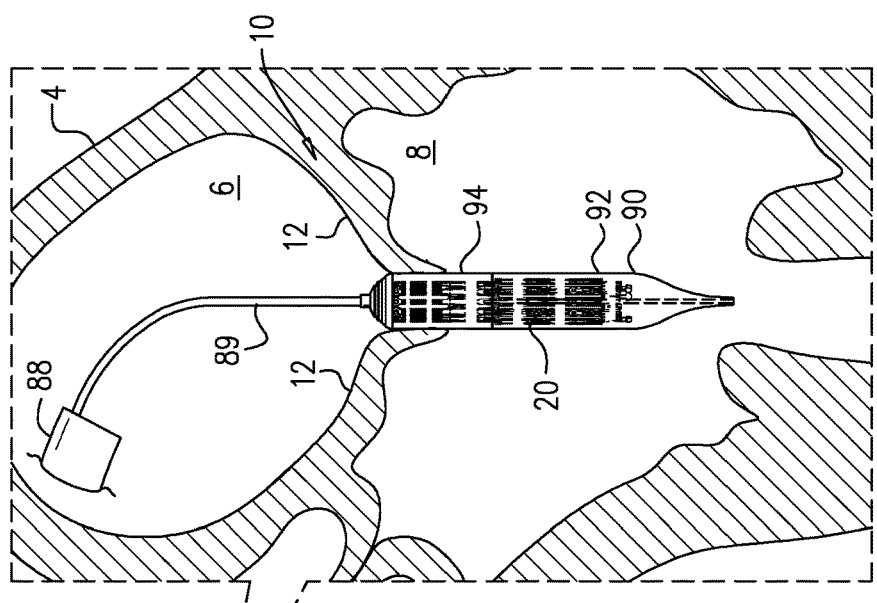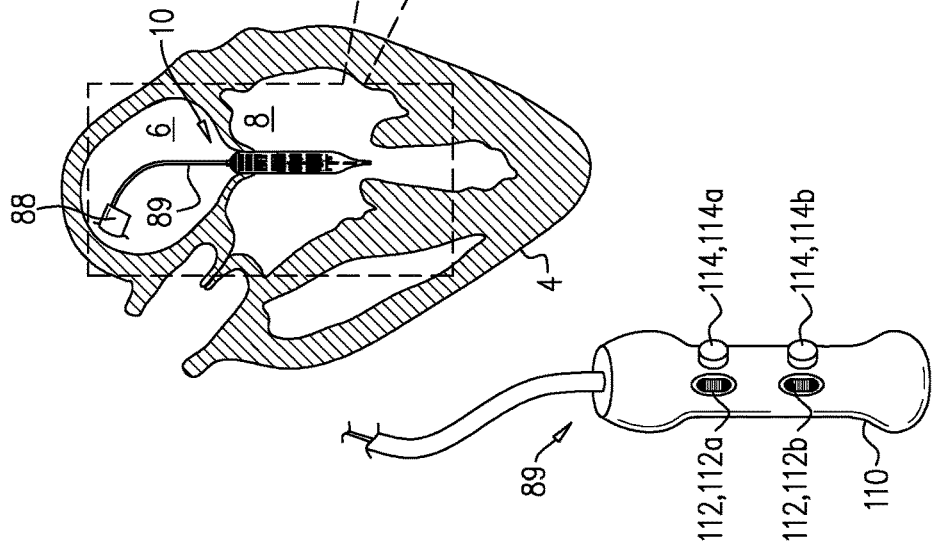

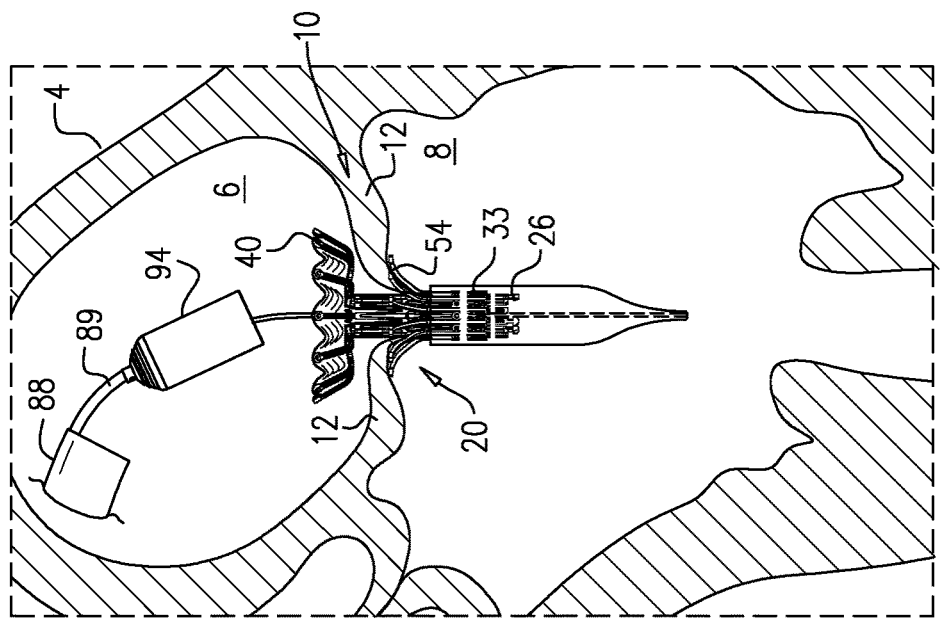
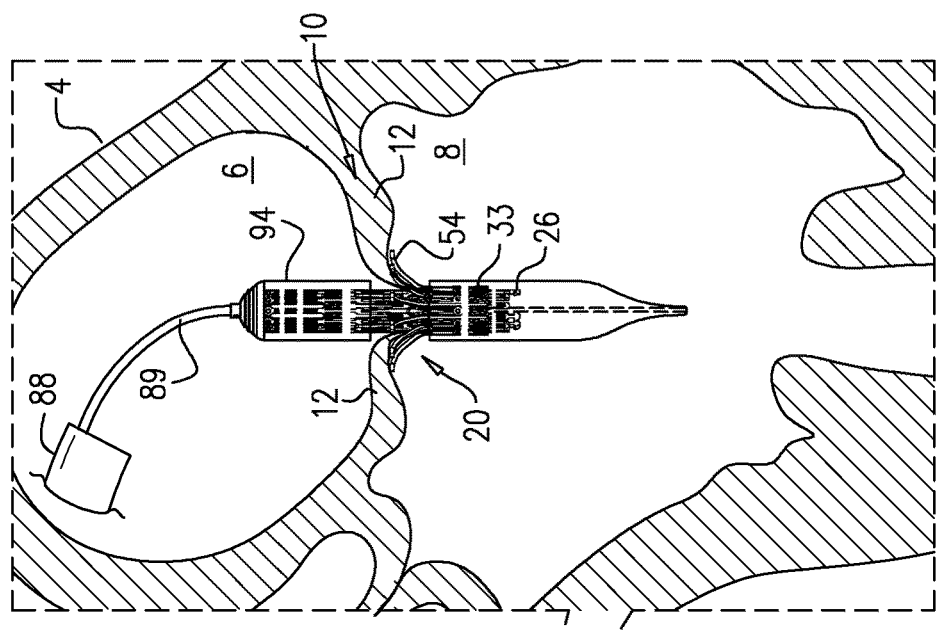
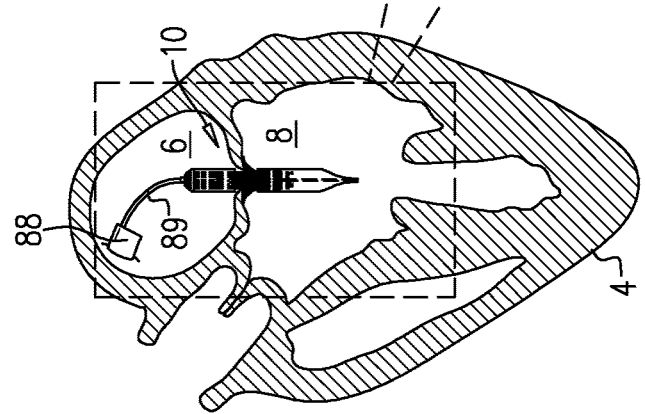
FIG. 4C
FIG. 4D

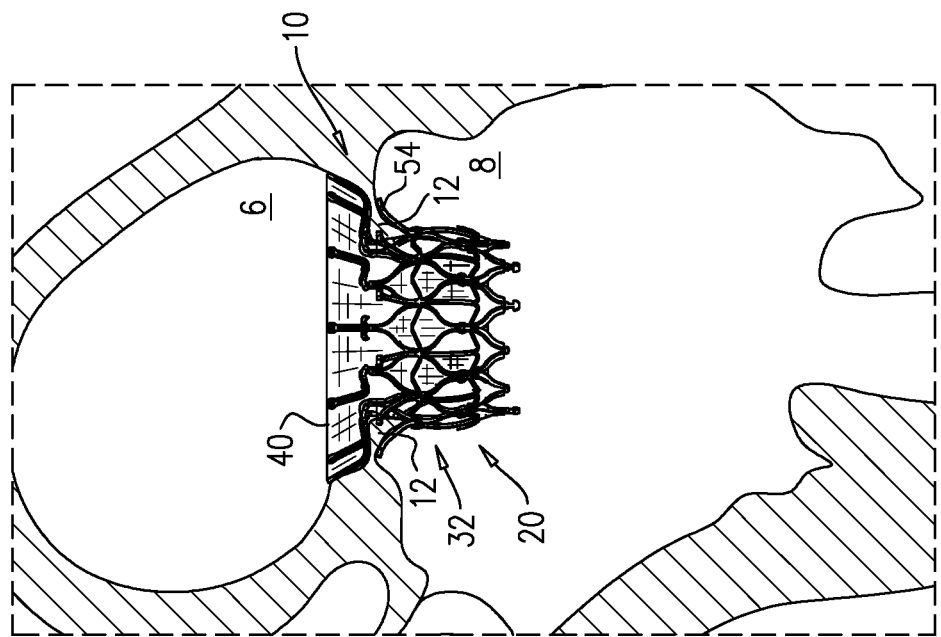
FIG. 4F
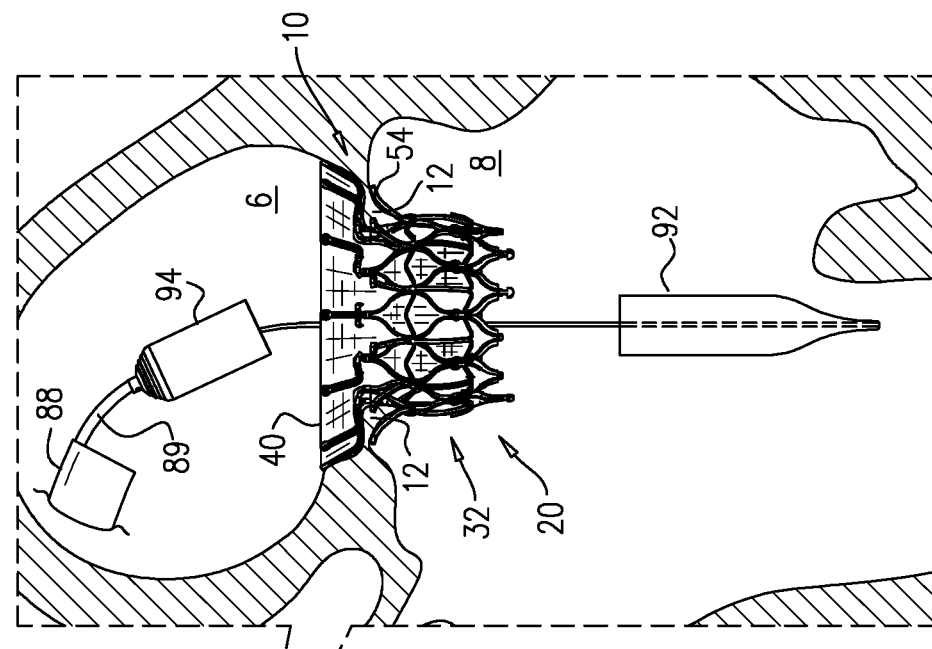
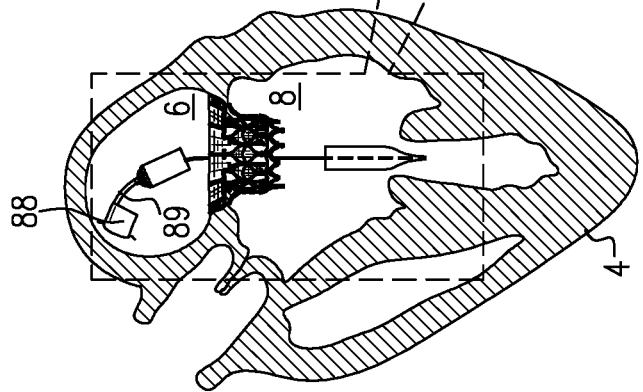
FIG. 4E

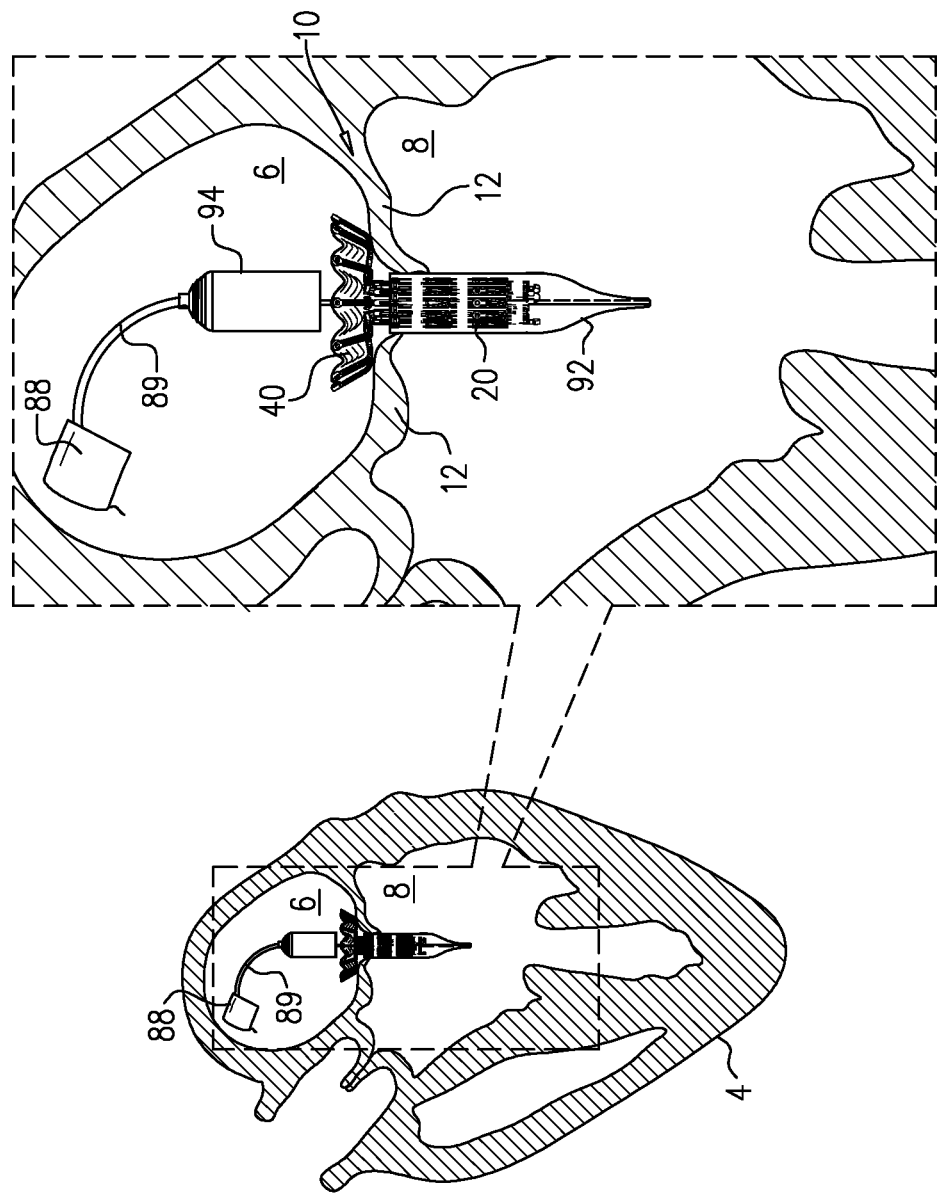

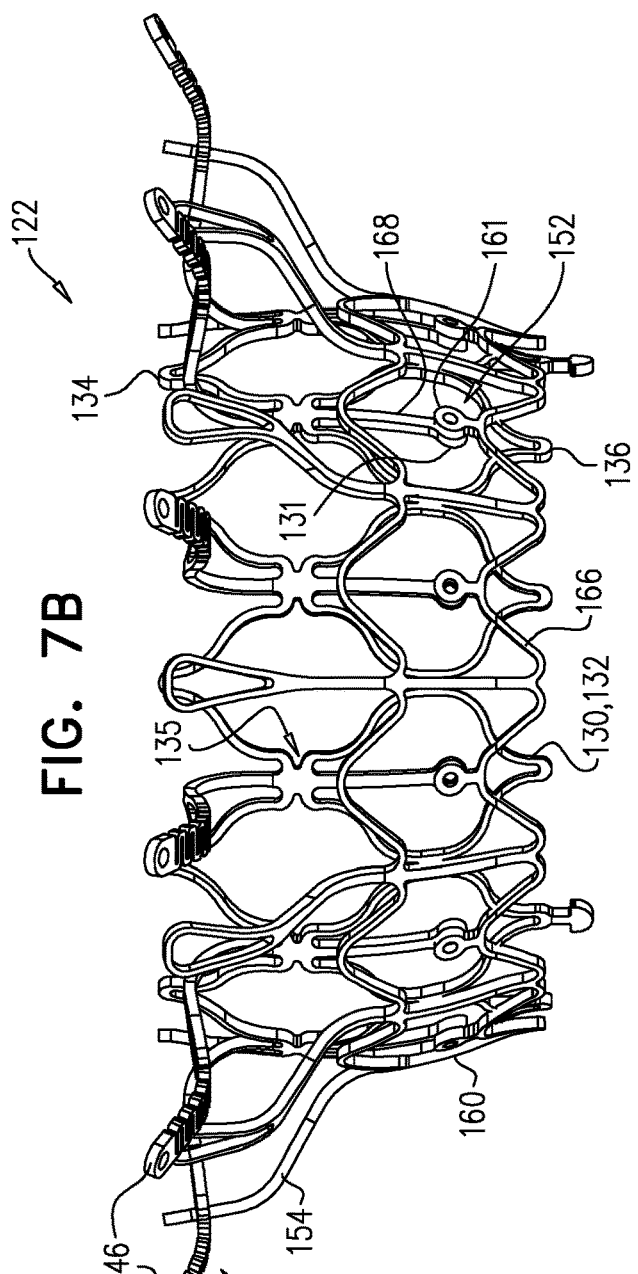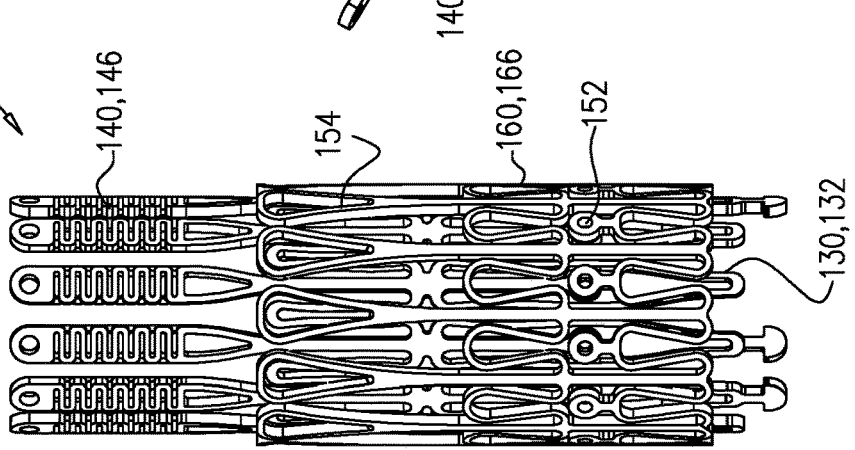

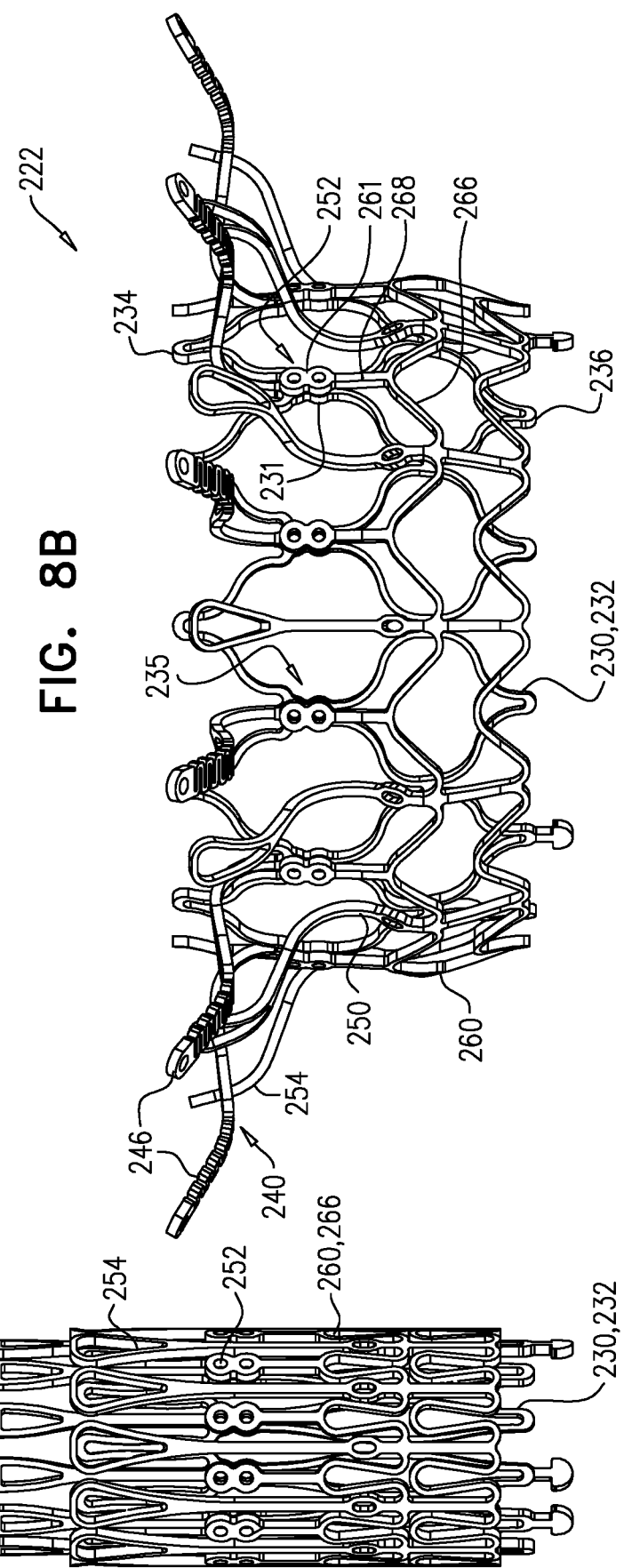

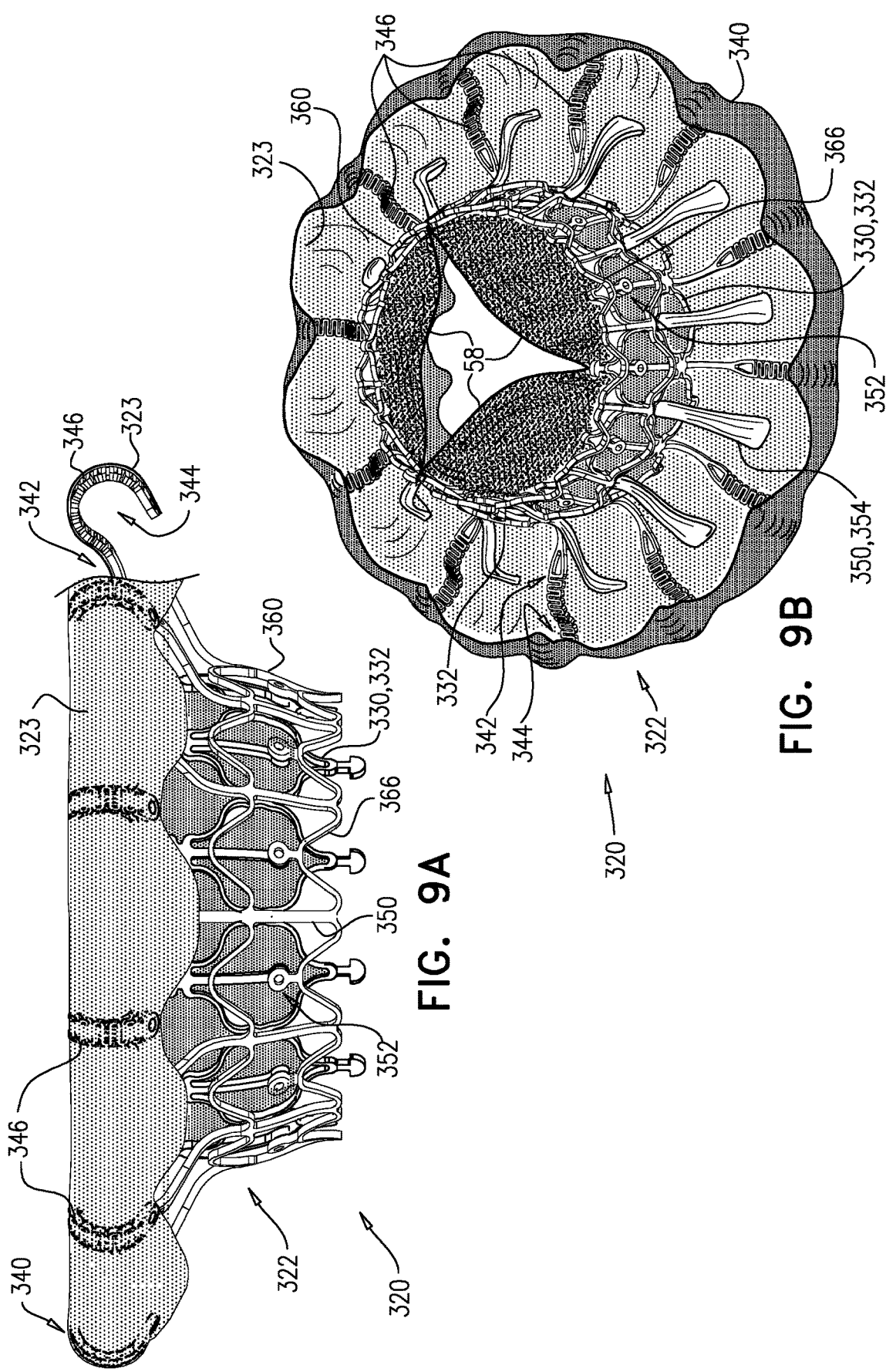

TECHNIQUES FOR DEPLOYMENT OF A PROSTHETIC VALVE

CROSS-REFERENCES TO RELATED APPLICATIONS

This application is a Continuation application of U.S. patent application Ser. No. 15/668,659, filed Aug. 3, 2017, entitled, "Techniques for deployment of a prosthetic valve," which issued as U.S. Pat. No. 10,918,481 and which:
(1) is a Continuation-In-Part of PCT application IL2016/050125, filed Feb. 3, 2016, entitled "Prosthetic valve with axially-sliding frames," which published as WO 2016/125160, and which claims priority from U.S. Provisional Patent Application 62/112,343 to Hariton et al., filed Feb. 5, 2015, and entitled "Prosthetic valve with axially-sliding frames"; and
(2) is a Continuation-In-Part of U.S. patent application Ser. No. 15/541,783, entitled "Prosthetic valve with axially-sliding frames," which issued as U.S. Pat. No. 9,974,651, and which is the US National Phase of PCT application IL2016/050125, filed Feb. 3, 2016, entitled "Prosthetic valve with axially-sliding frames," which published as WO 2016/125160, and which claims priority from U.S. Provisional Patent Application 62/112, 343 to Hariton et al., filed Feb. 5, 2015, and entitled "Prosthetic valve with axially-sliding frames."

All of the above applications are incorporated herein by reference.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications, an implant is provided having a tubular portion, an upstream support portion and one or more flanges. The implant is percutaneously deliverable to a native heart valve in a compressed state, and is expandable at the native valve. The implant and its delivery system facilitate causing the upstream support portion and the flanges to protrude radially outward from the tubular portion without expanding the tubular portion. Expansion of the tubular portion brings the upstream support portion and the flanges closer together, for securing the implant at the native valve by sandwiching tissue of the native valve between the upstream support portion and the flanges.

For some applications, a delivery tool is provided, including a delivery capsule, disposed at a distal portion of the tool. The delivery capsule includes a proximal capsule-portion dimensioned to house a first part of an implant, and a distal capsule-portion dimensioned to house a second part of the implant; and an extracorporeal control portion, disposed at a proximal portion of the tool, the control portion including one or more controllers and one or more locks. The controllers are operatively coupled to the proximal and distal capsule-portions such that the proximal and distal capsule-portions are movable with respect to the implant via actuation of the controllers. The tool has sequential states in which movement of the proximal and distal capsule-portions is variously inhibited or facilitated. For some applications, in response to a movement of a capsule-portion that is facilitated in a given state, the tool unlocks the subsequent state.

There is therefore provided, in accordance with an application of the present invention, apparatus including an implant and a delivery tool, the tool including:
a delivery capsule, disposed at a distal portion of the tool, the delivery capsule including a proximal capsule-portion dimensioned to house a first part of the implant, and a distal capsule-portion dimensioned to house a second part of the implant; and
an extracorporeal control portion, disposed at a proximal portion of the tool, the control portion including one or more controllers and one or more locks, the controllers being operatively coupled to the proximal and distal capsule-portions such that the proximal and distal capsule-portions are movable with respect to the implant via actuation of the controllers,
and the controllers and the locks are mechanically cooperative such that:
in a state A of the tool:
a first distal movement of the distal capsule-portion up to a first distance distally with respect to the implant is facilitated,
a second distal movement of the distal capsule-portion further distally with respect to the implant is inhibited, and
a proximal movement of the proximal capsule-portion proximally with respect to the implant is facilitated; and
in a state B of the tool:
the second distal movement of the distal capsule-portion is facilitated.

In an application, in the state A, a lock of the one or more locks is locked, and unlocking of the lock transitions the tool into the state B.

In an application, the lock is not unlockable until the distal capsule-portion has been moved the first distance distally with respect to the implant.

In an application, the lock is not unlockable until the proximal capsule-portion has been moved proximally with respect to the implant.

In an application:
the one or more controllers include a first controller and a second controller, and
in the state A, actuation of the first controller causes the first distal movement of the distal capsule-portion, and actuation of the second controller causes the proximal movement of the proximal capsule-portion.

In an application, in the state B, further actuation of the first controller causes the second distal movement of the distal capsule-portion.

In an application, the one or more controllers further include a third controller, and, in the state B, actuation of the third controller causes the second distal movement of the distal capsule-portion.

In an application, the implant is for use at a native mitral valve of a subject, and:

the first part of the implant includes an upstream support portion, configured to be placed against an upstream surface of the native mitral valve, the second part of the implant includes a downstream end of the implant, and a plurality of flanges (i) disposed longitudinally between the upstream support portion and the downstream end, and (ii) configured to engage leaflets of the native mitral valve; and the implant is housed by the delivery capsule such that the first distal movement of the distal capsule-portion unhouses, from the distal capsule-portion, the plurality of flanges, but not the downstream end of the implant.

In an application, the implant is housed by the delivery capsule such that the second distal movement of the distal capsule-portion unhouses, from the distal capsule-portion, the downstream end of the implant.

In an application, the implant is housed by the delivery capsule such that the proximal movement of the proximal capsule-portion unhouses, from the proximal capsule-portion, the upstream support portion.

In an application, the implant includes:
a valve frame that includes:
a tubular portion shaped to define a lumen therethrough, and
the upstream support portion, extending from an upstream end of the tubular portion;
an outer frame that circumscribes the tubular portion, and includes the plurality of flanges; and
a plurality of prosthetic leaflets, coupled to the tubular portion within the lumen.

In an application, the second part of the implant includes at least part of the tubular portion.

There is further provided, in accordance with an application of the present invention, apparatus including an implant and a delivery tool, the tool including:

a delivery capsule, disposed at a distal portion of the tool, the delivery capsule including a proximal capsule-portion dimensioned to house a first part of the implant, and a distal capsule-portion dimensioned to house a second part of the implant; and an extracorporeal control portion, disposed at a proximal portion of the tool, the control portion including one or more controllers and one or more locks, the controllers being operatively coupled to the proximal and distal capsule-portions such that the proximal and distal capsule-portions are movable with respect to the implant via actuation of the controllers, and the controllers and the locks are mechanically cooperative such that:

in a first state of the tool:
a first distal movement of the distal capsule-portion up to a first distance distally with respect to the implant is facilitated,
a second distal movement of the distal capsule-portion further distally with respect to the implant is inhibited,
a proximal movement of the proximal capsule-portion proximally with respect to the implant is inhibited, and
responsively to movement of the distal capsule-portion distally, the tool automatically unlocks a second state of the tool;

in the second state of the tool:
the proximal movement of the proximal capsule-portion is facilitated,
the second distal movement of the distal capsule-portion remains inhibited, and
responsively to movement of the proximal capsule-portion proximally, the tool automatically unlocks a third state of the tool; and in the third state of the tool:
the second distal movement of the distal capsule-portion is facilitated.

In an application, the tool automatically unlocks the second state responsively to the distal capsule-portion having moved the first distance.

In an application:
the one or more locks include a first lock and a second lock,
the one or more controllers include a first controller and a second controller,
in the first state of the tool, actuation of the first controller causes the first distal movement of the distal capsule-portion,
the tool automatically unlocks the second state by automatically making the first lock unlockable,
in the second state of the tool, actuation of the second controller causes the proximal movement of the proximal capsule-portion, and
the tool automatically unlocks the third state by automatically making the second lock unlockable.

In an application, in the third state of the tool, further actuation of the first controller causes the second distal movement of the distal capsule-portion.

In an application, the one or more controllers further include a third controller, and, in the third state of the tool, actuation of the third controller causes the second distal movement of the distal capsule-portion.

In an application, the implant is for use at a native mitral valve of a subject, and:

the first part of the implant includes an upstream support portion, configured to be placed against an upstream surface of the native mitral valve, the second part of the implant includes a downstream end of the implant, and a plurality of flanges (i) disposed longitudinally between the upstream support portion and the downstream end, and (ii) configured to engage leaflets of the native mitral valve; and the implant is housed by the delivery capsule such that the first distal movement of the distal capsule-portion unhouses, from the distal capsule-portion, the plurality of flanges, but not the downstream end of the implant.

In an application, the implant is housed by the delivery capsule such that the second distal movement of the distal capsule-portion unhouses, from the distal capsule-portion, the downstream end of the implant.

In an application, the implant is housed by the delivery capsule such that the proximal movement of the proximal capsule-portion unhouses, from the proximal capsule-portion, the upstream support portion.

In an application, the implant includes:
a valve frame that includes:
a tubular portion shaped to define a lumen therethrough, and
the upstream support portion, extending from an upstream end of the tubular portion;
an outer frame that circumscribes the tubular portion, and includes the plurality of flanges; and a plurality of prosthetic leaflets, coupled to the tubular portion within the lumen.

In an application, the second part of the implant includes at least part of the tubular portion.

There is further provided, in accordance with an application of the present invention, a method, including:

percutaneously advancing an implant to a native heart valve of a subject, the implant housed in a compressed state within a delivery tool;

unhousing a longitudinally-intermediate portion of the implant, the longitudinally-intermediate portion being longitudinally between a longitudinally-proximal portion of the implant and a longitudinally distal portion of the implant;

subsequently, unhousing the longitudinally-proximal portion of the implant; and subsequently, unhousing the longitudinally-distal portion of the implant.

In an application:

unhousing the longitudinally-intermediate portion of the implant includes unhousing flanges of the implant such that the flanges automatically expand;

unhousing the longitudinally-proximal portion of the implant includes unhousing an upstream support portion of the implant such that the upstream support portion automatically expands; and unhousing the longitudinally-distal portion of the implant includes unhousing the longitudinally-distal portion of the implant such that the longitudinally-distal portion of the implant automatically expands.

In an application, the longitudinally-distal portion includes a tubular portion within which a valve member is disposed, and unhousing the longitudinally-distal portion of the implant includes unhousing the longitudinally-distal portion of the implant such that the tubular portion expands to form a lumen and the valve member regulates one-way flow of blood through the lumen.

In an application, unhousing the longitudinally-distal portion of the implant includes facilitating expansion of the implant such that the tubular portion expands and the flanges become longitudinally closer to the upstream support portion.

There is further provided, in accordance with an application of the present invention, apparatus for use with a native valve that is disposed between an atrium and a ventricle of a heart of a subject, the apparatus including:

a valve frame, including:
a tubular portion that circumscribes a longitudinal axis of the valve frame so as to define a lumen along the axis, the tubular portion defining a plurality of valve-frame coupling elements disposed circumferentially around the longitudinal axis; and
a plurality of arms, extending radially outward from an upstream portion of the tubular portion to define an arm span, and configured to engage tissue in the atrium;
a plurality of prosthetic leaflets, coupled to the frame, disposed within the lumen, and arranged to provide unidirectional flow of blood from an upstream end of the lumen to a downstream end of the lumen; and
an outer frame:
coupled to the valve frame, and
including a ring that circumscribes the tubular portion, and a plurality of flanges that extend radially outward from the ring to define a flange span, and are configured to engage tissue of the ventricle,
and:
each arm of the plurality of arms defines a rigid portion and a flexible portion that is disposed radially outward from the rigid portion, and is more flexible than the rigid portion, and the majority of the flexible portion is disposed further radially outward than the flange span.

In an application, the implant is configured such that the rigid portion provides resistance against axial movement of the implant, while the flexible portion facilitates conformation of the arm to anatomy of the atrium and/or lateral movement of the implant within the native valve.

In an application, each arm of the plurality of arms defines a serpentine shape in the flexible portion.

In an application, each arm of the plurality of arms defines a plurality of holes in the flexible portion.

In an application, less than 90 percent of the flexible portion is disposed further radially outward than the flange span.

In an application, more than 60 percent of the flexible portion is disposed further radially outward than the flange span.

In an application, for each arm of the plurality of arms, the flexible portion covers an overall surface area including (i) the area occupied by material from which the arm is formed, and (ii) spaces, and the material from which the arm is formed occupies less than 80 percent of the overall surface area.

In an application, the material from which the arm is formed occupies more than 20 percent of the overall surface area.

In an application, the material from which the arm is formed occupies less than 70 percent of the overall surface area.

There is further provided, in accordance with an application of the present invention, apparatus for use with a native valve that is disposed between an atrium and a ventricle of a heart of a subject, the apparatus including:

a valve frame, including a tubular portion that circumscribes a longitudinal axis of the valve frame so as to define a lumen along the axis, the tubular portion defining a plurality of valve-frame coupling elements disposed circumferentially around the longitudinal axis;

a plurality of prosthetic leaflets, coupled to the frame, disposed within the lumen, and arranged to provide unidirectional flow of blood from an upstream end of the lumen to a downstream end of the lumen;

an outer frame:
including a ring defined by a pattern of alternating peaks and troughs, the peaks being longitudinally closer to the upstream end than to the downstream end, and the troughs being longitudinally closer to the downstream end than to the upstream end, and the pattern of the ring having an amplitude longitudinally between the peaks and the troughs,
including a plurality of legs, each of the legs coupled to the ring at a respective trough, and
shaped to define a plurality of outer-frame coupling elements, each of the outer-frame coupling elements (i) coupled to the ring at a respective peak, and (ii) fixed with respect to a respective valve-frame coupling element,
and:
the tubular portion has (i) a compressed state in which the tubular portion has a compressed diameter, and (ii) an expanded state in which the tubular portion has an expanded diameter that is greater than the compressed diameter, and
the fixation of the outer-frame coupling elements to the valve-frame coupling elements is such that compression of the tubular portion from the expanded state toward the compressed state such that the valve-frame coupling elements pull the outer-frame coupling elements radially inward: (i) reduces a circumferential distance between each of the outer-frame coupling elements and its adjacent outer-frame coupling elements, and (ii) increases the amplitude of the pattern of the ring.

In an application, the ring circumscribes the tubular portion.

In an application, the valve-frame coupling elements are disposed circumferentially around the longitudinal axis between the upstream end and the downstream end but not at the upstream end nor at the downstream end.

In an application, the upstream support portion includes one or more fabric pockets disposed circumferentially, each pocket of the one or more pockets having an opening that faces a downstream direction.

In an application, the outer frame is coupled to the valve frame only via the fixation of the outer-frame coupling elements to the respective valve-frame coupling elements.

In an application, the apparatus further includes an upstream support portion that includes a plurality of arms that extend radially from the tubular portion, and:
the upstream support portion has (i) a constrained-arm state, and (ii) a released-arm state in which the arms extend radially outward from the tubular portion,
each leg has a tissue-engaging flange that has (i) a constrained-flange state, and (ii) a released-flange state in which the flange extends radially outward from the tubular portion, and
the apparatus has an intermediate state in which (i) the tubular portion is in its compressed state, (ii) the upstream support portion is in its released-arm state, and (iii) the legs are in their released-flange state.

In an application:
the apparatus includes an implant that includes the valve frame, the leaflets, and the outer frame, and
the apparatus further includes a tool:
including a delivery capsule dimensioned (i) to house and retain the implant in a compressed state of the implant in which (a) the tubular portion is in its compressed state, (b) the upstream support portion is in its constrained-arm state, and (c) the legs are in their constrained-flange state, and (ii) to be advanced percutaneously to the heart of the subject while the implant is housed and in its compressed state, and
operable from outside the subject to:
transition the implant from its compressed state into the intermediate state while retaining the tubular portion in its compressed state, and
subsequently, expand the tubular portion toward its expanded state.

In an application, the tool is operable from outside the subject to transition the implant from its compressed state into the intermediate state by (i) releasing the legs into their released-flange state, while retaining the tubular portion in its compressed state, and (ii) subsequently, releasing the upstream support portion into its released-arm state, while retaining the tubular portion in its compressed state.

In an application, the tool is operable from outside the subject to transition the implant from its compressed state into the intermediate state by (i) releasing the upstream support portion into its released-arm state, while retaining the tubular portion in its compressed state, and (ii) subsequently, releasing the legs into their released-flange state, while retaining the tubular portion in its compressed state.

In an application, the fixation of the outer-frame coupling elements to the valve-frame coupling elements is such that, when the apparatus is in its intermediate state, expansion of the tubular portion from its compressed state toward its expanded state moves the flanges longitudinally away from the valve-frame coupling elements.

In an application, the fixation of the outer-frame coupling elements to the valve-frame coupling elements is such that, when the apparatus is in its intermediate state, expansion of the tubular portion from its compressed state toward its expanded state reduces the amplitude of the pattern of the ring and passes the flanges between the arms.

In an application, the upstream support portion further includes a covering that covers the arms to form an annular shape in the released-arm state, and, when the apparatus is in its intermediate state, expansion of the tubular portion from its compressed state toward its expanded state presses the flanges onto the covering.

In an application, in the compressed state of the tubular portion, a downstream end of each leg is longitudinally closer than the valve-frame coupling elements to the downstream end, and the flange of each leg is disposed longitudinally closer than the valve-frame coupling elements to the upstream end.

In an application, in the expanded state of the tubular portion, the downstream end of each leg is longitudinally closer than the valve-frame coupling elements to the downstream end, and the flange of each leg is disposed longitudinally closer than the valve-frame coupling elements to the upstream end.

There is further provided, in accordance with an application of the present invention, apparatus for use with a native valve of a heart of a subject, the apparatus including an implant that includes:
a valve frame that includes a tubular portion that circumscribes a longitudinal axis of the valve frame so as to define a lumen along the axis, the tubular portion having an upstream end, a downstream end, a longitudinal length therebetween, and a diameter transverse to the longitudinal axis;
a valve member, coupled to the tubular portion, disposed within the lumen, and arranged to provide unidirectional upstream-to-downstream flow of blood through the lumen;
an upstream support portion, coupled to the tubular portion; and
an outer frame, coupled to the tubular portion, and including a tissue-engaging flange,
and:
the implant has a first state and a second state,
in both the first state and the second state, (i) the upstream support portion extends radially outward from the tubular portion, and (ii) the tissue-engaging flange extends radially outward from the tubular portion, and
the tubular portion, the upstream support portion, and the outer frame are arranged such that transitioning of the implant from the first state toward the second state:
increases the diameter of the tubular portion by a diameter-increase amount,
decreases the length of the tubular portion by a length-decrease amount, and
moves the flange a longitudinal distance toward or toward-and-beyond the upstream support portion, the distance being greater than the length-decrease amount.

In an application, the tubular portion, the upstream support portion, and the outer frame are arranged such that the longitudinal distance is more than 20 percent greater than the length-decrease amount.

In an application, the tubular portion, the upstream support portion, and the outer frame are arranged such that the longitudinal distance is more than 30 percent greater than the length-decrease amount.

In an application, the tubular portion, the upstream support portion, and the outer frame are arranged such that the longitudinal distance is more than 40 percent greater than the length-decrease amount.

There is further provided, in accordance with an application of the present invention, apparatus for use with a native valve that is disposed between an atrium and a ventricle of a heart of a subject, the apparatus including:
a valve frame, including a tubular portion that circumscribes a longitudinal axis of the valve frame so as to define a lumen along the axis;
a plurality of prosthetic leaflets, coupled to the frame, disposed within the lumen, and arranged to provide unidirectional flow of blood from an upstream end of the lumen to a downstream end of the lumen;
an outer frame, including:
a ring defined by a pattern of alternating peaks and troughs:
the peaks being longitudinally closer than the troughs to the upstream end,
the peaks being fixed to respective sites of the tubular portion at respective coupling points disposed circumferentially around the longitudinal axis, and
the pattern of the ring having an amplitude longitudinally between the peaks and the troughs; and
a plurality of legs, each of the legs coupled to the ring at a respective trough,
and:
the tubular portion has (i) a compressed state in which the tubular portion has a compressed diameter, and (ii) an expanded state in which the tubular portion has an expanded diameter that is greater than the compressed diameter, and
the fixation of the peaks to the respective sites of the tubular portion is such that compression of the tubular portion from the expanded state toward the compressed state such that the respective sites of the tubular portion pull the peaks radially inward via radially-inward tension on the coupling points: (i) reduces a circumferential distance between each of the coupling points and its adjacent coupling points, and (ii) increases the amplitude of the pattern of the ring.

In an application, the outer frame is coupled to the valve frame only via the fixation of the peaks to the respective sites of the tubular portion at the respective coupling points.

There is further provided, in accordance with an application of the present invention, apparatus for use with a native valve that is disposed between an atrium and a ventricle of a heart of a subject, the apparatus including:
a valve frame, including a tubular portion that circumscribes a longitudinal axis of the valve frame so as to define a lumen along the axis, the valve frame defining a plurality of valve-frame coupling elements disposed circumferentially around the longitudinal axis;
a plurality of prosthetic leaflets, coupled to the frame, disposed within the lumen, and arranged to provide unidirectional flow of blood from an upstream end of the lumen to a downstream end of the lumen;
an outer frame:
including a ring defined by a pattern of alternating peaks and troughs, the peaks being longitudinally closer to the upstream end than to the downstream end, and the troughs being longitudinally closer to the downstream end than to the upstream end, and the pattern of the ring having an amplitude longitudinally between the peaks and the troughs,
including a plurality of legs, each of the legs coupled to the ring at a respective trough, and
shaped to define a plurality of outer-frame coupling elements, each of the outer-frame coupling elements (i) coupled to the ring at a respective peak, and (ii) fixed with respect to a respective valve-frame coupling element,
and:
the tubular portion has (i) a compressed state in which the tubular portion has a compressed diameter, and (ii) an expanded state in which the tubular portion has an expanded diameter that is greater than the compressed diameter, and
the fixation of the outer-frame coupling elements with respect to the valve-frame coupling elements is such that compression of the tubular portion from the expanded state toward the compressed state (i) pulls the outer-frame coupling elements radially inward via radially-inward pulling of the valve-frame coupling elements on the outer-frame coupling elements, (ii) reduces a circumferential distance between each of the outer-frame coupling elements and its adjacent outer-frame coupling elements, and (iii) increases the amplitude of the pattern of the ring, without increasing a radial gap between the valve frame and the ring by more than 1.5 mm.

In an application, the outer frame is coupled to the valve frame only via the fixation of the outer-frame coupling elements to the respective valve-frame coupling elements.

There is further provided, in accordance with an application of the present invention, apparatus for use with a native valve that is disposed between an atrium and a ventricle of a heart of a subject, the apparatus including:
a valve frame, including a tubular portion that circumscribes a longitudinal axis of the valve frame so as to define a lumen along the axis;
a plurality of prosthetic leaflets, coupled to the frame, disposed within the lumen, and arranged to provide unidirectional flow of blood from an upstream end of the lumen to a downstream end of the lumen;
an outer frame, including:
a ring defined by a pattern of alternating peaks and troughs:
the peaks being longitudinally closer than the troughs to the upstream end,
the peaks being fixed to respective sites of the tubular portion at respective coupling points disposed circumferentially around the longitudinal axis, and
the pattern of the ring having an amplitude longitudinally between the peaks and the troughs; and
a plurality of legs, each of the legs coupled to the ring at a respective trough,
and:
the tubular portion has (i) a compressed state in which the tubular portion has a compressed diameter, and (ii) an expanded state in which the tubular portion has an expanded diameter that is greater than the compressed diameter, and
the fixation of the peaks to the respective sites of the tubular portion is such that compression of the tubular portion from the expanded state toward the compressed state (i) pulls the peaks radially inward via radially-inward pulling of the respective sites of the tubular portion on the peaks, (ii) reduces a circumferential distance between each of the coupling points and its adjacent coupling points, and (iii)

increases the amplitude of the pattern of the ring, without increasing a radial gap between the valve frame and the ring by more than 1.5 mm.

In an application, the outer frame is coupled to the valve frame only via the fixation of the peaks to the respective sites of the tubular portion at the respective coupling points.

There is further provided, in accordance with an application of the present invention, apparatus for use with a native valve disposed between an atrium and a ventricle of a heart of a subject, the apparatus including:

a valve frame, including a tubular portion that circumscribes a longitudinal axis of the valve frame so as to define a lumen along the axis, the tubular portion having an upstream end, a downstream end, and defining a plurality of valve-frame coupling elements disposed circumferentially around the longitudinal axis between the upstream end and the downstream end but not at the upstream end nor at the downstream end;

a plurality of prosthetic leaflets, disposed within the lumen, and arranged to provide unidirectional flow of blood through the lumen;

an outer frame:
including a ring defined by a pattern of alternating peaks and troughs, the peaks being longitudinally closer to the upstream end than to the downstream end, and the troughs being longitudinally closer to the downstream end than to the upstream end,
including a plurality of legs, each of the legs coupled to the ring at a respective trough, and
shaped to define a plurality of outer-frame coupling elements, each of the outer-frame coupling elements (i) coupled to the ring at a respective peak, and (ii) fixed with respect to a respective valve-frame coupling element at a respective coupling point, and:
the tubular portion has (i) a compressed state in which the tubular portion has a compressed diameter, and (ii) an expanded state in which the tubular portion has an expanded diameter that is greater than the compressed diameter, and
expansion of the tubular portion from the compressed state toward the expanded state (i) increases a circumferential distance between each of the outer-frame coupling elements and its adjacent outer-frame coupling elements, and (ii) moves the plurality of legs in a longitudinally upstream direction with respect to the tubular portion.

In an application, the outer frame is coupled to the valve frame only via the fixation of the outer-frame coupling elements to the respective valve-frame coupling elements.

There is further provided, in accordance with an application of the present invention, apparatus for use with a native valve disposed between an atrium and a ventricle of a heart of a subject, the apparatus including:

a valve frame, including a tubular portion that circumscribes a longitudinal axis of the valve frame so as to define a lumen along the axis, the tubular portion having an upstream end and a downstream end;

a plurality of prosthetic leaflets, disposed within the lumen, and arranged to provide unidirectional flow of blood through the lumen;

an outer frame, including:
a ring defined by a pattern of alternating peaks and troughs:
the peaks being longitudinally closer than the troughs to the upstream end,
the peaks being fixed to respective sites of the tubular portion at respective coupling points disposed circumferentially around the longitudinal axis between the upstream end and the downstream end but not at the upstream end nor the downstream end; and
a plurality of legs, each of the legs coupled to the ring at a respective trough, and:
the tubular portion has (i) a compressed state in which the tubular portion has a compressed diameter, and (ii) an expanded state in which the tubular portion has an expanded diameter that is greater than the compressed diameter, and
expansion of the tubular portion from the compressed state toward the expanded state (i) increases a circumferential distance between each of the coupling points and its adjacent coupling points, and (ii) moves the plurality of legs in a longitudinally upstream direction with respect to the tubular portion.

In an application, the outer frame is coupled to the valve frame only via the fixation of the peaks to the respective sites of the tubular portion at the respective coupling points.

There is further provided, in accordance with an application of the present invention, apparatus for use with a native valve of a heart of a subject, the apparatus including:

a frame assembly, having an upstream end and a downstream end, and a central longitudinal axis therebetween, and including:
a valve frame, including:
a tubular portion having an upstream end and a downstream end, and shaped to define a lumen therebetween, and
an upstream support portion, extending from the upstream end of the tubular portion; and
at least one leg, coupled to the valve frame at a coupling point, and having a tissue-engaging flange; and
a valve member disposed within the lumen, and configured to facilitate one-way liquid flow through the lumen from the upstream end of the tubular portion to the downstream end of the tubular portion,
and the frame assembly:
has a compressed state, for percutaneous delivery to the heart, in which the tubular portion has a compressed diameter,
is biased to assume an expanded state in which the tubular portion has an expanded diameter that is greater than the compressed diameter, and
is configured such that increasing the diameter of the tubular portion toward the expanded diameter causes longitudinal movement:
of the upstream support portion toward the coupling point, and
of the tissue-engaging flange away from the coupling point.

In an application:
the apparatus includes an implant that includes the frame assembly and the valve member, and
the apparatus further includes a tool:
including a delivery capsule dimensioned (i) to house and retain the implant in the compressed state, and (ii) to be advanced percutaneously to the heart of the subject while the implant is housed and in the compressed state, and
operable from outside the subject to facilitate an increase of the diameter of the tubular portion from the compressed diameter toward the expanded diameter such that the increase of the diameter actuates longitudinal movement:
of the upstream support portion toward the coupling point, and of the tissue-engaging flange away from the coupling point.

In an application, the frame assembly is configured such that increasing the diameter of the tubular portion by expanding the frame assembly toward the expanded state causes longitudinal movement of the upstream end of the tubular portion toward the coupling point.

In an application, the coupling point is disposed closer to the downstream end of the frame assembly than are either the tissue-engaging flange or the upstream support portion.

In an application, in the expanded state of the frame assembly, the leg extends away from the central longitudinal axis.

In an application:
the expanded state of the frame assembly is a fully-expanded state of the frame assembly,
the leg is expandable into an expanded state of the leg, independently of increasing the diameter of the tubular portion, and
in the expanded state of the leg, the leg extends away from the central longitudinal axis.

In an application:
in the expanded state of the frame assembly, the leg extends away from the central longitudinal axis, and
in the compressed state of the frame assembly, the leg is generally parallel with the central longitudinal axis.

In an application, the frame assembly is configured such that the longitudinal movement of the tissue-engaging flange away from the coupling point is a translational movement of the tissue-engaging flange that does not include rotation of the tissue-engaging flange.

In an application, the frame assembly is configured such that increasing the diameter of the tubular portion by expanding the frame assembly toward the expanded state causes 1-20 mm of longitudinal movement of the tissue-engaging flange away from the coupling point.

In an application, the frame assembly is configured such that increasing the diameter of the tubular portion by expanding the frame assembly toward the expanded state causes 1-20 mm of longitudinal movement of the upstream support portion toward the coupling point.

In an application, the frame assembly is configured such that increasing the diameter of the tubular portion by expanding the frame assembly toward the expanded state reduces a distance between the upstream support portion and the tissue-engaging flange by 5-30 mm.

In an application, the frame assembly is configured such that increasing the diameter of the tubular portion by expanding the frame assembly toward the expanded state moves the tissue-engaging flange longitudinally past the upstream support portion.

In an application:
the tubular portion is defined by a plurality of cells of the valve frame, and
increasing the diameter of the tubular portion by expanding the frame assembly toward the expanded state:
includes (i) increasing a width, orthogonal to the longitudinal axis of the frame assembly, of each cell, and (ii) reducing a height, parallel with the longitudinal axis of the frame assembly, of each cell, and
causes longitudinal movement of the upstream support portion toward the coupling point by reducing a height, parallel with the longitudinal axis of the frame assembly, of the tubular portion, by reducing the height of each cell.

In an application, the leg is disposed on an outside of the tubular portion.

In an application:
the at least one leg includes a plurality of legs,
the coupling point includes a plurality of coupling points, and
the frame assembly includes a leg frame that circumscribes the tubular portion, includes the plurality of legs, and is coupled to the valve frame at the plurality of coupling points, such that the plurality of legs is distributed circumferentially around the tubular portion.

In an application, the plurality of coupling points is disposed circumferentially around the frame assembly on a transverse plane that is orthogonal to the longitudinal axis of the frame assembly.

In an application, the plurality of legs is coupled to the valve frame via a plurality of struts, each strut:
having a first end that is coupled to a leg of the plurality of legs, and a second end that is coupled to a coupling point of the plurality of coupling points,
in the compressed state of the frame assembly, being disposed at a first angle in which the first end is disposed closer to the downstream end of the frame assembly than is the second end, and
being deflectable with respect to the coupling point of the plurality of coupling points, such that increasing the diameter of the tubular portion by expanding the frame assembly toward the expanded state causes the strut to deflect to a second angle in which the first end is disposed further from the downstream end of the frame assembly than is the first end in the compressed state of the frame assembly.

In an application, the leg frame is structured such that each leg of the plurality of legs is coupled to two struts of the plurality of struts, and two struts of the plurality of struts are coupled to each coupling point of the plurality of coupling points.

In an application, the leg is coupled to the valve frame via a strut, the strut:
having a first end that is coupled to the leg, and a second end that is coupled to the coupling point,
in the compressed state of the frame assembly, being disposed at a first angle in which the first end is disposed closer to the downstream end of the frame assembly than is the second end, and
being deflectable with respect to the coupling point, such that increasing the diameter of the tubular portion by expanding the frame assembly toward the expanded state causes the strut to deflect to a second angle in which the first end is disposed further from the downstream end of the frame assembly than is the first end in the compressed state of the frame assembly.

In an application, the at least one leg includes at least a first leg and a second leg.

In an application, the first leg and the second leg are both coupled to the valve frame at the coupling point.

In an application, the first leg is coupled to the coupling point via a respective first strut, and the second leg is coupled to the coupling point via a respective second strut.

In an application, the first and second legs, the first and second struts, and the coupling point are arranged such that, in the expanded state of the frame assembly:
the coupling point is disposed, circumferentially with respect to the tubular portion, between the first strut and the second strut,
the first strut is disposed, circumferentially with respect to the tubular portion, between the coupling point and the first leg, and the second strut is disposed, circumferentially with respect to the tubular portion, between the coupling point and the second leg.

In an application, the coupling point includes at least a first coupling point and a second coupling point.

In an application, the leg is coupled to the valve frame at the first coupling point and at the second coupling point.

In an application, the leg is coupled to the first coupling point via a respective first strut, and to the second coupling point via a respective second strut.

In an application, the first and second legs, the first and second struts, and the coupling point are arranged such that, in the expanded state of the frame assembly:

the leg is disposed, circumferentially with respect to the tubular portion, between the first strut and the second strut, the first strut is disposed, circumferentially with respect to the tubular portion, between the leg and the first coupling point, and the second strut is disposed, circumferentially with respect to the tubular portion, between the leg and the second coupling point.

In an application, in the expanded state of the frame assembly, the upstream support portion extends radially outward from the tubular portion.

In an application:

the expanded state of the frame assembly is a fully-expanded state of the frame assembly, the upstream support portion is expandable into an expanded state of the upstream support portion, independently of increasing the diameter of the tubular portion, and in the expanded state of the upstream support portion, the upstream support portion extends radially outward from the tubular portion.

In an application, in the compressed state of the frame assembly, the upstream support portion is generally tubular, collinear with the tubular portion, and disposed around the central longitudinal axis.

In an application, in the expanded state of the frame assembly, an inner region of the upstream support portion extends radially outward from the tubular portion at a first angle with respect to the tubular portion, and an outer region of the upstream support portion extends, from the inner region of the upstream support portion, further radially outward from the tubular portion at a second angle with respect to the tubular portion, the second angle being smaller than the first angle.

There is further provided, in accordance with an application of the present invention, apparatus for use with a native valve of a heart of a subject, the apparatus including:

a frame assembly, having an upstream end and a downstream end, and a central longitudinal axis therebetween, and including:

a valve frame, including:

a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly:

has a compressed state, for percutaneous delivery to the heart, in which the tubular portion has a compressed diameter, is biased to assume an expanded state in which the tubular portion has an expanded diameter that is greater than the compressed diameter, and is configured such that reducing the diameter of the tubular portion toward the compressed diameter causes longitudinal movement:

of the upstream support portion away from the coupling point, and of the tissue-engaging flange toward the coupling point.

There is further provided, in accordance with an application of the present invention, apparatus for use with a native valve of a heart of a subject, the apparatus including:

a frame assembly, having an upstream end and a downstream end, and a central longitudinal axis therebetween, including:

a valve frame, including:

a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly:

has a compressed state, for percutaneous delivery to the heart, is intracorporeally expandable into an expanded state in which a diameter of the tubular portion is greater than in the compressed state, and is configured such that increasing the diameter of the tubular portion by expanding the frame assembly toward the expanded state causes longitudinal movement of the tissue-engaging flange away from the coupling point.

There is further provided, in accordance with an application of the present invention, apparatus for use with a native valve of a heart of a subject, the apparatus including:

a frame assembly, having an upstream end and a downstream end, and a central longitudinal axis therebetween, and including:

an inner frame including an inner-frame tubular portion that circumscribes the central longitudinal axis, has an upstream end and a downstream end, and defines a channel therebetween, the inner frame defining a plurality of inner-frame couplings disposed circumferentially at a longitudinal location of the inner frame, an outer frame including an outer-frame tubular portion that coaxially circumscribes at least a portion of the inner-frame tubular portion, the outer frame defining a plurality of outer-frame couplings disposed circumferentially at a longitudinal location of the outer frame, and a plurality of connectors, each connector connecting a respective inner-frame coupling to a respective outer-frame coupling;

a liner, disposed over at least part of the inner-frame tubular portion; and a plurality of prosthetic leaflets, coupled to the inner-frame tubular portion and disposed within the channel, and:

the frame assembly: (i) is compressible by a radially-compressive force into a compressed state in which the inner frame is in a compressed state thereof and the outer frame is in a compressed state thereof, (ii) is configured, upon removal of the radially-compressive force, to automatically expand into an expanded state thereof in which the inner frame is in an expanded state thereof and the outer frame is in an expanded state thereof, in the expanded state of the frame assembly, the prosthetic leaflets are configured to facilitate one-way fluid flow, in a downstream direction, through the channel, and the connection of the inner-frame couplings to the respective outer-frame couplings is such that expansion of the frame assembly from the compressed state to the expanded state causes the inner-frame tubular portion to slide longitudinally in a downstream direction with respect to the outer-frame tubular portion.

There is further provided, in accordance with an application of the present invention, apparatus for use with a native valve disposed between an atrium and a ventricle of a heart of a subject, the apparatus including:

a tubular portion, having an upstream portion that includes an upstream end, and a downstream portion that includes a downstream end, and shaped to define a lumen between the upstream portion and the downstream portion;

a plurality of prosthetic leaflets, disposed within the lumen, and arranged to provide unidirectional flow of blood from the upstream portion to the downstream portion;

an annular upstream support portion:

having an inner portion that extends radially outward from the upstream portion, and including one or more fabric pockets disposed circumferentially around the inner portion, each pocket of the one or more pockets having an opening that faces a downstream direction.

In an application:

the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, at the inner portion of the upstream support portion, the covering is closely-fitted between the radially-inner parts of the arms, and at the outer portion of the upstream support portion, the pockets are formed by the covering being loosely-fitted between the radially-outer parts of the arms.

In an application:

the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, the radially-outer part being more flexible than the radially-inner part.

In an application:

the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, at the outer portion of the upstream support portion, the pockets are formed by each arm curving to form a hook shape.

In an application, each pocket is shaped and arranged to billow in response to perivalvular flow of blood in an upstream direction.

In an application, the apparatus is configured to be transluminally delivered to the heart, and implanted at the native valve by expansion of the apparatus, such that the upstream support portion is disposed in the atrium and the tubular portion extends from the upstream support portion into the ventricle, and each pocket is shaped and arranged such that perivalvular flow of blood in an upstream direction presses the pocket against tissue of the atrium.

There is further provided, in accordance with an application of the present invention, apparatus including:

a plurality of prosthetic valve leaflets; and a frame assembly, including:

a tubular portion defined by a repeating pattern of cells, the tubular portion extending circumferentially around a longitudinal axis so as to define a longitudinal lumen, the prosthetic valve leaflets coupled to the inner frame and disposed within the lumen;

an outer frame, including a plurality of legs, distributed circumferentially around the tubular portion, each leg having a tissue-engaging flange;

an upstream support portion that includes a plurality of arms that extend radially outward from the tubular portion; and a plurality of appendages, each having a first end that defines a coupling element via which the tubular portion is coupled to the outer frame, and a second end;

and the frame assembly defines a plurality of hubs, distributed circumferentially around the longitudinal axis on a plane that is transverse to the longitudinal axis, each hub defined by convergence and connection of, (i) two adjacent cells of the tubular portion, (ii) an arm of the plurality of arms, and (iii) an appendage of the plurality of appendages.

In an application, each hub has six radiating spokes, two of the six spokes being part of a first cell of the two adjacent cells, two of the six spokes being part of a second cell of the two adjacent cells, one of the six spokes being the arm, and one of the six spokes being the second end of the appendage.

In an application, the appendages are in-plane with the tubular portion.

In an application, the appendages are in-plane with the outer frame.

There is further provided, in accordance with an application of the present invention, a method for use with a native valve of a heart of a subject, the method including:

percutaneously advancing to heart, an implant:

including a valve frame, a valve member disposed within a lumen defined by the valve frame, and at least one leg, coupled to the valve frame at a coupling point, and having an upstream end, a downstream end, and a central longitudinal axis therebetween;

positioning the implant within the heart such that a tissue-engaging flange of the leg is disposed downstream of the valve, and thereafter causing the flange to protrude radially outward from the axis;

subsequently, while an upstream support portion of the valve frame is disposed upstream of the valve, causing the upstream support portion to protrude radially outward from the axis, such that tissue of the valve is disposed between the upstream support portion and the flange; and subsequently, sandwiching the tissue between the upstream support portion and the flange by reducing a distance between the upstream support portion and the flange by causing longitudinal movement (i) of the upstream support portion toward the coupling point, and (ii) of the tissue-engaging flange away from the coupling point.

In an application, causing the longitudinal movement (i) of the upstream support portion toward the coupling point, and (ii) of the tissue-engaging flange away from the coupling point, includes causing the longitudinal movement by increasing a diameter of the lumen.

There is further provided, in accordance with an application of the present invention, a method for use with a native valve of a heart of a subject, the method including:

percutaneously advancing to heart, an implant:
including a valve frame, a valve member disposed within a lumen defined by the valve frame, and at least one leg, coupled to the valve frame at a coupling point, and
having an upstream end, a downstream end, and a central longitudinal axis therebetween;
positioning the implant within the heart such that an upstream support portion of the valve frame is disposed upstream of the valve, and thereafter causing the upstream support portion to protrude radially outward from the axis;
subsequently, while a tissue-engaging flange of the leg is disposed downstream of the valve, causing the tissue-engaging flange to protrude radially outward from the axis, such that tissue of the valve is disposed between the upstream support portion and the flange; and
subsequently, sandwiching the tissue between the upstream support portion and the flange by reducing a distance between the upstream support portion and the flange by causing longitudinal movement (i) of the upstream support portion toward the coupling point, and (ii) of the tissue-engaging flange away from the coupling point.

In an application, causing the longitudinal movement (i) of the upstream support portion toward the coupling point, and (ii) of the tissue-engaging flange away from the coupling point, includes causing the longitudinal movement by increasing a diameter of the lumen.

There is further provided, in accordance with an application of the present invention, a method for use with a native valve of a heart of a subject, the method including:

percutaneously advancing an implant to the heart, the implant:
having an upstream end, a downstream end, and a central longitudinal axis therebetween, and
including a tubular portion, an upstream support portion, and a plurality of tissue-engaging flanges;
positioning the implant within the heart such that the upstream support portion is disposed upstream of the valve,
positioning the implant within the heart such that the tissue-engaging flanges are disposed downstream of the valve,
without increasing a diameter of the tubular portion:
causing the upstream support portion to extend radially outward from the axis so as to have a first support-portion span, and
causing the flanges to extend radially outward from the axis so as to have a first flange span; and
subsequently, causing the upstream support portion and the flanges move toward each other by at least 5 mm by increasing a diameter of the tubular portion such that:
the upstream support portion extends radially outward so as to have a second support-portion span, the first support-portion span being at least 40 percent as great as the second support-portion span, and
the flanges extend radially outward so as to have a second flange span, the first flange span being at least 30 percent as great as the second flange span.

There is further provided, in accordance with an application of the present invention, a method for use with a native valve of a heart of a subject, the method including:

percutaneously advancing an implant to the heart, the implant:
having an upstream end, a downstream end, and a central longitudinal axis therebetween, and
including a tubular portion, an upstream support portion, and a plurality of tissue-engaging flanges;
positioning the implant within the heart such that the upstream support portion is disposed upstream of the valve,
positioning the implant within the heart such that the tissue-engaging flanges are disposed downstream of the valve,
without increasing a diameter of the tubular portion:
causing the upstream support portion to extend radially outward from the axis, and
causing the flanges to extend radially outward from the axis so as to have a first flange span; and
subsequently, by increasing a diameter of the tubular portion:
causing the upstream support portion and the flanges move toward each other by at least 5 mm,
causing the upstream support portion to move further radially outward from the axis, and
causing each flange of the plurality of flanges to translate radially outward so as to have a second flange span that is greater than the first flange span.

The present invention will be more fully understood from the following detailed description of applications thereof, taken together with the drawings, in which:

BRIEF DESCRIPTION OF THE DRAWINGS

FIGS. 1A-B and 2A-H are schematic illustrations of an implant for use with a native valve of a heart of a subject, in accordance with some applications of the invention;

FIGS. 3A-C are schematic illustrations that show structural changes in a frame assembly during transitioning of the assembly between its compressed and expanded states, in accordance with some applications of the invention;

FIGS. 4A-F are schematic illustrations of implantation of the implant at the native valve, in accordance with some applications of the invention;

FIG. 5 is a schematic illustration of a step in the implantation of the implant, in accordance with some applications of the invention;

FIGS. 7A-B and 8A-B are schematic illustrations of frame assemblies of respective implants, in accordance with some applications of the invention; and FIGS. 9A-C are schematic illustrations of an implant comprising a frame assembly, in accordance with some applications of the invention.

DETAILED DESCRIPTION OF EMBODIMENTS

Figure 1B:
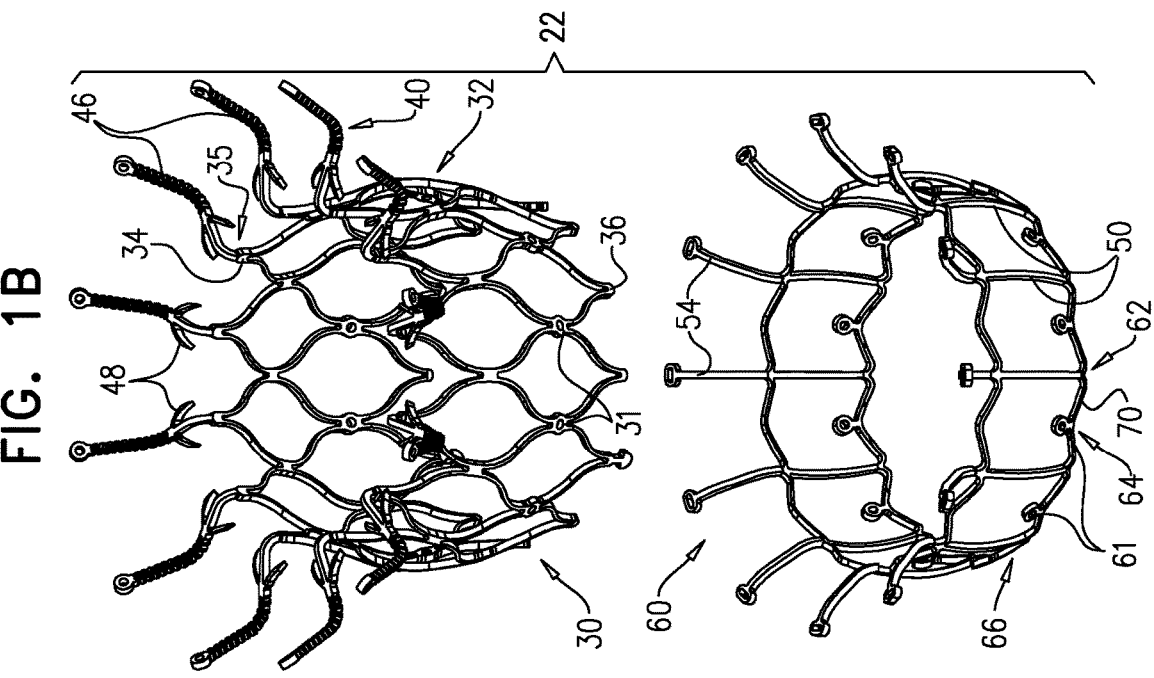

Reference is made to FIGS. 1A-B and 2A-H, which are schematic illustrations of an implant 20 for use with a native valve of a heart of a subject, in accordance with some applications of the invention. Implant 20 comprises a frame assembly 22 that has an upstream end 24, a downstream end 26, and a central longitudinal axis ax1 therebetween. Frame assembly 22 comprises a valve frame 30 that comprises a tubular portion 32 that has an upstream end 34 and a downstream end 36, and is shaped to define a lumen 38 through the tubular portion from the upstream end to the downstream end. Tubular portion 32 circumscribes axis ax1, and thereby defines lumen 38 along the axis. Valve frame 30 further comprises an upstream support portion 40, extending from upstream end 34 of tubular portion 32. Frame assembly 22 further comprises at least one leg 50, coupled to valve frame 30 at (e.g., via) a coupling point 52, and having a tissue-engaging flange 54.

Typically, and as described hereinbelow, leg 50 is part of an outer frame (or "leg frame") 60, and frames 30 and 60 define respective coupling elements 31 and 61, which are fixed with respect to each other at coupling points 52. Typically, frames 30 and 60 are coupled to each other only at coupling points 52 (e.g., only via the fixation of coupling elements 31 and 61 with respect to each other).

Figure 1A:
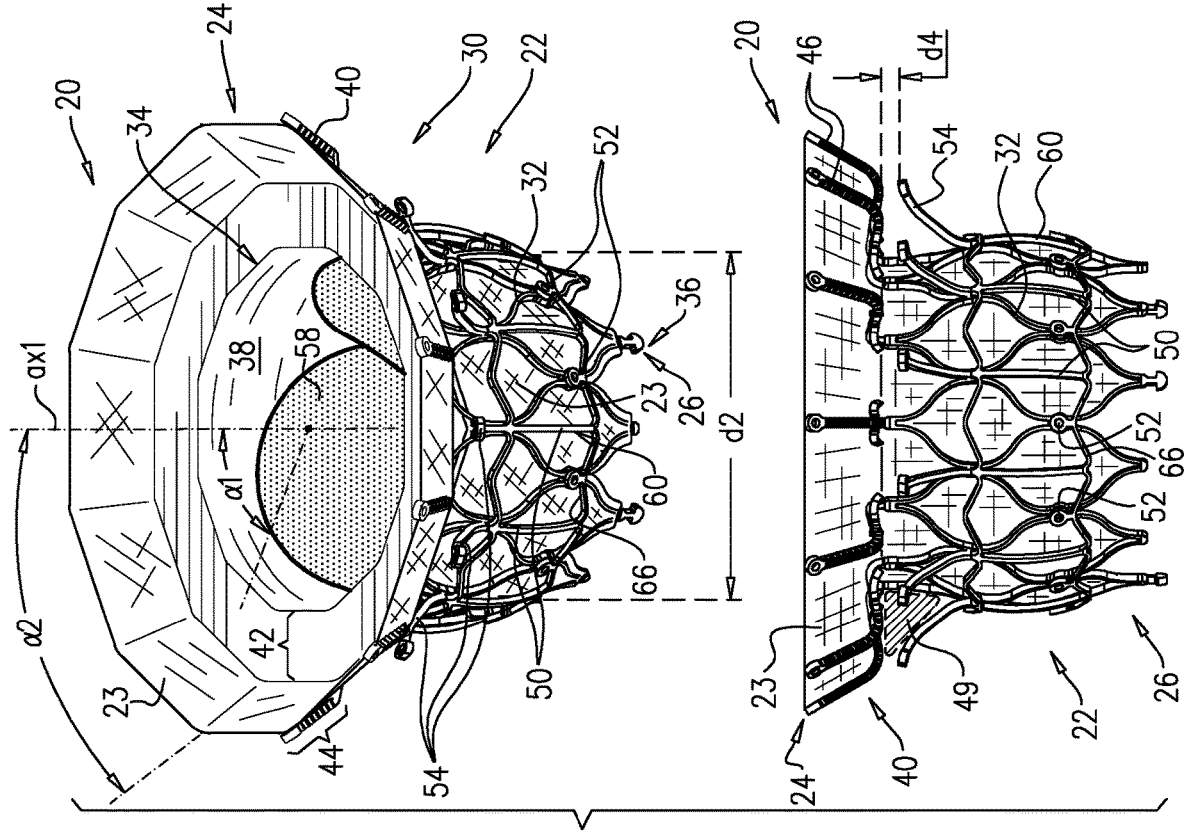
Figure 2F:
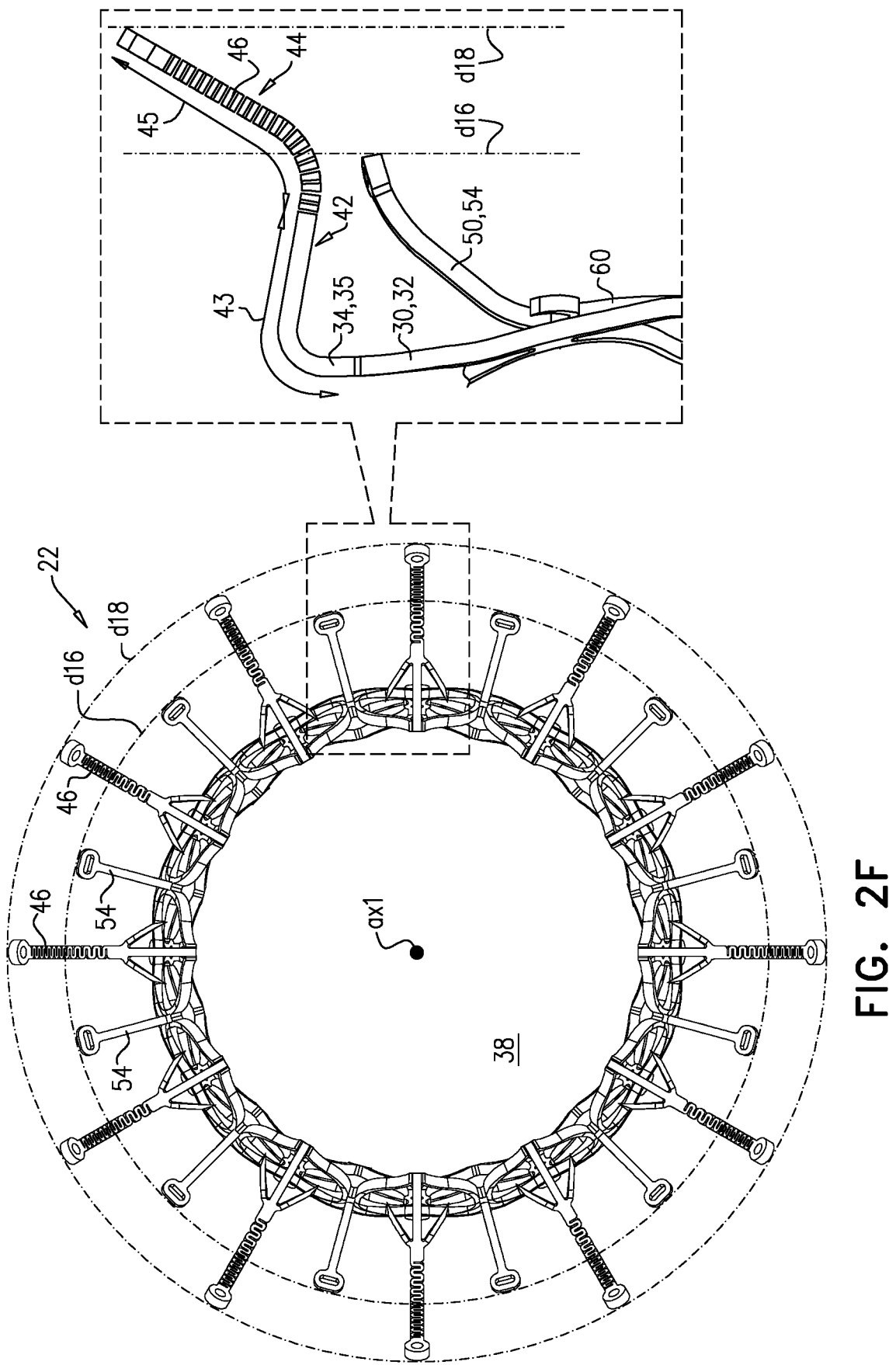

Implant 20 further comprises a valve member 58 (e.g., one or more prosthetic leaflets) disposed within lumen 38, and configured to facilitate one-way liquid flow through the lumen from upstream end 34 to downstream end 36 (e.g., thereby defining the orientation of the upstream and downstream ends of tubular portion 32). FIG. 1A shows implant 20 in a fully-expanded state, in which frame assembly 22 is in a fully-expanded state. FIG. 1B shows an exploded view of frame assembly 22 in its fully-expanded state. FIGS. 2A-E show respective states of implant 20, which will be discussed in more detail hereinbelow with respect to the implantation of the implant and the anatomy in which the implant is implanted. FIG. 2A shows implant 20 in a compressed state (in which frame assembly 22 is in a compressed state), for percutaneous delivery of the implant to the heart of the subject. Typically, in the compressed state, leg 50 (including flange 54 thereof) is in a constrained-flange state in which the flange is generally parallel with axis ax1. Further typically, in the compressed state, upstream support portion 40 is generally tubular, collinear with tubular portion 32 (e.g., extending collinearly from the tubular portion), and disposed around axis ax1.

FIG. 2B shows a state of implant 20 in which tissue-engaging flange 54 of each leg 50 extends radially away from axis ax1 (e.g., radially away from tubular portion 32). FIG. 2C shows a state of implant 20 in which upstream-support portion 40 extends radially away from axis ax1 (and thereby radially away from tubular portion 32). FIG. 2D shows a state of implant 20 in which both flange 54 and portion 40 extend away from axis ax1. In the fully-expanded state (FIGS. 1A-B) both upstream support portion 40 and flange 54 extend radially away from axis ax1. Typically, frame assembly 22 is biased (e.g., shape-set) to assume its fully-expanded state, which is shown in FIG. 2E. Transitioning of implant 20 between the respective states is typically controlled by delivery apparatus, such as by constraining the implant in a compressed state within a delivery tube and/or against a control rod, and selectively releasing portions of the implant to allow them to expand.

In the compressed state of frame assembly 22, tubular portion 32 has a diameter d1, and in the expanded state, the tubular portion has a diameter d2 that is greater that diameter d1. For some applications, diameter d1 is 4-15 mm, (e.g., 5-11 mm) and diameter d2 is 20-50 mm, (e.g., 23-33 mm). Frame assembly 22 is configured such that increasing the diameter of tubular portion 32 (e.g., from d1 to d2) causes longitudinal movement of flange 54 away from coupling point 52. In the same way, reducing the diameter of tubular portion 32 (e.g., from d2 to d1) causes longitudinal movement of flange 54 toward coupling point 52. It is to be noted that the term "longitudinal movement" (including the specification and the claims) means movement parallel with central longitudinal axis ax1. Therefore, longitudinal movement of flange 54 away from coupling point 52 means increasing a distance, measured parallel with longitudinal axis ax1, between flange 54 and coupling point 52. An example of such a configuration is described in more detail with respect to FIG. 3A.

Thus, expansion of tubular portion 32 from its compressed state toward its expanded state (i) increases a circumferential distance between each of coupling points 52 and its adjacent coupling points (e.g., between each of outer-frame coupling elements 61 and its adjacent outer-frame coupling elements) (e.g., from d8 to d9), and (ii) moves legs 50 in a longitudinally upstream direction with respect to the tubular portion.

Figure 3C:
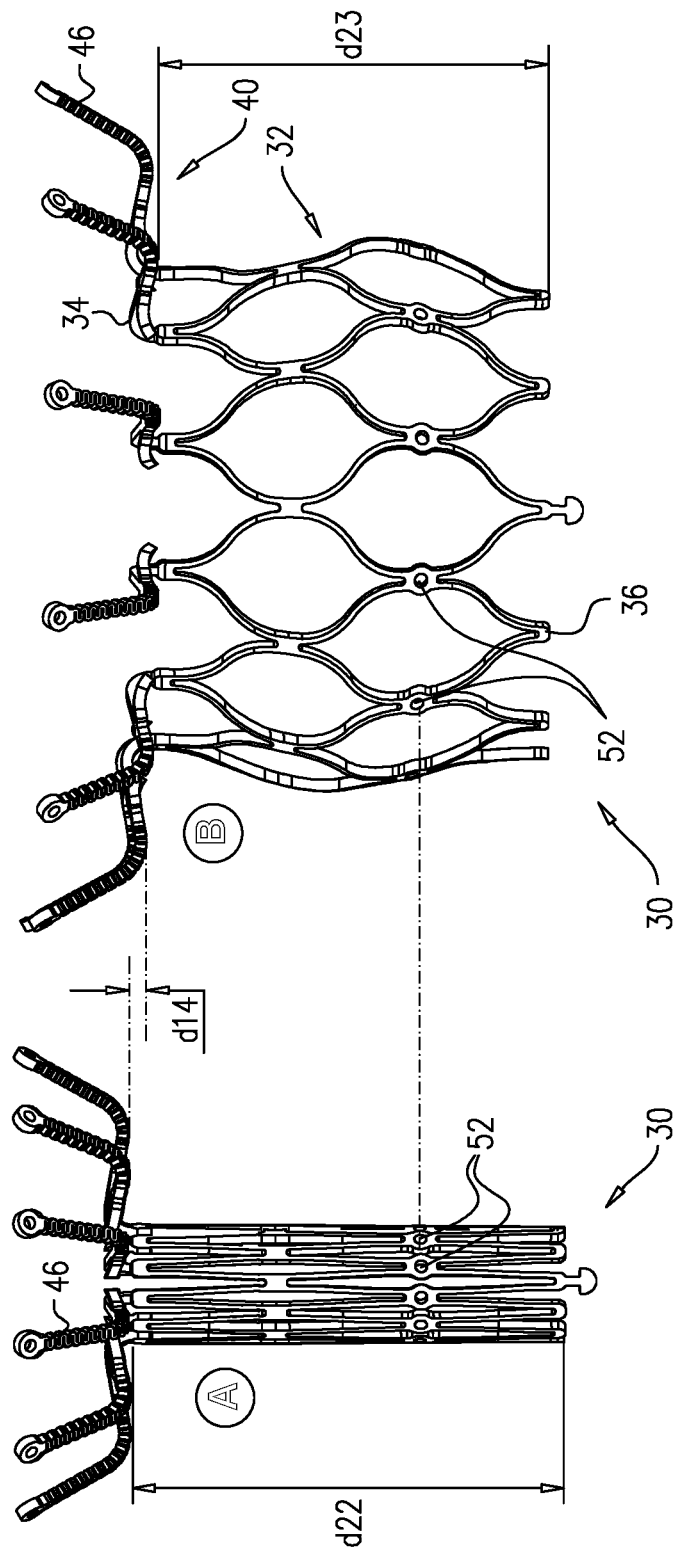

Typically, frame assembly 22 is configured such that increasing the diameter of tubular portion 32 also causes longitudinal movement of upstream support portion 40 toward coupling point 52, e.g., as described in more detail with respect to FIGS. 3B-C. Typically, frame assembly 22 is configured such that increasing the diameter of tubular portion 32 also causes longitudinal movement of upstream end 34 of tubular portion 32 toward coupling point 52. In the same way, reducing the diameter of tubular portion 32 causes longitudinal movement of upstream end 34 away from coupling point 52.

For some applications, upstream support portion 40 comprises a plurality of arms 46 that each extends radially outward from tubular portion 32 (e.g., from upstream end 34 of the tubular portion). Arms 46 are typically flexible. For some such applications, arms 46 are coupled to tubular portion 32 such that each arm may deflect independently of adjacent arms during implantation (e.g., due to anatomical topography).

For some applications, upstream support portion 40 comprises a plurality of barbs 48 that extend out of a downstream surface of the upstream support portion. For example, each arm 46 may comprise one or more of barbs 48. Barbs 48 press into tissue upstream of the native valve (e.g., into the valve annulus), thereby inhibiting downstream movement of implant 20 (in addition to inhibition of downstream movement provided by the geometry of upstream support portion 40).

One or more surfaces of frame assembly 22 are covered with a covering 23, which typically comprises a flexible sheet, such as a fabric, e.g., comprising polyester. Typically, covering 23 covers at least part of tubular portion 32, typically lining an inner surface of the tubular portion, and thereby defining lumen 38.

Further typically, upstream support portion 40 is covered with covering 23, e.g., extending between arms 46 to form an annular shape. It is hypothesized that this reduces a likelihood of paravalvular leakage. For such applications, excess covering 23 may be provided between arms 46 of upstream support portion 40, so as to facilitate their independent movement. Although FIG. 1A shows covering 23 covering an upstream side of upstream support portion 40, the covering typically additionally (or alternatively) covers the downstream side of the upstream support portion. For example, covering 23 may extend over the tips of arms 46 and down the outside of the arms, or a separate piece of covering may be provided on the downstream side of the upstream support portion.

Alternatively, each arm 46 may be individually covered in a sleeve of covering 23, thereby facilitating independent movement of the arms.

For some applications, at least part of legs 50 (e.g., flanges thereof) is covered with covering 23.

Typically, frame assembly 22 comprises a plurality of legs 50 (e.g., two or more legs, e.g., 2-16 legs, such as 4-12 legs, such as 6-12 legs), arranged circumferentially around valve frame 30 (e.g., around the outside of tubular portion 32). Typically, frame assembly 22 comprises a plurality of coupling points 52 at which the legs are coupled to valve frame 30.

As described in more detail hereinbelow (e.g., with reference to FIG. 3A), each leg 50 is typically coupled to a coupling point 52 via a strut 70. For some applications, each leg 50 is coupled to a plurality of (e.g., two) coupling points 52 via a respective plurality of (e.g., two) struts 70. For some such applications, frame assembly 22 is arranged such that, in the expanded state of the frame assembly, leg 50 is disposed, circumferentially with respect to tubular portion 32, between two struts, and each of the two struts are disposed, circumferentially with respect to the tubular portion, between the leg and a respective coupling point 52.

For some applications, a plurality of (e.g., two) legs are coupled to each coupling point 52 via a respective plurality of (e.g., two) struts 70. For some such applications, frame assembly 22 is arranged such that, in the expanded state of the frame assembly, coupling point 52 is disposed, circumferentially with respect to tubular portion 32, between two struts 70, and each of the two struts are disposed, circumferentially with respect to the tubular portion, between the coupling point and a respective leg 50.

For some applications, frame assembly 22 comprises an outer frame (e.g., a leg frame) 60 that circumscribes tubular portion 32, comprises (or defines) the plurality of legs 50 and the plurality of struts 70, and is coupled to valve frame 30 at the plurality of coupling points 52, such that the plurality of legs is distributed circumferentially around the tubular portion. For such applications, outer frame 60 comprises a ring 66 that is defined by a pattern of alternating peaks 64 and troughs 62, and that typically circumscribes tubular portion 32. For example, the ring may comprise struts 70, extending between the peaks and troughs. Peaks 64 are longitudinally closer to upstream end 34 of tubular portion 32 than to downstream end 36, and troughs 62 are longitudinally closer to the downstream end than to the upstream end. (It is to be noted that throughout this patent application, including the specification and the claims, the term "longitudinally" means with respect to longitudinal axis ax1. For example, "longitudinally closer" means closer along axis ax1 (whether positioned on axis ax1 or lateral to axis ax1), and "longitudinal movement" means a change in position along axis ax1 (which may be in additional to movement toward or away from axis ax1).) Therefore, peaks 64 are closer than troughs 62 to upstream end 34, and troughs 62 are closer than peaks 64 to downstream end 36. For applications in which frame 60 comprises ring 66, each leg 50 is coupled to the ring (or defined by frame 60) at a respective trough 62.

In the embodiment shown, the peaks and troughs are defined by ring 66 having a generally zig-zag shape. However, the scope of the invention includes ring 66 having another shape that defines peaks and troughs, such as a serpentine or sinusoid shape.

For applications in which frame assembly 22 has a plurality of coupling points 52, the coupling points (and therefore coupling elements 31 and 61) are disposed circumferentially around the frame assembly (e.g., around axis ax1), typically on a transverse plane that is orthogonal to axis ax1. This transverse plane is illustrated by the position of section A-A in FIG. 2B. Alternatively, coupling points 52 may be disposed at different longitudinal heights of frame assembly 22, e.g., such that different flanges 54 are positioned and/or moved differently to others.

Typically, coupling points 52 (and therefore coupling elements 31 and 61) are disposed longitudinally between upstream end 24 and downstream end 26 of frame assembly 22, but not at either of these ends. Further typically, coupling points 52 are disposed longitudinally between upstream end 34 and downstream end 36 of tubular portion 32, but not at either of these ends. For example, the coupling points may be more than 3 mm (e.g., 4-10 mm) both from end 34 and from end 36. It is hypothesized that this advantageously positions the coupling points at a part of tubular portion 32 that is more rigid than end 34 or end 36.

It is to be noted that leg 50 is typically expandable into its expanded state (e.g., a released-flange state) such that flange 54 extends away from axis ax1, independently of increasing the diameter of tubular portion 32 (e.g., as shown in FIGS. 2B & 2D). Similarly, upstream support portion 40 is typically expandable into its expanded state (e.g., a released-arm state) such that it (e.g., arms 46 thereof) extends away from axis ax1, independently of increasing the diameter of tubular portion 32 (e.g., as shown in FIG. 2C & 2D). The state shown in FIG. 2D may be considered to be an intermediate state. Therefore, implant 20 is typically configured such that legs 50 (e.g., flanges 54 thereof) and upstream support portion 40 are expandable such that they both extend away from axis ax1, while retaining a distance d3 therebetween. This distance is subsequently reducible to a distance d4 by expanding tubular portion 32 (e.g., shown in FIG. 2E).

For some applications, while tubular portion 32 remains in its compressed state, flange 54 can extend away from axis ax1 over 40 percent (e.g., 40-80 percent, such as 40-70 percent) of the distance that it extends from the axis subsequent to the expansion of the tubular portion. For example, for applications in which implant 20 comprises a flange on opposing sides of the implant, a span d15 of the flanges while tubular portion 32 is in its compressed state may be at least 40 percent (e.g., 40-80 percent, such as 40-70 percent) as great as a span d16 of the flanges subsequent to the expansion of the tubular portion. For some applications, span d15 is greater than 15 mm and/or less than 50 mm (e.g., 20-30 mm). For some applications, span d16 is greater than 30 mm and/or less than 60 mm (e.g., 40-50 mm). It is to be noted that flange 54 is effectively fully expanded, with respect to other portions of leg 50 and/or with respect to tubular portion 32, before and after the expansion of the tubular portion.

Similarly, for some applications, while tubular portion 32 remains in its compressed state, upstream support portion 40 (e.g., arms 46) can extend away from axis ax1 over 30 percent (e.g., 30-70 percent) of the distance that it extends from the axis subsequent to the expansion of the tubular portion. That is, for some applications, a span d17 of the upstream support portion while tubular portion 32 is in its compressed state may be at least 30 percent (e.g., 30-70 percent) as great as a span d18 of the upstream support portion subsequent to the expansion of the tubular portion. For some applications, span d17 is greater than 16 mm (e.g., greater than 20 mm) and/or less than 50 mm (e.g., 30-40 mm). For some applications, span d18 is greater than 40 mm and/or less than 65 mm (e.g., 45-56 mm, such as 45-50 mm).

It is to be noted that upstream support portion 40 is effectively fully expanded, with respect to tubular portion 32, before and after the expansion of the tubular portion.

It is to be noted that when tubular portion 32 is expanded, flanges 54 typically translate radially outward from span d15 to span d16 (e.g., without deflecting). Typically, upstream support portion 40 behaves similarly (e.g., arms 46 translated radially outward from span d17 to span d18, e.g., without deflecting). That is, an orientation of each flange 54 and/or each arm 46 with respect to tubular portion 32 and/or axis ax1 is typically the same in the state shown in FIG. 2D as it is in the state shown in FIG. 2E. Similarly, for some applications an orientation of each flange 54 with respect to upstream support portion 40 (e.g., with respect to one or more arms 46 thereof) is the same before and after expansion of tubular portion 32.

For some applications, increasing the diameter of tubular portion 32 from d1 to d2 causes greater than 1 mm and/or less than 20 mm (e.g., 1-20 mm, such as 1-10 mm or 5-20 mm) of longitudinal movement of flange 54 away from coupling point 52. For some applications, increasing the diameter of tubular portion 32 from d1 to d2 causes greater than 1 mm and/or less than 20 mm (e.g., 1-20 mm, such as 1-10 mm or 5-20 mm) of longitudinal movement of upstream support portion 40 toward coupling point 52. For some applications, distance d3 is 7-30 mm. For some applications, distance d4 is 0-15 mm (e.g., 2-15 mm). For some applications, increasing the diameter of tubular portion 32 from d1 to d2 reduces the distance between the upstream support portion and flanges 54 by more than 5 mm and/or less than 30 mm, such as 5-30 mm (e.g., 10-30 mm, such as 10-20 mm or 20-30 mm). For some applications, the difference between d3 and d4 is generally equal to the difference between d1 and d2. For some applications, the difference between d3 and d4 is more than 1.2 and/or less than 3 times (e.g., 1.5-2.5 times, such as about 2 times) greater than the difference between d1 and d2.

For some applications, flanges 54 curve such that a tip of each flange is disposed at a shallower angle with respect to inner region 42 of upstream support portion 40, than are portions of leg 50 that are closer to downstream end 26 of frame assembly 22. For some such applications, a tip of each flange may be generally parallel with inner region 42. For some such applications, while tubular portion 32 is in its expanded state, a tip portion 55 of each flange 54 that extends from the tip of the flange at least 2 mm along the flange, is disposed within 2 mm of upstream support portion 40. Thus, for some applications, while tubular portion 32 is in its expanded state, for at least 5 percent (e.g., 5-8 percent, or at least 8 percent) of span 18 of upstream support portion 40, the upstream support portion is disposed within 2 mm of a flange 54.

For some applications, in the absence of any obstruction (such as tissue of the valve or covering 23) between flange 54 and upstream support portion 40, increasing the diameter of tubular portion 32 from d1 to d2 causes the flange and the upstream support portion to move past each other (e.g., the flange may move between arms 46 of the upstream support portion), such that the flange is closer to the upstream end of implant 20 than is the upstream support portion, e.g., as shown hereinbelow for frame assemblies 122 and 222, mutatis mutandis. (For applications in which upstream support portion 40 is covered by covering 23, flanges 54 typically don't pass the covering. For example, in the absence of any obstruction, flanges 54 may pass between arms 46, and press directly against covering 23.) It is hypothesized that for some applications this configuration applies greater force to the valve tissue being sandwiched, and thereby further facilitates anchoring of the implant. That is, for some applications, distance d3 is smaller than the sum of distance d5 and a distance d14 (described with reference to FIG. 3C). For some applications, increasing the diameter of tubular portion 32 from d1 to d2 advantageously causes flanges 54 and upstream support portion 40 to move greater than 3 mm and/or less than 25 mm (e.g., greater than 5 mm and/or less than 15 mm, e.g., 5-10 mm, such as about 7 mm) with respect to each other (e.g., toward each other and then past each other).

For some applications, in the expanded state of frame assembly 22, upstream support portion 40 has an inner region (e.g., an inner ring) 42 that extends radially outward at a first angle with respect to axis ax1 (and typically with respect to tubular portion 32), and an outer region (e.g., an outer ring) 44 that extends, from the inner region, further radially outward from the tubular portion at a second angle with respect to the tubular portion, the second angle being smaller than the first angle. For example, for some applications inner region 42 extends radially outward at an angle alpha_1 of 60-120 degrees (e.g., 70-110 degrees) with respect to axis ax1, and outer region 44 extends radially outward at an angle alpha_2 of 5-70 degrees (e.g., 10-60 degrees) with respect to axis ax1.

It is to be noted that angles alpha_1 and alpha_2 are measured between the respective region support portion 40, and the portion of axis ax1 that extends in an upstream direction from the level of frame assembly 22 at which the respective region begins to extend radially outward.

For some applications in which implant 20 is configured to be placed at an atrioventricular valve (e.g., a mitral valve or a tricuspid valve) of the subject, region 42 is configured to be placed against the upstream surface of the annulus of the atrioventricular valve, and region 44 is configured to be placed against the walls of the atrium upstream of the valve.

For some applications, each arm 46 defines a rigid portion 43 and a flexible portion 45 that is disposed radially outward from the rigid portion, and is more flexible than the rigid portion. Typically, at least part of flexible portion 45 is disposed in outer region 44, and at least part of rigid portion 43 is disposed in inner region 42. Therefore, typically overall, outer region 44 is more flexible than inner region 42. To achieve this differential flexibility, each arm 46 may have a different structure in portion 45 and/or region 44, than it has in portion 43 and/or region 42.

FIG. 2G shows an arm 46a, which is a variant of arm 46. Arm 46a defines flexible portion 45a, which is a variant of flexible portion 45. In flexible portion 45a, the material from which arm 46a is formed is thinner than in rigid portion 43, but defines a serpentine or zig-zag pattern that increases the overall thickness of portion 45a, and as shown, may make the overall thickness of portion 45a equal to or greater than the overall thickness of portion 43.

FIG. 2H shows an arm 46b, which is a variant of arm 46. Arm 46b defines flexible portion 45b, which is a variant of flexible portion 45. In flexible portion 45b, arm 46b defines holes 47 in the material from which arm 46b is formed. Nonetheless, as shown, the overall thickness of portion 45b may be equal to or greater than the overall thickness of portion 43.

Therefore, as shown for arms 46a and 46b, flexible portion 45 covers an overall surface area including (i) the area in which the material from which the arm is formed occupies, and (ii) spaces, such as holes, or gaps between turns. For some applications, the material from which the arm is formed occupies less than 80 percent and/or more than 20 percent of the overall surface area (e.g., 20-80 percent, e.g., 40-80 percent, e.g., 40-70 percent of the overall surface area).

It is hypothesized that the relative rigidity of portion 43 and/or region 42 provides resistance against axial movement (e.g., ventricular migration) of implant 20, while the relative flexibility of portion 45 and/or region 44 facilitates conformation of upstream support portion 40 to the atrial anatomy and/or lateral movement of the implant within the native valve.

For some applications, and as shown (e.g., in FIGS. 1A and 2E-F), in the expanded state of frame assembly 22, the majority of flexible portion 45 (e.g., more than 60 percent and/or less than 90 percent) is disposed further radially outward than span d16 of flanges 54.

For some applications, two or more of arms 46 are connected by a connector (not shown), reducing the flexibility, and/or the independence of movement of the connected arms relative to each other. For some applications, arms 46 are connected in particular sectors of upstream support portion 40, thereby making these sectors more rigid than sectors in which the arms are not connected. For example, a relatively rigid sector may be provided to be placed against the posterior portion of the mitral annulus, and a relatively flexible sector may be provided to be placed against the anterior side of the mitral annulus, so as to reduce forces applied by upstream support portion 40 on the aortic sinus.

For some applications, and as shown, coupling points 52 are disposed closer to downstream end 26 of frame assembly 22 than are flanges 54, or is upstream support portion 40.

As described in more detail with respect to FIGS. 4A-F, the movement of flange 54 away from coupling point 52 (and the typical movement of upstream support portion 40 toward the coupling point) facilitates the sandwiching of tissue of the native valve (e.g., leaflet and/or annulus tissue) between the flange and the upstream support portion, thereby securing implant 20 at the native valve.

Typically, in the compressed state of tubular portion 32, a downstream end of each leg 50 is longitudinally closer than valve-frame coupling elements 31 to downstream end 36, and flange 54 of each leg is disposed longitudinally closer than the valve-frame coupling elements to upstream end 34. Typically, this is also the case in the expanded state of tubular portion 32.

FIGS. 3A-C show structural changes in frame assembly 22 during transitioning of the assembly between its compressed and expanded states, in accordance with some applications of the invention. FIGS. 3A-C each show a portion of the frame assembly, the structural changes thereof being representative of the structural changes that occur in other portions of the frame assembly. FIG. 3A shows a leg 50 and struts 70 (e.g., a portion of outer frame 60), and illustrates the structural changes that occur around outer frame 60. FIG. 3B shows a portion of valve frame 30, and illustrates the structural changes that occur around the valve frame. FIG. 3C shows valve frame 30 as a whole. In each of FIGS. 3A-C, state (A) illustrates the structure while frame assembly 22 (and in particular tubular portion 32) is in its compressed state, and state (B) illustrates the structure while the frame assembly (and in particular tubular portion 32) is in its expanded state.

FIG. 3A shows structural changes in the coupling of legs 50 to coupling point 52 (e.g., structural changes of outer frame 60) during the transitioning of frame assembly 22 (and in particular tubular portion 32) between its compressed and expanded states. Each leg 50 is coupled to valve frame 30 via at least one strut 70, which connects the leg to coupling point 52. Typically, each leg 50 is coupled to valve frame 30 via a plurality of struts 70. A first end 72 of each strut 70 is coupled to leg 50, and a second end 74 of each strut is coupled to a coupling point 52. As described hereinabove, for applications in which frame 60 comprises ring 66, each leg 50 is coupled to the ring at a respective trough 62. Ring 66 may comprise struts 70, extending between the peaks and troughs, with each first end 72 at (or close to) a trough 62, and each second end 74 at (or close to) a peak 64.

In the compressed state of frame assembly 22 (and in particular of tubular portion 32), each strut 70 is disposed at a first angle in which first end 72 is disposed closer than second end 74 to the downstream end of the frame assembly. Expansion of frame assembly 22 (and in particular of tubular portion 32) toward its expanded state causes strut 70 to deflect to a second angle. This deflection moves first end 72 away from the downstream end of frame assembly 22. That is, in the expanded state of frame assembly 22, first end 72 is further from the downstream end of the frame assembly than it is when the frame assembly is in its compressed state. This movement is shown as a distance d5 between the position of end 72 in state (A) and its position in state (B). This movement causes the above-described movement of flanges 54 away from coupling points 52. As shown, flanges 54 typically move the same distance d5 in response to expansion of frame assembly 22.

For applications in which outer frame 60 comprises ring 66, the pattern of alternating peaks and troughs may be described as having an amplitude longitudinally between the peaks and troughs, i.e., measured parallel with central longitudinal axis ax1 of frame assembly 22, and the transition between the compressed and expanded states may be described as follows: In the compressed state of frame assembly 22 (and in particular of tubular portion 32), the pattern of ring 66 has an amplitude d20. In the expanded state frame assembly 22 (and in particular of tubular portion 32), the pattern of ring 66 has an amplitude d21 that is lower than amplitude d20. Because (i) it is at peaks 64 that ring 66 is coupled to valve frame 30 at coupling points 52, and (ii) it is at troughs 62 that ring 66 is coupled to legs 50, this reduction in the amplitude of the pattern of ring 66 moves legs 50 (e.g., flanges 54 thereof) longitudinally further from the downstream end of the frame assembly. The magnitude of this longitudinal movement (e.g., the difference between magnitudes d20 and d21) is equal to d5.

Typically, distance d5 is the same distance as the distance that flange 54 moves away from coupling point 52 during expansion of the frame assembly. That is, a distance between flange 54 and the portion of leg 50 that is coupled to strut 70, typically remains constant during expansion of the frame assembly. For some applications, the longitudinal movement of flange 54 away from coupling point 52 is a translational movement (e.g., a movement that does not include rotation or deflection of the flange).

For some applications, a distance d6, measured parallel to axis ax1 of frame assembly 22, between coupling point 52 and first end 72 of strut 70 while assembly 22 is in its compressed state, is 3-15 mm. For some applications, a distance d7, measured parallel to axis ax1, between coupling point 52 and first end 72 of strut 70 while assembly 22 is in its expanded state, is 1-5 mm (e.g., 1-4 mm).

For some applications, amplitude d20 is 2-10 mm (e.g., 4-7 mm). For some applications, amplitude d21 is 4-9 mm (e.g., 5-7 mm).

For some applications, and as shown, in the expanded state, first end 72 of strut 70 is disposed closer to the downstream end of frame assembly 22 than is coupling point 52. For some applications, in the expanded state, first end 72 of strut 70 is disposed further from the downstream end of frame assembly 22 than is coupling point 52.

For applications in which frame assembly 22 comprises a plurality of legs 50 and a plurality of coupling points 52 (e.g., for applications in which the frame assembly comprises outer frame 60) expansion of the frame assembly increases a circumferential distance between adjacent coupling points 52, and an increase in a circumferential distance between adjacent legs 50. FIG. 3A shows such an increase in the circumferential distance between adjacent coupling points 52, from a circumferential distance d8 in the compressed state to a circumferential distance d9 in the expanded state. For some applications, distance d8 is 1-6 mm. For some applications, distance d9 is 3-15 mm.

For some applications, in addition to being coupled via ring 66 (e.g., struts 70 thereof) legs 50 are also connected to each other via connectors 78. Connectors 78 allow the described movement of legs 50 during expansion of frame assembly 22, but typically stabilize legs 50 relative to each other while the frame assembly is in its expanded state. For example, connectors 78 may bend and/or deflect during expansion of the frame assembly.

FIGS. 3B-C show structural changes in valve frame 30 during the transitioning of frame assembly 22 between its compressed and expanded states. Tubular portion 32 of valve frame 30 is defined by a plurality of cells 80, which are defined by the repeating pattern of the valve frame. When frame assembly 22 is expanded from its compressed state toward its expanded state, cells 80 (i) widen from a width d10 to a width d11 (measured orthogonal to axis ax1 of the frame assembly), and (ii) shorten from a height d12 to a height d13 (measured parallel to axis ax1 of the frame assembly). This shortening reduces the overall height (i.e., a longitudinal length between upstream end 34 and downstream end 36) of tubular portion 32 from a height d22 to a height d23, and thereby causes the above-described longitudinal movement of upstream support portion 40 toward coupling points 52 by a distance d14 (shown in FIG. 3C). For some applications, and as shown, coupling points 52 are disposed at the widest part of each cell.

Due to the configurations described herein, the distance by which flanges 54 move with respect to (e.g., toward, or toward-and-beyond) upstream support portion 40 (e.g., arms 46 thereof), is typically greater than the reduction in the overall height of tubular portion 32 (e.g., more than 20 percent greater, such as more than 30 percent greater, such as more than 40 percent greater). That is, implant 20 comprises:
- a valve frame (30) that comprises a tubular portion (32) that circumscribes a longitudinal axis (ax1) of the valve frame so as to define a lumen (38) along the axis, the tubular portion having an upstream end (34), a downstream end (36), a longitudinal length therebetween, and a diameter (e.g., d1 or d2) transverse to the longitudinal axis;
- a valve member (58), coupled to the tubular portion, disposed within the lumen, and arranged to provide unidirectional upstream-to-downstream flow of blood through the lumen;
- an upstream support portion (40), coupled to the tubular portion; and
- an outer frame (60), coupled to the tubular portion, and comprising a tissue-engaging flange (54), wherein:
the implant has a first state (e.g., as shown in FIG. 2D and FIG. 4D) and a second state (e.g., as shown in FIG. 2E and FIG. 4E),
in both the first state and the second state, (i) the upstream support portion extends radially outward from the tubular portion, and (ii) the tissue-engaging flange extends radially outward from the tubular portion, and
the tubular portion, the upstream support portion, and the outer frame are arranged such that transitioning of the implant from the first state toward the second state:
increases the diameter of the tubular portion by a diameter-increase amount (e.g., the difference between d1 and d2),
decreases the length of the tubular portion by a length-decrease amount (e.g., the difference between d22 and d23), and
moves the flange a longitudinal distance with respect to (e.g., toward or toward-and-beyond) the upstream support portion (e.g., the difference between d3 and d4), this distance being greater than the length-decrease amount.

As shown in the figures, valve frame 30 is typically coupled to outer frame 60 by coupling between (i) a valve-frame coupling element 31 defined by valve frame 30, and (ii) an outer-frame coupling element 61 defined by outer frame 60 (e.g., an outer-frame coupling element is coupled to end 74 of each strut). Typically, elements 31 and 61 are fixed with respect to each other. Each coupling point 52 is thereby typically defined as the point at which a valve-frame coupling element and a corresponding outer-frame coupling element 61 are coupled (e.g., are fixed with respect to each other). For some applications, and as shown, elements 31 and 61 are eyelets configured to be coupled together by a connector, such as a pin or suture. Alternatively or additionally, elements 31 and 61 are soldered or welded together. For example, elements 31 and 61 may be coupled together by a pin that passes through the eyelets, and is welded in place.

Typically, and as shown, valve-frame coupling elements 31 are defined by tubular portion 32, and are disposed circumferentially around central longitudinal axis ax1. Outer-frame coupling elements 61 are coupled to ring 66 (or defined by frame 60, such as by ring 66) at respective peaks 64.

As shown (e.g., in FIGS. 2A-E), valve frame 30 (e.g., tubular portion 32 thereof) and outer frame 60 (e.g., ring 66 thereof) are arranged in a close-fitting coaxial arrangement, in both the expanded and compressed states of frame assembly 22. Ignoring spaces due to the cellular structure of the frames, a radial gap d19 between valve frame 30 (e.g., tubular portion 32 thereof) and outer frame 60 (e.g., ring 66 thereof) is typically less than 2 mm (e.g., less than 1 mm), in both the compressed and expanded states, and during the transition therebetween. This is facilitated by the coupling between frames 30 and 60, and the behavior, described hereinabove, of frame 60 in response to changes in the diameter of tubular portion 32 (e.g., rather than solely due to delivery techniques and/or tools). For some applications, more than 50 percent (e.g., more than 60 percent) of ring 66 is disposed within 2 mm of tubular portion 32 in both the compressed and expanded states, and during the transition therebetween. For some applications, more than 50 percent (e.g., more than 60 percent) of outer frame 60, except for flanges 54, is disposed within 2 mm of tubular portion 32 in both the compressed and expanded states, and during the transition therebetween.

The structural changes to frame assembly 22 (e.g., to outer frame 60 thereof) are described hereinabove as they occur during (e.g., as a result of) expansion of the frame assembly (in particular tubular portion 32 thereof). This is the natural way to describe these changes because, as described hereinbelow with respect to FIGS. 4A-6, assembly 22 is in its compressed state during percutaneous delivery to the implant site, and is subsequently expanded. However, the nature of implant 20 may be further understood by describing structural changes that occur during compression of the frame assembly (e.g., a transition from the expanded state in FIG. 2E to the intermediate state in FIG. 2D), in particular tubular portion 32 thereof (including if tubular portion 32 were compressed by application of compressive force to the tubular portion, and not to frame 60 except via the tubular portion pulling frame 60 radially inward). Such descriptions may also be relevant because implant 20 is typically compressed (i.e., "crimped") soon before its percutaneous delivery, and therefore these changes may occur while implant 20 is in the care of the operating physician.

For some applications, the fixation of peaks 64 to respective sites of tubular portion 32 is such that compression of the tubular portion from its expanded state toward its compressed state such that the respective sites of the tubular portion pull the peaks radially inward via radially-inward tension on coupling points 52: (i) reduces a circumferential distance between each of the coupling points and its adjacent coupling points (e.g., from d9 to d8), and (ii) increases the amplitude of the pattern of ring 66 (e.g., from d21 to d20).

For some applications, the fixation of outer-frame coupling elements 61 to valve-frame coupling elements 31 is such that compression of tubular portion 32 from its expanded state toward its compressed state such that the valve-frame coupling elements pull the outer-frame coupling elements radially inward: (i) reduces a circumferential distance between each of the outer-frame coupling elements and its adjacent outer-frame coupling elements (e.g., from d9 to d8), and (ii) increases the amplitude of the pattern of ring 66 (e.g., from d21 to d20).

For some applications, the fixation of peaks 64 to the respective sites of tubular portion 32 is such that compression of the tubular portion from its expanded state toward its compressed state (i) pulls the peaks radially inward via radially-inward pulling of the respective sites of the tubular portion on the peaks, (ii) reduces a circumferential distance between each of coupling points 52 and its adjacent coupling points (e.g., from d9 to d8), and (iii) increases the amplitude of the pattern of ring 66 (e.g., from d21 to d20), without increasing radial gap d19 between valve frame 30 (e.g., tubular portion 32 thereof) and the ring by more than 1.5 mm.

For some applications, the fixation of outer-frame coupling elements 61 with respect to valve-frame coupling elements 31 is such that compression of tubular portion 32 from its expanded state toward its compressed state (i) pulls outer-frame coupling elements 61 radially inward via radially-inward pulling of valve-frame coupling elements 31 on outer-frame coupling elements 61, (ii) reduces a circumferential distance between each of the outer-frame coupling elements and its adjacent outer-frame coupling elements (e.g., from d9 to d8), and (iii) increases the amplitude of the pattern of ring 66 (e.g., from d21 to d20), without increasing radial gap d19 between valve frame 30 (e.g., tubular portion 32 thereof) and the ring by more than 1.5 mm.

Reference is made to FIGS. 4A-F, which are schematic illustrations of implantation of implant 20 at a native valve 10 of a heart 4 of a subject, in accordance with some applications of the invention. Valve 10 is shown as a mitral valve of the subject, disposed between a left atrium 6 and a left ventricle 8 of the subject. However, implant 20 may be implanted at another heart valve of the subject, mutatis mutandis. Similarly, although FIGS. 4A-F show implant 20 being delivered transseptally via a sheath 88, the implant may alternatively be delivered by any other suitable route, such as transatrially, or transapically.

Implant 20 is delivered, in its compressed state, to native valve 10 using a delivery tool 89 that is operable from outside the subject (FIG. 4A). Typically, implant 20 is delivered within a delivery capsule 90 of tool 89, which retains the implant in its compressed state. Delivery capsule 90 is disposed at a distal end of tool 89. A transseptal approach, such as a transfemoral approach, is shown. Typically, implant 20 is positioned such that at least flanges 54 are disposed downstream of the native valve (i.e., within ventricle 8). At this stage, frame assembly 22 of implant 20 is as shown in FIG. 2A.

Subsequently, flanges 54 are allowed to protrude radially outward, as described hereinabove, e.g., by releasing them from capsule 90 (FIG. 4B). For example, and as shown, capsule 90 may comprise a distal capsule-portion 92 and a proximal capsule-portion 94, and the distal capsule-portion may be moved distally with respect to implant 20, so as to expose flanges 54. At this stage, frame assembly 22 of implant 20 is as shown in FIG. 2B.

Subsequently, implant 20 is moved upstream, such that upstream support portion 40, in its compressed state, is disposed upstream of leaflets 12 (i.e., within atrium 6). For some applications, the upstream movement of implant 20 causes flanges 54 to engage leaflets 12. However, because of the relatively large distance d3 provided by implant 20 (described hereinabove), for some applications it is not necessary to move the implant so far upstream that flanges 54 tightly engage leaflets 12 and/or pull the leaflets upstream of the valve annulus. Upstream support portion 40 is then allowed to expand such that it protrudes radially outward, as described hereinabove, e.g., by releasing it from capsule 90 (FIG. 4D). For example, and as shown, proximal capsule-portion 94 may be moved proximally with respect to implant 20, so as to expose upstream support portion 40. At this stage, frame assembly 22 of implant 20 is as shown in FIG. 2D, in which: (i) distance d3 exists between upstream support portion 40 and flanges 54, (ii) the flanges have span d15, (iii) the upstream support portion has span d17, and (iv) tubular portion 32 has diameter d1.

Typically, expansion of frame assembly 22 is inhibited by distal capsule-portion 92, e.g., by inhibiting expansion of tubular portion 32. For example, a downstream region 33 of frame assembly 22, downstream of flanges 54, may remain compressed within distal capsule-portion 92. Alternatively or additionally, the expansion may be inhibited by another portion of delivery tool 89 (e.g., a portion of the delivery tool that is disposed within lumen 38).

Subsequently, implant 20 is allowed to expand toward its expanded state, such that tubular portion 32 widens to diameter d2, and the distance between upstream support portion 40 and flanges 54 reduces to distance d4 (FIG. 4E). This is typically achieved by deploying downstream region 33 from capsule-portion 92. This expansion sandwiches tissue of valve 10 (typically including annular tissue and/or leaflets 12) between upstream support portion 40 and flanges 54, thereby securing implant 20 at the valve. FIG. 4F shows delivery capsule 90 having been removed from the body of the subject, leaving implant 20 in place at valve 10.

As described hereinabove, implant 20 is configured such that when tubular portion 32 is expanded, flanges 54 and upstream support portion 40 move a relatively large distance toward each other. This enables distance d3 to be relatively large, while distance d4 is sufficiently small to provide effective anchoring. As also described hereinabove, implant 20 is configured such that flanges 54 and upstream support portion 40 can extend radially outward a relatively large distance while tubular portion 32 remains compressed. It is hypothesized that for some applications, these configurations (independently and/or together) facilitate effective anchoring of implant 20, by facilitating placement of a relatively large proportion of valve tissue (e.g., leaflets 12) between the flanges and the upstream support portion prior to expanding tubular portion 32 and sandwiching the valve tissue.

It is further hypothesized that the relatively great radially-outward extension of flanges 54 and upstream support portion 40 prior to expansion of tubular portion 32, further facilitates the anchoring/sandwiching step by reducing radially-outward pushing of the valve tissue (e.g., leaflets 12) during the expansion of the tubular portion, and thereby increasing the amount of valve tissue that is sandwiched.

It is yet further hypothesized that this configuration of implant 20 facilitates identifying correct positioning of the implant (i.e., with upstream support portion 40 upstream of leaflets 12 and flanges 54 downstream of the leaflets) prior to expanding tubular portion 32 and sandwiching the valve tissue.

It is to be noted that the deployment of implant 20 is therefore achieved by:
  unhousing a longitudinally-intermediate portion of the implant (to allow flanges 54 to expand), the longitudinally-intermediate portion being longitudinally between a longitudinally-proximal portion of the implant and a longitudinally distal portion of the implant;
  subsequently, unhousing the longitudinally-proximal portion of the implant (to allow upstream support portion 40 to expand); and
  subsequently, unhousing the longitudinally-distal portion of the implant (to allow the longitudinally-distal portion of the implant, typically including the tubular portion within which valve member 58 is disposed, to expand).

It is to be further noted that the deployment of implant 20 may be described with respect to delivery tool 89. For example:
  distal capsule-portion 92 is moved distally with respect to the implant (to allow flanges 54 to expand);
  subsequently, proximal capsule-portion 94 is moved proximally with respect to the implant (to allow upstream support portion 40 to expand); and
  subsequently, distal capsule-portion 92 is again moved distally with respect to the implant (to allow the longitudinally distal portion of the implant, typically including the tubular portion within which valve member 58 is disposed, to expand).

For some applications, delivery tool 89 (e.g., an extracorporeal control portion 110 thereof, disposed at a proximal portion of the delivery tool) is configured to ensure that the operator follows the particular sequence of movement of capsule-portions 92 and 94 described. For example, control portion 110 may comprise a series of locks 114, each lock becoming unlockable only after the previous step in the sequence has been completed, the unlocking of the lock allowing the subsequent step in the sequence to be performed. For some such applications, control portion 110 may further comprise a series of controllers 112, via which the operator causes the movement of a respective capsule-portion for each respective step. An example of how control portion 110 may be used, in accordance with some applications of the invention, is as follows:
  (1) Operator moves distal capsule-portion 92 distally with respect to implant 20 by actuating a first controller 112a. Once capsule-portion 92 has been moved a given distance, a first lock 114a automatically becomes unlockable (and typically capsule-portion 92 is prevented from moving further than the given distance).
  (2) Operator unlocks lock 114a, and then moves proximal capsule-portion 94 proximally with respect to implant 20 by actuating a second controller 112b. Once capsule-portion 94 has been moved a given distance, a second lock 114b automatically becomes unlockable.
  (3) Operator unlocks lock 114b, and then moves distal capsule-portion 92 further distally with respect to implant 20 by again actuating first controller 112a. Alternatively, control portion 110 may comprise a third controller (not shown) for this second movement of distal capsule-portion 92.

It is to be noted that throughout this patent application (including in the specification and in the claims) the term "unlockable" means able to be unlocked (rather than meaning not lockable).

Therefore, apparatus is provided, in accordance with some applications of the invention, the apparatus comprising an implant (e.g., implant 20) and a delivery tool (e.g., tool 89), the tool comprising:
  (1) a delivery capsule, disposed at a distal portion of the tool, the delivery capsule comprising a proximal capsule-portion 94 dimensioned to house a first part of the implant, and a distal capsule-portion 92 dimensioned to house a second part of the implant; and
  (2) an extracorporeal control portion 110, disposed at a proximal portion of the tool, the control portion comprising one or more controllers 112 and one or more locks 114, the controllers being operatively coupled to the proximal and distal capsule-portions such that the proximal and distal capsule-portions are movable with respect to the housed implant via actuation of the controllers,
wherein the controllers and the locks are mechanically cooperative such that:
  in a first state of the tool:
    a first distal movement of the distal capsule-portion up to a first distance distally with respect to the implant is facilitated,
    a second distal movement of the distal capsule-portion further distally with respect to the implant is inhibited,
    a proximal movement of the proximal capsule-portion proximally with respect to the implant is inhibited, and
    responsively to movement of the distal capsule-portion distally, the tool automatically unlocks a second state of the tool;
  in the second state of the tool:
    the proximal movement of the proximal capsule-portion is facilitated,
    the second distal movement of the distal capsule-portion remains inhibited, and
    responsively to movement of the proximal capsule-portion proximally, the tool automatically unlocks a third state of the tool; and
  in the third state of the tool:
    the second distal movement of the distal capsule-portion is facilitated.

For some applications, rather than having three states, tool 89 has two states. For clarity, these will be referred to as state A and state B. However, state A may be similar to the second state described hereinabove, mutatis mutandis. (State A may alternatively be called a primary state, and state B may alternatively be called a secondary state.) For applications in which tool 89 has two states, the tool typically has only one lock 114, the unlocking of which transitions the tool from state A to state B.

In state, A, it is possible to move distal capsule-portion 92 up to the first distance distally with respect to implant 20 (e.g., by actuating controller 112*a*), and to move proximal capsule-portion 94 proximally with respect to the implant (e.g., by actuating controller 112*b*), but it is not possible to move the distal capsule-portion further distally, which would deploy downstream region 33. Typically, in state A, it is also possible to return proximal capsule-portion 94 distally and distal capsule-portion 92 proximally. In state B, it is possible to move distal capsule-portion 92 further distally, thereby deploying downstream region 33. For some applications, lock 114 is not unlockable until distal capsule-portion 92 has been moved the first distance distally, and/or until proximal capsule-portion 94 has been moved proximally.

Therefore, apparatus is provided, in accordance with some applications of the invention, the apparatus comprising an implant and a delivery tool, the tool comprising:
- a delivery capsule, disposed at a distal portion of the tool, the delivery capsule comprising a proximal capsule-portion dimensioned to house a first part of the implant, and a distal capsule-portion dimensioned to house a second part of the implant; and
- an extracorporeal control portion, disposed at a proximal portion of the tool, the control portion comprising one or more controllers and one or more locks, the controllers being operatively coupled to the proximal and distal capsule-portions such that the proximal and distal capsule-portions are movable with respect to the implant via actuation of the controllers, wherein the controllers and the locks are mechanically cooperative such that:
- in a state A of the tool: (i) a first distal movement of the distal capsule-portion up to a first distance distally with respect to the implant is facilitated, (ii) a second distal movement of the distal capsule-portion further distally with respect to the implant is inhibited, and (iii) a proximal movement of the proximal capsule-portion proximally with respect to the implant is facilitated; and
- in a state B of the tool, the second distal movement of the distal capsule-portion is facilitated.

As shown in FIG. 1A, for some applications, in the expanded state of frame assembly 22, implant 20 defines a toroidal space 49 between flanges 54 and upstream support portion 40 (e.g., a space that is wider than distance d4). For example, space 49 may have a generally triangular cross-section. It is hypothesized that for some such applications, in addition to sandwiching tissue of the native valve between upstream support portion 40 and flanges 54 (e.g., the tips of the flanges), space 49 advantageously promotes tissue growth therewithin (e.g., between leaflet tissue and covering 23), which over time further secures implant 20 within the native valve.

Reference is now made to FIG. 5, which is a schematic illustration of a step in the implantation of implant 20, in accordance with some applications of the invention. Whereas FIGS. 4A-F show an implantation technique in which flanges 54 are expanded prior to upstream support portion 40, for some applications the upstream support portion is expanded prior to the flanges. FIG. 5 shows a step in such an application.

Reference is again made to FIGS. 2A-5. As noted hereinabove, implant 20 may be implanted by causing flanges 54 to radially protrude before causing upstream support portion 40 to radially protrude, or may be implanted by causing the upstream support portion to protrude before causing the flanges to protrude. For some applications, implant 20 is thereby configured to be deliverable in a downstream direction (e.g., transseptally, as shown, or transapically) or in an upstream direction (e.g., transapically or via the aortic valve). Thus, for some applications, an operating physician may decide which delivery route is preferable for a given application (e.g., for a given subject, and/or based on available equipment and/or expertise), and implant 20 is responsively prepared for the chosen delivery route (e.g., by loading the implant into an appropriate delivery tool).

It is to be noted that for some applications, downstream delivery of implant 20 may be performed by expanding flanges 54 first (e.g., as shown in FIGS. 4A-F) or by expanding upstream support portion 40 first (e.g., as shown in FIG. 5). Similarly, for some applications upstream delivery of implant 20 may be performed by upstream support portion 40 first, or by expanding flanges 54 first.

Figure 6:
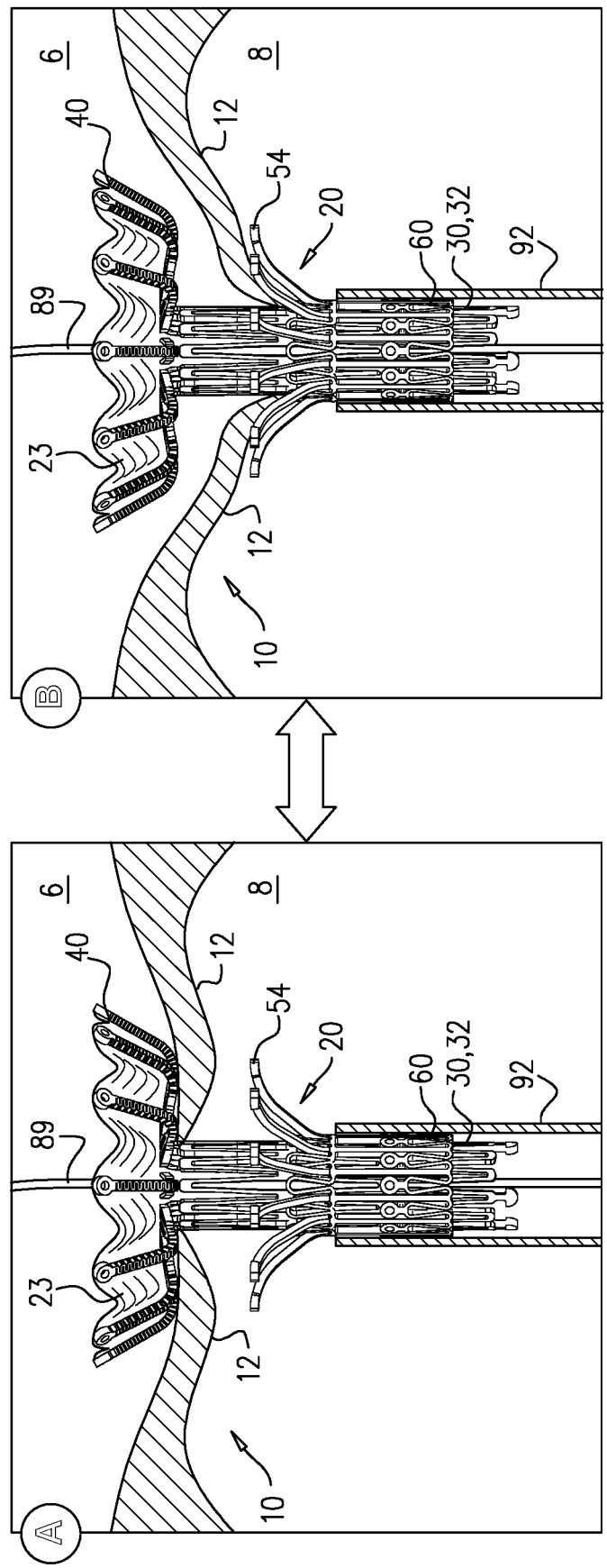
FIG. 6 is a schematic illustration of the implant, in accordance with some applications of the invention.

Reference is now made to FIG. 6, which is a schematic illustration of implant 20, in the state and position shown in FIG. 4D, in accordance with some applications of the invention. For some applications, while implant 20 is in the state and position shown in FIG. 4D, leaflets 12 of valve 10 are able to move, at least in part in response to beating of the heart. Frame (A) shows leaflets 12 during ventricular systole, and frame (B) shows the leaflets during ventricular diastole. For some such applications, blood is thereby able to flow from atrium 6 to ventricle 8, between leaflets 12 and implant 20. It is hypothesized that this advantageously facilitates a more relaxed implantation procedure, e.g., facilitating retaining of implant 20 in this state and position for a duration of greater than 8 minutes. During this time, imaging techniques may be used to verify the position of implant 20, and/or positioning of leaflets 12 between upstream support portion 40 and flanges 54.

Reference is made to FIGS. 7A-B and 8A-B, which are schematic illustrations of frame assemblies 122 and 222 of respective implants, in accordance with some applications of the invention. Except where noted otherwise, frame assemblies 122 and 222 are typically identical to frame assembly 22, mutatis mutandis. Elements of frame assemblies 122 and 222 share the name of corresponding elements of frame assembly 22. Additionally, except where noted otherwise, the implants to which frame assemblies 122 and 222 belong are similar to implant 20, mutatis mutandis.

Frame assembly 122 comprises (i) a valve frame 130 that comprises a tubular portion 132 and an upstream support portion 140 that typically comprises a plurality of arms 146, and (ii) an outer frame (e.g., a leg frame) 160 that circumscribes the valve frame, and comprises a plurality of legs 150 that each comprise a tissue-engaging flange 154. Typically, outer frame 160 comprises a ring 166 to which legs 150 are coupled. Ring 166 is defined by a pattern of alternating peaks and troughs, the peaks being fixed to frame 130 at respective coupling points 152, e.g., as described hereinabove for frame assembly 22, mutatis mutandis.

Frame assembly 222 comprises (i) a valve frame 230 that comprises a tubular portion 232 and an upstream support portion 240 that typically comprises a plurality of arms 246, and (ii) an outer frame (e.g., a leg frame) 260 that circumscribes the valve frame, and comprises a plurality of legs 250 that each comprise a tissue-engaging flange 254. Typically, outer frame 260 comprises a ring 266 to which legs 250 are coupled. Ring 266 is defined by a pattern of alternating peaks and troughs, the peaks being fixed to frame 230 at respective coupling points 252, e.g., as described hereinabove for frame assembly 22, mutatis mutandis.

Whereas arms 46 of frame assembly 22 are shown as extending from upstream end 34 of tubular portion 32, arms 146 and 246 of frame assemblies 122 and 222, respectively, extend from sites further downstream. (This difference may also be made to frame assembly 22, mutatis mutandis.) Tubular portions 32, 132 and 232 are each defined by a repeating pattern of cells that extends around the central longitudinal axis. Typically, and as shown, tubular portions 32, 132 and 232 are each defined by two stacked, tessellating rows of cells. In the expanded state of each tubular portion, these cells are typically narrower at their upstream and downstream extremities than midway between these extremities. For example, and as shown, the cells may be roughly diamond or astroid in shape. In frame assembly 22, each arm 46 is attached to and extends from a site 35 that is at the upstream extremity of cells of the upstream row. In contrast, in frame assemblies 122 and 222, each arm 146 or 246 is attached to and extends from a site 135 (assembly 122) or 235 (assembly 222) that is at the connection between two adjacent cells of the upstream row (alternatively described as being at the upstream extremity of cells of the downstream row).

It is hypothesized by the inventors that this lower position of the arms, while maintaining the length of the lumen of the tubular portion, advantageously reduces the distance that the tubular portion (i.e., the downstream end thereof) extends into the ventricle of the subject, and thereby reduces a likelihood of inhibiting blood flow out of the ventricle through the left ventricular outflow tract. It is further hypothesized that this position of the arms reduces radial compression of the tubular portion by movement of the heart, due to greater rigidity of the tubular portion at sites 135 and 235 (which is supported by two adjacent cells) than at site 35 (which is supported by only one cell).

As shown, in the expanded state of frame assemblies 22, 122 and 222, the legs (50, 150 and 250, respectively) are circumferentially staggered with the arms of the upstream support portion (46, 146 and 246, respectively). This allows the legs to move in an upstream direction between the arms during expansion of the tubular portion (32, 132 and 232, respectively), facilitating application of greater sandwiching force on tissue of the native valve. The lower position of the arms of assemblies 122 and 222 includes circumferentially shifting the position of the arms by the width of half a cell. In order to maintain the circumferential staggering of the arms and legs, rings 166 and 266 (and thereby legs 150 and 250) are circumferentially shifted correspondingly. As a result, whereas the peaks of ring 66 generally align with connections between adjacent cells of the downstream row of cells of tubular portion 32 (and are fixed to these sites), the peaks of rings 166 and 266 are generally aligned midway between these sites (i.e., at spaces of the cellular structure of the tubular portion). Appendages 168 (for assembly 122) or 268 (for assembly 222) facilitate fixing of the peak with respect to the tubular structure.

For assembly 122, appendages 168 are defined by valve frame 130 (e.g., by tubular portion 132 thereof) and extend (in a downstream direction) to the peaks of ring 166, to which they are fixed. For example, each appendage 168 may define a valve-frame coupling element 131 that is fixed to a respective outer-frame coupling element 161 defined by outer frame 260. Typically, appendages 168 extend from sites 135. Typically, appendages 168 are integral with tubular portion 132 and/or in-plane with the tubular portion (e.g., are part of its tubular shape).

For assembly 222, appendages 268 are defined by outer frame 260, and extend (e.g., in an upstream direction) from the peaks of ring 266. Typically, appendages 268 extend to sites 235, to which they are fixed. For example, each appendage 268 may define an outer-frame coupling element 261 that is fixed to a respective valve-frame coupling element 231 defined by valve frame 230 (e.g., by tubular portion 232 thereof). Typically, appendages 268 are integral with outer frame 260 and/or in-plane with adjacent portions of outer frame 260, such as ring 266.

Therefore, frame assembly 122 defines a hub at site 135, and frame assembly 222 defines a hub at site 235. For some applications, apparatus therefore comprises:
  a plurality of prosthetic valve leaflets; and
  a frame assembly, comprising:
    a tubular portion (132 or 232) defined by a repeating pattern of cells, the tubular portion extending circumferentially around longitudinal axis ax1 so as to define a longitudinal lumen, the prosthetic valve leaflets coupled to the inner frame and disposed within the lumen;
    an outer frame (160 or 260), comprising a plurality of legs (150 or 250), distributed circumferentially around the tubular portion, each leg having a tissue-engaging flange (154 or 254);
    an upstream support portion (140 or 240) that comprises a plurality of arms (146 or 246) that extend radially outward from the tubular portion; and
    a plurality of appendages (168 or 268), each having a first end that defines a coupling element (161 or 261) via which the tubular portion is coupled to the outer frame, and a second end;
  wherein the frame assembly defines a plurality of hubs (135 or 235), distributed circumferentially around the longitudinal axis on a plane that is transverse to longitudinal axis ax1, each hub defined by convergence and connection of, (i) two adjacent cells of the tubular portion, (ii) an arm of the plurality of arms, and (iii) an appendage of the plurality of appendages.

Figure 9C:
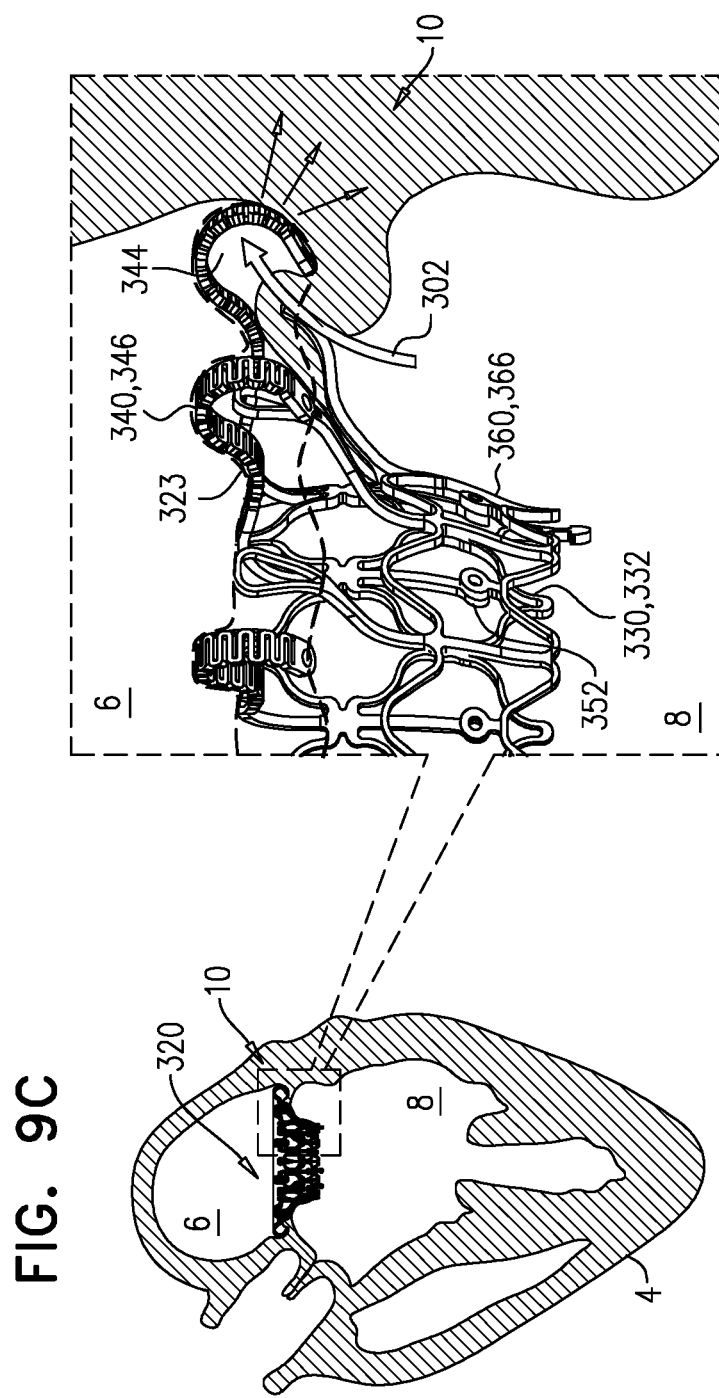

Reference is made to FIGS. 9A-C, which are schematic illustrations of an implant 320 comprising a frame assembly 322, in accordance with some applications of the invention. Except where noted otherwise, frame assembly 322 is identical to frame assembly 122, and implant 300 is identical to the implant to which frame assembly 122 belongs, mutatis mutandis. FIG. 9A is a side-view of implant 320, and FIG. 9B is an isometric bottom-view of the implant.

Frame assembly 122 comprises (i) a valve frame 330 that comprises a tubular portion 332 and an upstream support portion 340 that typically comprises a plurality of arms 346, and (ii) an outer frame (e.g., a leg frame) 360 that circumscribes the valve frame, and comprises a plurality of legs 350 that each comprise a tissue-engaging flange 354. Typically, outer frame 360 comprises a ring 366 to which legs 350 are coupled. Ring 366 is defined by a pattern of alternating peaks and troughs, the peaks being fixed to frame 330 at respective coupling points 352, e.g., as described hereinabove for frame assembly 22 and/or frame assembly 122, mutatis mutandis.

Frame assembly 322 comprises an annular upstream support portion 340 that has an inner portion 342 that extends radially outward from the upstream portion (e.g., the upstream end) of tubular portion 332. Upstream support portion 340 further comprises one or more fabric pockets 344 disposed circumferentially around inner portion 342, each pocket of the one or more pockets having an opening that faces a downstream direction (i.e., generally toward the downstream end of implant 320). In the figures, upstream support portion 340 has a single toroidal pocket 344 that extends circumferentially around inner portion 342.

Typically, a covering 323 (e.g., similar to covering 23, described hereinabove, mutatis mutandis) is disposed over arms 346, thereby forming pocket 344. Further typically, arms 346 are shaped to form pocket 344 from covering 323. For example, and as shown, arms 346 may curve to form a hook-shape.

For some applications, portion 340 has a plurality of separate pockets 344, e.g., separated at arms 346. For some such applications, covering 323 is loosely-fitted (e.g., baggy) between radially-outward parts of arms 346, e.g., compared to inner portion 342, in which the covering is more closely-fitted between radially-inward parts of the arms.

FIG. 9C shows implant 320 implanted at native valve 10. Pocket 344 is typically shaped and arranged to billow in response to perivalvular flow 302 of blood in an upstream direction. If ventricular systole forces blood in ventricle 8 between implant 320 and native valve 10, that blood inflates pocket 344 and presses it (e.g., covering 323 and/or the radially-outward part of arm 346) against tissue of atrium 6 (e.g., against the atrial wall), thereby increasing sealing responsively. It is hypothesized by the inventors that the shape and orientation of pocket 344 (e.g., the hook-shape of arms 346) facilitates this pressing radially-outward in response to the pocket's receipt of upstream-flowing blood.

Pocket(s) 344 may be used in combination with any of the implants described herein, mutatis mutandis.

Reference is again made to FIGS. 1A-9C. It is to be noted that unless specifically stated otherwise, the term "radially outward" (e.g., used to describe upstream support portion 40 and flanges 54) means portions of the element are disposed progressively further outward from a central point (such as longitudinal axis ax1 or tubular portion 32), but does not necessarily mean disposed at 90 degrees with respect to longitudinal axis ax1. For example, flanges 54 may extend radially outward at 90 degrees with respect to longitudinal axis ax1, but may alternatively extend radially outward at a shallower angle with respect to the longitudinal axis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
    percutaneously advancing an implant to a native heart valve of a subject, the implant housed in a compressed state within a delivery tool;
    unhousing a longitudinally-intermediate portion of the implant, the longitudinally-intermediate portion being longitudinally between a longitudinally-proximal portion of the implant and a longitudinally distal portion of the implant;
    subsequently, unhousing the longitudinally-proximal portion of the implant; and
    subsequently, unhousing the longitudinally-distal portion of the implant,
wherein:
    unhousing the longitudinally-intermediate portion of the implant comprises unhousing flanges of the implant such that the flanges automatically expand, and such that upon the flanges expanding a proximal end of each flange extends radially outward from a central longitudinal axis of the implant and longitudinally in a proximal direction.

2. The method according to claim 1, wherein:
    unhousing the longitudinally-proximal portion of the implant comprises unhousing an upstream support portion of the implant such that the upstream support portion automatically expands; and
    unhousing the longitudinally-distal portion of the implant comprises unhousing the longitudinally-distal portion of the implant such that the longitudinally-distal portion of the implant automatically expands.

3. The method according to claim 2, wherein the longitudinally-distal portion includes a tubular portion within which a valve member is disposed, and wherein unhousing the longitudinally-distal portion of the implant comprises unhousing the longitudinally-distal portion of the implant such that the tubular portion expands to form a lumen and the valve member regulates one-way flow of blood through the lumen.

4. The method according to claim 3, wherein unhousing the longitudinally-distal portion of the implant comprises facilitating expansion of the implant such that the tubular portion expands and the flanges become longitudinally closer to the upstream support portion.

5. The method according to claim 4, wherein facilitating expansion of the implant comprises sandwiching leaflets of the native heart valve between the flanges and the upstream support portion.

6. The method according to claim 1, wherein:
    percutaneously advancing the implant to the native heart valve comprises advancing the implant housed within a capsule of the delivery tool, the capsule having a distal capsule-portion and a proximal capsule-portion,
    unhousing the longitudinally-intermediate portion of the implant comprises unhousing the longitudinally-intermediate portion from within the distal capsule-portion by moving the distal capsule-portion distally with respect to the implant,
    unhousing the longitudinally-proximal portion comprises unhousing the longitudinally-proximal portion from within the proximal capsule-portion by moving the proximal capsule-portion proximally with respect to the implant, and
    unhousing the longitudinally-distal portion of the implant comprises deploying the longitudinally-distal portion of the implant from the distal capsule-portion.

7. The method according to claim 6, wherein deploying the longitudinally-distal portion of the implant from the distal capsule-portion comprises additionally moving the distal capsule-portion distally with respect to the implant.

8. Apparatus, comprising:
    an implant for implantation at a native valve of a heart of a subject, the implant comprising a valve frame assembly comprising:
        a tubular portion having an upstream end and a downstream end that defines, in part, a longitudinally-distal portion of the implant;

an upstream support portion, extending from the upstream end of the tubular portion, the upstream portion defining a longitudinally-proximal portion of the implant; and a plurality of tissue-engaging flanges coupled to the tubular portion at respective coupling points, the plurality of flanges defining a longitudinally-intermediate portion of the implant; and a delivery tool:

comprising a delivery capsule dimensioned (i) to house and retain the implant in a compressed state of the implant in which (a) the tubular portion is in a constrained-tubular-portion state, (b) the upstream support portion is in a constrained-upstream-support-portion state, and (c) the plurality of flanges are in a constrained-flange state, and (ii) to be advanced percutaneously to the heart of the subject while the implant is housed and in the compressed state, and operable from outside the subject to:

transition the implant from the compressed state into an intermediate state of the implant by (1) unhousing the longitudinally-intermediate portion, while retaining the tubular portion in the constrained-tubular-portion state, and (2) subsequently, unhousing the longitudinally-proximal portion of the implant, while retaining at least the longitudinally-distal portion of the implant in a constrained state, and subsequently, unhouse the longitudinally-distal portion of the implant such that the implant assumes an expanded state, such that in the expanded state a proximal end of each flange extends radially outward from a central longitudinal axis of the implant and longitudinally in a proximal direction.

9. The apparatus according to claim 8, wherein:
the upstream support portion is configured such that, upon the implant entering the intermediate state, the upstream support portion is expanded into a released-upstream-support-portion state.

10. The apparatus according to claim 8, wherein the tubular portion is configured such that, upon the implant transitioning from the intermediate state to the expanded state, the tubular portion expands and thereby moves the plurality of flanges longitudinally closer to the upstream support portion.

11. The apparatus according to claim 8, wherein the tubular member comprises a valve member, and wherein, in the expanded state of the implant, the tubular portion defines a lumen therethrough, and the valve member is configured to regulate one-way flow of blood through the lumen.

12. The apparatus according to claim 8, wherein the capsule of the delivery tool comprises a distal capsule-portion and a proximal capsule-portion, and wherein the capsule is configured such that:

upon the implant entering the intermediate state, (i) the distal capsule-portion is moved distally with respect to the implant to unhouse the longitudinally-intermediate portion of the implant, while still surrounding the longitudinally-distal portion of the implant, and (ii) the proximal capsule-portion is moved proximally with respect to the implant to unhouse the longitudinally-proximal portion, and upon the implant entering the expanded state, the distal capsule-portion is moved further distally with respect to the implant to unhouse the longitudinally-distal portion of the implant.

13. A method, comprising:

percutaneously advancing an implant to a native heart valve of a subject, the implant housed in a compressed state within a delivery tool;

unhousing a longitudinally-intermediate portion of the implant, the longitudinally-intermediate portion being longitudinally between a longitudinally-proximal portion of the implant and a longitudinally distal portion of the implant;

subsequently, unhousing the longitudinally-proximal portion of the implant; and subsequently, unhousing the longitudinally-distal portion of the implant, wherein:

unhousing the longitudinally-intermediate portion of the implant comprises unhousing flanges of the implant such that the flanges automatically expand;

unhousing the longitudinally-proximal portion of the implant comprises unhousing an upstream support portion of the implant such that the upstream support portion automatically expands; and unhousing the longitudinally-distal portion of the implant comprises unhousing the longitudinally-distal portion of the implant such that the longitudinally-distal portion of the implant automatically expands, wherein the longitudinally-distal portion includes a tubular portion within which a valve member is disposed, and wherein unhousing the longitudinally-distal portion of the implant comprises unhousing the longitudinally-distal portion of the implant such that the tubular portion expands to form a lumen and the valve member regulates one-way flow of blood through the lumen, and wherein unhousing the longitudinally-distal portion of the implant comprises facilitating expansion of the implant such that the tubular portion expands and the flanges become longitudinally closer to the upstream support portion.

14. A method, comprising:

percutaneously advancing an implant to a native heart valve of a subject, the implant housed in a compressed state within a delivery tool;

unhousing a longitudinally-intermediate portion of the implant, the longitudinally-intermediate portion being longitudinally between a longitudinally-proximal portion of the implant and a longitudinally distal portion of the implant;

subsequently, unhousing the longitudinally-proximal portion of the implant; and subsequently, unhousing the longitudinally-distal portion of the implant, wherein:

percutaneously advancing the implant to the native heart valve comprises advancing the implant housed within a capsule of the delivery tool, the capsule having a distal capsule-portion and a proximal capsule-portion, unhousing the longitudinally-intermediate portion of the implant comprises unhousing the longitudinally-intermediate portion from within the distal capsule-portion by moving the distal capsule-portion distally with respect to the implant, unhousing the longitudinally-proximal portion comprises unhousing the longitudinally-proximal portion from within the proximal capsule-portion by moving the proximal capsule-portion proximally with respect to the implant, and unhousing the longitudinally-distal portion of the implant comprises deploying the longitudinally-distal portion of the implant from the distal capsule-portion.

15. The method according to claim 14, wherein deploying the longitudinally-distal portion of the implant from the distal capsule-portion comprises additionally moving the distal capsule-portion distally with respect to the implant.

16. Apparatus, comprising:
an implant for implantation at a native valve of a heart of a subject, the implant comprising a valve frame assembly comprising:
  a tubular portion having an upstream end and a downstream end that defines, in part, a longitudinally-distal portion of the implant;
  an upstream support portion, extending from the upstream end of the tubular portion, the upstream portion defining a longitudinally-proximal portion of the implant; and
  a plurality of tissue-engaging flanges coupled to the tubular portion at respective coupling points, the plurality of flanges defining a longitudinally-intermediate portion of the implant; and
a delivery tool:
  comprising a delivery capsule dimensioned (i) to house and retain the implant in a compressed state of the implant in which (a) the tubular portion is in a constrained-tubular-portion state, (b) the upstream support portion is in a constrained-upstream-support-portion state, and (c) the plurality of flanges are in a constrained-flange state, and (ii) to be advanced percutaneously to the heart of the subject while the implant is housed and in the compressed state, and operable from outside the subject to:
    transition the implant from the compressed state into an intermediate state of the implant by (1) unhousing the longitudinally-intermediate portion, while retaining the tubular portion in the constrained-tubular-portion state, and (2) subsequently, unhousing the longitudinally-proximal portion of the implant, while retaining at least the longitudinally-distal portion of the implant in a constrained state, and
    subsequently, unhouse the longitudinally-distal portion of the implant such that the implant assumes an expanded state,
wherein the tubular portion is configured such that, upon the implant transitioning from the intermediate state to the expanded state, the tubular portion expands and thereby moves the plurality of flanges longitudinally closer to the upstream support portion.

17. Apparatus, comprising:
an implant for implantation at a native valve of a heart of a subject, the implant comprising a valve frame assembly comprising:
  a tubular portion having an upstream end and a downstream end that defines, in part, a longitudinally-distal portion of the implant;
  an upstream support portion, extending from the upstream end of the tubular portion, the upstream portion defining a longitudinally-proximal portion of the implant; and
  a plurality of tissue-engaging flanges coupled to the tubular portion at respective coupling points, the plurality of flanges defining a longitudinally-intermediate portion of the implant; and
a delivery tool:
  comprising a delivery capsule dimensioned (i) to house and retain the implant in a compressed state of the implant in which (a) the tubular portion is in a constrained-tubular-portion state, (b) the upstream support portion is in a constrained-upstream-support-portion state, and (c) the plurality of flanges are in a constrained-flange state, and (ii) to be advanced percutaneously to the heart of the subject while the implant is housed and in the compressed state, and
  operable from outside the subject to:
    transition the implant from the compressed state into an intermediate state of the implant by (1) unhousing the longitudinally-intermediate portion, while retaining the tubular portion in the constrained-tubular-portion state, and (2) subsequently, unhousing the longitudinally-proximal portion of the implant, while retaining at least the longitudinally-distal portion of the implant in a constrained state, and
    subsequently, unhouse the longitudinally-distal portion of the implant such that the implant assumes an expanded state,
wherein the capsule of the delivery tool comprises a distal capsule-portion and a proximal capsule-portion, and wherein the capsule is configured such that:
upon the implant entering the intermediate state, (i) the distal capsule-portion is moved distally with respect to the implant to unhouse the longitudinally-intermediate portion of the implant, while still surrounding the longitudinally-distal portion of the implant, and (ii) the proximal capsule-portion is moved proximally with respect to the implant to unhouse the longitudinally-proximal portion, and
upon the implant entering the expanded state, the distal capsule-portion is moved further distally with respect to the implant to unhouse the longitudinally-distal portion of the implant.

* * * * *